(12) United States Patent
Zhang et al.

(10) Patent No.: US 10,011,616 B2
(45) Date of Patent: Jul. 3, 2018

(54) BORON-CONTAINING SMALL MOLECULES AS ANTIPROTOZOAL1 AGENTS

(71) Applicant: MMV MEDICINES FOR MALARIA VENTURE, Geneva (CH)

(72) Inventors: Yong-Kang Zhang, San Jose, CA (US); Jacob J. Plattner, Berkeley, CA (US); Robert T. Jacobs, Palo Alto, CA (US)

(73) Assignee: MMV MEDICINES FOR MALARIA VENTURE, Geneva (CH)

( * ) Notice: Subject to any disclaimer, the term of this patent is extended or adjusted under 35 U.S.C. 154(b) by 0 days.

(21) Appl. No.: 15/562,099

(22) PCT Filed: Apr. 8, 2016

(86) PCT No.: PCT/US2016/026772
§ 371 (c)(1),
(2) Date: Sep. 27, 2017

(87) PCT Pub. No.: WO2016/164814
PCT Pub. Date: Oct. 13, 2016

(65) Prior Publication Data
US 2018/0072760 A1 Mar. 15, 2018

Related U.S. Application Data

(60) Provisional application No. 62/152,605, filed on Apr. 24, 2015, provisional application No. 62/145,422, filed on Apr. 9, 2015.

(51) Int. Cl.
C07D 241/18 (2006.01)
C07F 5/02 (2006.01)

(52) U.S. Cl.
CPC ............ *C07F 5/025* (2013.01); *C07D 241/18* (2013.01)

(58) Field of Classification Search
CPC ................................ C07D 241/18; C07F 5/025
See application file for complete search history.

(56) References Cited

U.S. PATENT DOCUMENTS

2007/0155699 A1* 7/2007 Baker ..................... C07F 5/025
514/64

FOREIGN PATENT DOCUMENTS

WO    WO 2011/017125 A1    1/2011

OTHER PUBLICATIONS

Yi Xia, et al. "Synthesis and SAR of novel Benzoxaboroles as a new class of [beta] lactamase inhibitors," Bioorganic & Medicinal Chemistry Letters, vol. 21, No. 8, Apr. 1, 2011, pp. 2533-2536.
Zhang, Yong-Kang, et al. "Benzoxaborole Antimalarial Agents. Part 4. Discovery of Potent 6-(2-(Alkoxycarbonyl)pyrazinyl-5-oxy)-1,3-dihydro-1-hydroxy-2, 1-benzoxaboroles," Journal of Medicinal Chemistry, vol. 58, No. 13, Jun. 11, 2015, pp. 5344-5354.

* cited by examiner

*Primary Examiner* — Timothy R Rozof
(74) *Attorney, Agent, or Firm* — Saliwanchik, Lloyd & Eisenschenk

(57) ABSTRACT

This invention provides, among other things, novel compounds useful for treating protozoal infections, pharmaceutical compositions containing such compounds, as well as combinations of these compounds with at least one additional therapeutically effective agent. Formula (I) and (II)

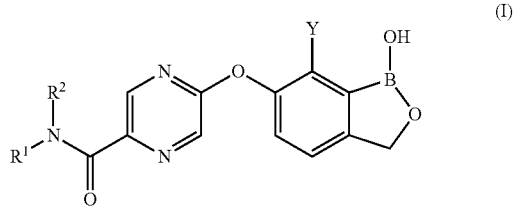

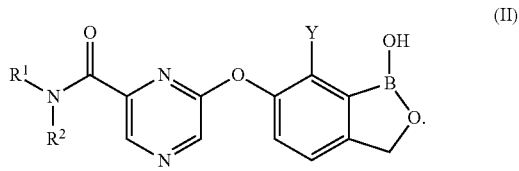

13 Claims, No Drawings

BORON-CONTAINING SMALL MOLECULES AS ANTIPROTOZOAL AGENTS

CROSS-REFERENCE TO RELATED APPLICATIONS

This application is a United States National Stage Application filed under 35 U.S.C. § 371 of International Patent Application No. PCT/US2016/026772 filed Apr. 8, 2016 and published as WO 2016/164814 A1, which claims priority to U.S. Provisional Application No. 62/145,422, filed Apr. 9, 2015 and U.S. Provisional Patent Application No. 62/152,605, filed Apr. 24, 2015, the entire contents of which applications is incorporated herein for all purposes by this reference.

BACKGROUND OF THE INVENTION

The global rise of protozoa resistant to antimicrobials in general, poses a major threat. Deployment of massive quantities of antimicrobial agents into the ecosphere during the past 60 years has introduced a powerful selective pressure for the emergence and spread of antimicrobial-resistant pathogens. Thus, there is a need to discover new broad spectrum antimicrobials, such as antiprotozoals, useful in combating microorganisms, especially those with multi-drug-resistance.

Boron-containing molecules, such as oxaboroles, useful as antimicrobials have been described previously, such as in U.S. Pat. Pubs. US20060234981 and US20070155699. Generally speaking, an oxaborole has the following structure and substituent numbering system:

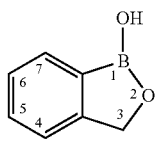

It has now been discovered that certain classes of oxaboroles which are surprisingly effective antiprotozoals. This, and other uses of these oxaboroles are described herein.

SUMMARY OF THE INVENTION

This invention provides, among other things, novel compounds useful for treating protozoa infections, pharmaceutical compositions containing such compounds, as well as combinations of these compounds with at least one additional therapeutically effective agent.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino)pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2(pddf)$ is 1,1'-Bis(diphenylphosphino) ferrocene]dichloropalladium(II); Pd/C is the catalyst known as palladium on carbon; $Pd_2(dba)_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; 3-F-4-$NO_2$-$PhSO_2Cl$ is 3-fluoro-4-nitrophenylsulfonyl chloride; 2-MeO-4-$NO_2$-$PhSO_2Cl$ is 2-methoxy-4-nitrophenylsulfonyl chloride; and $(EtO)_2POCH_2COOEt$ is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

"Combination of the invention," as used herein refers to the compounds and antiprotozoals discussed herein as well as acids, bases, salt forms (such as pharmaceutically acceptable salts), prodrugs, solvates and hydrates of these compounds and antiprotozoals.

"Boron containing compounds", as used herein, refers to the compounds of the invention that contain boron as part of their chemical formula.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "poly" as used herein means at least 2. For example, a polyvalent metal ion is a metal ion having a valency of at least 2.

"Moiety" refers to a radical of a molecule that is attached to the remainder of the molecule.

The symbol ~~~, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR""-C(NR'R"R"')=NR"", —NR""—C(NR'R")=NR"', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2m'+1), where m' is the total number of carbon atoms in such radical. R', R", R"', R"" and R""' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"', R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR""-C(NR'R"R"')=NR"", —NR""—C(NR'R")=NR"', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"', R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"', R"" and R""' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$-B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted C$_1$ or C$_2$ or C$_3$ or C$_4$ or C$_5$ or C$_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5 to 7-membered ring" or "5 or 6 or 7 membered ring" includes, for example phenyl, pyridinyl and piperidinyl. The term "5 to 7-membered heterocycloalkyl ring" "5 or 6 or 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, or l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Remington: The Science and Practice of Pharmacy, 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, *J of Controlled Release*, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to a broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minimizing the frequency (e.g., once daily) or route of dosing (e.g., oral), or to improve the taste or odor if given orally, or to minimize pain if given parenterally.

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye. Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

"Antibiotic", as used herein, is a compound which can kill or inhibit the growth of bacteria. The term antibiotic is broad enough to encompass acids, bases, salt forms (such as pharmaceutically acceptable salts), prodrugs, solvates and hydrates of the antibiotic compound.

"Antiprotozoal" or "antiprotozoa", as used herein, is a compound which can kill or inhibit the growth of protozoa. The term anti-protozoal or anti-protozoa is broad enough to encompass acids, bases, salt forms (such as pharmaceutically acceptable salts), prodrugs, solvates and hydrates of the antiprotozoal or antiprotozoa compound.

The term "microbial infection" or "infection by a microorganism" refers to any infection of a host by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., *J. of Medicinal Chem.* 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as a beta-lactamase or a leucyl t-RNA synthetase.

Boron is able to form additional covalent or dative bonds with oxygen, sulfur or nitrogen under some circumstances in this invention.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include $H^+$, $H_3O^+$, ammonium, potassium, calcium, magnesium, organic amino (such as choline or diethylamine or amino acids such as d-arginine, l-arginine, d-lysine, l-lysine), and sodium.

The compounds comprising a boron bonded to a carbon and three heteroatoms (such as three oxygens described in this section) can optionally contain a fully negatively charged boron or partially negatively charged boron. Due to the negative charge, a positively charged counterion may associate with this compound, thus forming a salt. Examples of positively charged counterions include $H^+$, $H_3O^+$, ammonium, potassium, calcium, magnesium, organic amino (such as choline or diethylamine or amino acids such as d-arginine, l-arginine, d-lysine, l-lysine), and sodium. These salts of the compounds are implicitly contained in descriptions of these compounds.

II. Introduction

The invention provides novel boron compounds. The novel compounds, as well as pharmaceutical compositions containing such compounds or combinations of these compounds with at least one additional therapeutically effective agent, can be used for, among other things, treating protozoal infections.

III. The Compounds

III.a) Cyclic Boronic Esters

In one aspect, the invention provides a compound of the invention. In an exemplary embodiment, the invention is a compound described herein. In an exemplary embodiment, the invention is a compound according to a formula described herein.

In another aspect, the invention provides a compound having a structure according to formula (I) and/or (II):

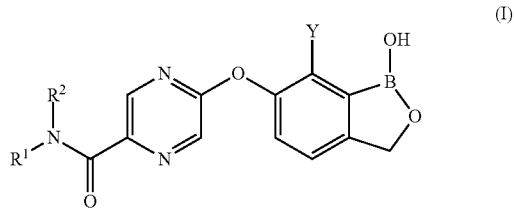

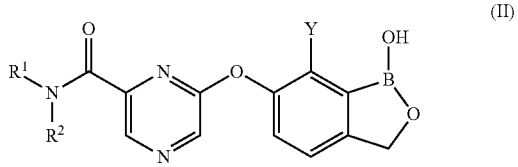

(II)

wherein Y is H or substituted or unsubstituted $C_1$-$C_3$ alkyl or substituted or unsubstituted $C_3$-$C_8$ cycloalkyl or substituted or unsubstituted $C_1$-$C_3$ alkyloxy, and $R^1$ and $R^2$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^1$ and $R^2$, along with the nitrogen to which they are attached, can be optionally joined to form a substituted or unsubstituted 3 to 8 membered ring, or a salt, or a hydrate, or a solvate thereof.

In an exemplary embodiment, the compound is according to formula (I), or a salt, or a hydrate, or a solvate thereof, wherein Y, $R^1$, and $R^2$ are each as described herein. In an exemplary embodiment, the compound is according to formula (II), or a salt, or a hydrate, or a solvate thereof, wherein Y, $R^1$, and $R^2$ are each as described herein.

In an exemplary embodiment, the compound is according to formula (I) and/or (II), wherein $R^1$ and $R^2$ are each as described herein, and Y is H. In an exemplary embodiment, the compound is according to formula (I) and/or (II), wherein $R^1$ and $R^2$ are each as described herein, and Y is methyl. In an exemplary embodiment, the compound is according to formula (I) and/or (II), wherein $R^1$ and $R^2$ are each as described herein, and Y is ethyl. In an exemplary embodiment, the compound is according to formula (I) and/or (II), wherein $R^1$ and $R^2$ are each as described herein, and Y is propyl. In an exemplary embodiment, the compound is according to formula (I) and/or (II), wherein $R^1$ and $R^2$ are each as described herein, and Y is isopropyl. In an exemplary embodiment, the compound is according to formula (I) and/or (II), wherein $R^1$ and $R^2$ are each as described herein, and Y is cyclopropyl. In an exemplary embodiment, the compound is according to formula (I) and/or (II), wherein $R^1$ and $R^2$ are each as described herein, and Y is cyclobutyl. In an exemplary embodiment, the compound is according to formula (I) and/or (II), wherein $R^1$ and $R^2$ are each as described herein, and Y is cyclopentyl. In an exemplary embodiment, the compound is according to formula (I) and/or (II), wherein $R^1$ and $R^2$ are each as described herein, and Y is cyclohexyl. In an exemplary embodiment, the compound is according to formula (I) and/or (II), wherein $R^1$ and $R^2$ are each as described herein, and Y is methoxy. In an exemplary embodiment, the compound is according to formula (I) and/or (II), wherein $R^1$ and $R^2$ are each as described herein, and Y is ethoxy. In an exemplary embodiment, the compound is according to formula (I) and/or (II), wherein $R^1$ and $R^2$ are each as described herein, and Y is propoxy. In an exemplary embodiment, the compound is according to formula (I) and/or (II), wherein $R^1$ and $R^2$ are each as described herein, and Y is isopropoxy.

In an exemplary embodiment, the compound is according to formula (I) and/or (II), wherein Y and $R^1$ are as described herein, and $R^2$ is H or unsubstituted $C_1$-$C_3$ alkyl or $C_1$-$C_3$ alkyl substituted with hydroxy. In an exemplary embodiment, the compound is according to formula (I) and/or (II), wherein Y and $R^1$ are as described herein, and $R^2$ is H. In an exemplary embodiment, the compound is according to formula (I) and/or (II), wherein Y and $R^1$ are as described herein, and $R^2$ is methyl. In an exemplary embodiment, the compound is according to formula (I) and/or (II), wherein Y and $R^1$ are as described herein, and $R^2$ is ethyl. In an exemplary embodiment, the compound is according to formula (I) and/or (II), wherein Y and $R^1$ are as described herein, and $R^2$ is unsubstituted $C_3$ alkyl. In an exemplary embodiment, the compound is according to formula (I) and/or (II), wherein Y and $R^1$ are as described herein, and $R^2$ is hydroxymethyl. In an exemplary embodiment, the compound is according to formula (I) and/or (II), wherein Y and $R^1$ are as described herein, and $R^2$ is hydroxyethyl. In an exemplary embodiment, the compound is according to formula (I) and/or (II), wherein Y and $R^1$ are as described herein, and $R^2$ is hydroxypropyl or hydroxyisopropyl.

In an exemplary embodiment, the compound is according to formula (I) wherein $R^1$ is as described herein, $R^2$ is H, and Y is $CH_3$. In an exemplary embodiment, the compound is according to formula (I) wherein $R^1$ is as described herein, $R^2$ is $CH_3$, and Y is $CH_3$. In an exemplary embodiment, the compound is according to formula (II) wherein $R^1$ is as described herein, $R^2$ is H, and Y is $CH_3$. In an exemplary embodiment, the compound is according to formula (II) wherein $R^1$ is as described herein, $R^2$ is $CH_3$, and Y is $CH_3$.

In an exemplary embodiment, the compound is according to formula (I) and/or (II), wherein Y and $R^2$ are as described herein, and $R^1$ is according to formula (III)

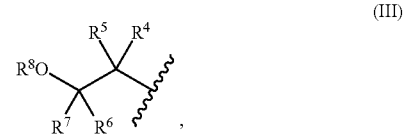

(III)

wherein $R^8$ is H or substituted or unsubstituted alkyl, and $R^4$ or $R^5$ or $R^6$ or $R^7$ are each independently selected from H, substituted or unsubstituted $C_1$-$C_6$ alkyl, substituted or unsubstituted heteroalkyl, substituted or unsubstituted $C_3$-$C_8$ cycloalkyl, substituted or unsubstituted aryl, or substituted or unsubstituted heteroaryl, and wherein $R^4$ and $R^5$, along with the atoms to which they are attached, can be optionally joined to form a substituted or unsubstituted 3 to 8 membered ring, and wherein $R^6$ and $R^7$, along with the atoms to which they are attached, can be optionally joined to form a substituted or unsubstituted 3 to 8 membered ring, and wherein $R^5$ and $R^6$, along with the atoms to which they are attached, can be optionally joined to form a substituted or unsubstituted 3 to 8 membered ring, wherein $R^6$ and $R^8$, along with the atoms to which they are attached, can be optionally joined to form a substituted or unsubstituted 3 to 8 membered ring.

In an exemplary embodiment, the compound is according to formula (I) and/or (II), wherein Y and $R^2$ are as described herein, and $R^1$ is according to formula (III), wherein $R^8$ is H, and $R^4$ or $R^5$ or $R^6$ or $R^7$ are as described herein. In an exemplary embodiment, the compound is according to formula (I) and/or (II), wherein Y and $R^2$ are as described herein, and $R^1$ is according to formula (III), wherein $R^8$ is —$CH_3$, and $R^4$ or $R^5$ or $R^6$ or $R^7$ are as described herein. In an exemplary embodiment, the compound is according to formula (I) and/or (II), wherein Y and $R^2$ are as described herein, and $R^1$ is according to formula (III), wherein $R^8$ is —$CH_2CH_3$, and $R^4$ or $R^5$ or $R^6$ or $R^7$ are as described herein. In an exemplary embodiment, the compound is according to formula (I) and/or (II), wherein Y and $R^2$ are as described herein, and $R^1$ is according to formula (III), wherein $R^8$ is $C_3$ alkyl, and $R^4$ or $R^5$ or $R^6$ or $R^7$ are as described herein.

In an exemplary embodiment, the compound is according to formula (I) and/or (II), wherein Y and $R^2$ are as described herein, and $R^1$ is according to formula (III), wherein $R^8$ is H or substituted or unsubstituted alkyl, and $R^4$ or $R^5$ or $R^6$ or $R^7$ are each independently selected from H or methyl or ethyl or ethenyl or unsubstituted $C_3$-$C_6$ alkyl, or $C_1$-$C_6$ alkyl substituted with one or more halogen, or $C_1$-$C_6$ alkyl substituted with phenyl, or unsubstituted $C_3$-$C_6$ cycloalkyl, or unsubstituted phenyl, or $C_1$-$C_3$ alkyl substituted with $C_1$-$C_3$ alkoxy, or $C_1$-$C_3$ alkyl substituted with $C_1$-$C_3$ alkylthio, or $C_1$-$C_3$ alkyl substituted with $C_1$-$C_3$ alkylsulfonyl. In an exemplary embodiment, the compound is according to formula (I) and/or (II), wherein Y and $R^2$ are as described herein, and $R^1$ is according to formula (III), wherein $R^8$ is H, and $R^4$ or $R^5$ or $R^6$ or $R^7$ are each independently selected from H or methyl or ethyl or trifluoromethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl. In an exemplary embodiment, the compound is according to formula (I) and/or (II), wherein Y and $R^2$ are as described herein, and $R^1$ is according to formula (III), wherein $R^8$ is H, and $R^4$ or $R^5$ or $R^6$ or $R^7$ are each independently selected from H or methyl or ethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl.

In an exemplary embodiment, the compound is according to formula (I) and/or (II), wherein Y and $R^2$ are as described herein, and $R^1$ is according to formula (III), wherein $R^8$ is H or substituted or unsubstituted alkyl, $R^7$ is H; and $R^4$ or $R^5$ or $R^6$ are each independently selected from H or methyl or ethyl or ethenyl or unsubstituted $C_3$-$C_6$ alkyl, or $C_1$-$C_6$ alkyl substituted with one or more halogen, or $C_1$-$C_6$ alkyl substituted with phenyl, or unsubstituted $C_3$-$C_6$ cycloalkyl, or unsubstituted phenyl, or $C_1$-$C_3$ alkyl substituted with $C_1$-$C_3$ alkoxy, or $C_1$-$C_3$ alkyl substituted with $C_1$-$C_3$ alkylthio, or $C_1$-$C_3$ alkyl substituted with $C_1$-$C_3$ alkylsulfonyl. In an exemplary embodiment, the compound is according to formula (I) and/or (II), wherein Y and $R^2$ are as described herein, and $R^1$ is according to formula (III), wherein $R^8$ is H, $R^7$ is H; and $R^4$ or $R^5$ or $R^6$ are each independently selected from H or methyl or ethyl or trifluoromethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl. In an exemplary embodiment, the compound is according to formula (I) and/or (II), wherein Y and $R^2$ are as described herein, and $R^1$ is according to formula (III), wherein $R^8$ is H, $R^7$ is H; and $R^4$ or $R^5$ or $R^6$ are each independently selected from H or methyl or ethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl.

In an exemplary embodiment, the compound is according to formula (I) and/or (II), wherein Y and $R^2$ are as described herein, and $R^1$ is according to formula (III), wherein $R^8$ is H or substituted or unsubstituted alkyl, $R^5$ is H; and $R^4$ or $R^6$ or $R^7$ are each independently selected from H or methyl or ethyl or ethenyl or unsubstituted $C_3$-$C_6$ alkyl, or $C_1$-$C_6$ alkyl substituted with one or more halogen, or $C_1$-$C_6$ alkyl substituted with phenyl, or unsubstituted $C_3$-$C_6$ cycloalkyl, or unsubstituted phenyl, or $C_1$-$C_3$ alkyl substituted with $C_1$-$C_3$ alkoxy, or $C_1$-$C_3$ alkyl substituted with $C_1$-$C_3$ alkylthio, or $C_1$-$C_3$ alkyl substituted with $C_1$-$C_3$ alkylsulfonyl. In an exemplary embodiment, the compound is according to formula (I) and/or (II), wherein Y and $R^2$ are as described herein, and $R^1$ is according to formula (III), wherein $R^8$ is H, $R^5$ is H; and $R^4$ or $R^6$ or $R^7$ are each independently selected from H or methyl or ethyl or trifluoromethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl. In an exemplary embodiment, the compound is according to formula (I) and/or (II), wherein Y and $R^2$ are as described herein, and $R^1$ is according to formula (III), wherein $R^8$ is H, $R^5$ is H; and $R^4$ or $R^6$ or $R^7$ are each independently selected from H or methyl or ethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl.

In an exemplary embodiment, the compound is according to formula (I) and/or (II), wherein Y and $R^2$ are as described herein, and $R^1$ is according to formula (III), wherein $R^8$ is H or substituted or unsubstituted alkyl, $R^6$ is H; $R^7$ is H; and $R^4$ or $R^5$ are each independently selected from H or methyl or ethyl or ethenyl or unsubstituted $C_3$-$C_6$ alkyl, or $C_1$-$C_6$ alkyl substituted with one or more halogen, or $C_1$-$C_6$ alkyl substituted with phenyl, or unsubstituted $C_3$-$C_6$ cycloalkyl, or unsubstituted phenyl, or $C_1$-$C_3$ alkyl substituted with $C_1$-$C_3$ alkoxy, or $C_1$-$C_3$ alkyl substituted with $C_1$-$C_3$ alkylthio, or $C_1$-$C_3$ alkyl substituted with $C_1$-$C_3$ alkylsulfonyl. In an exemplary embodiment, the compound is according to formula (I) and/or (II), wherein Y and $R^2$ are as described herein, and $R^1$ is according to formula (III), wherein $R^8$ is H, $R^6$ is H; $R^7$ is H; and $R^4$ or $R^5$ are each independently selected from H or methyl or ethyl or trifluoromethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl. In an exemplary embodiment, the compound is according to formula (I) and/or (II), wherein Y and $R^2$ are as described herein, and $R^1$ is according to formula (III), wherein $R^8$ is H, $R^6$ is H; $R^7$ is H; and $R^4$ or $R^5$ are each independently selected from H or methyl or ethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl.

In an exemplary embodiment, the compound is according to formula (I) and/or (II), wherein Y and $R^2$ are as described herein, and $R^1$ is according to formula (III), wherein $R^8$ is H or substituted or unsubstituted alkyl, $R^5$ is H; $R^6$ is H; $R^7$ is H; and $R^4$ is selected from methyl or ethyl or ethenyl or unsubstituted $C_3$-$C_6$ alkyl, or $C_1$-$C_6$ alkyl substituted with one or more halogen, or $C_1$-$C_6$ alkyl substituted with phenyl, or unsubstituted $C_3$-$C_6$ cycloalkyl, or unsubstituted phenyl, or $C_1$-$C_3$ alkyl substituted with $C_1$-$C_3$ alkoxy, or $C_1$-$C_3$ alkyl substituted with $C_1$-$C_3$ alkylthio, or $C_1$-$C_3$ alkyl substituted with $C_1$-$C_3$ alkylsulfonyl. In an exemplary embodiment, the compound is according to formula (I) and/or (II), wherein Y and $R^2$ are as described herein, and $R^1$ is according to formula (III), wherein $R^8$ is H, $R^5$ is H; $R^6$ is H; $R^7$ is H; and $R^4$ is selected from methyl or ethyl or trifluoromethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl. In an exemplary embodiment, the compound is according to formula (I) and/or (II), wherein Y and $R^2$ are as described herein, and $R^1$ is according to formula (III), wherein $R^8$ is H, $R^5$ is H; $R^6$ is H; $R^7$ is H; and $R^4$ is selected from methyl or ethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl.

In an exemplary embodiment, the compound is according to formula (I) and/or (II), wherein Y, $R^2$, and $R^8$ are as described herein, and $R^1$ is according to formula (III), wherein $R^4$ is H; $R^5$ is H; $R^6$ is H; $R^7$ is H. In an exemplary embodiment, the compound is according to formula (I) and/or (II), wherein Y, $R^2$, and $R^8$ are as described herein, and $R^1$ is according to formula (III), wherein $R^4$ is H; $R^5$ is H; and $R^6$ and $R^7$ are each independently selected from H and unsubstituted $C_1$-$C_6$ alkyl. In an exemplary embodiment, the compound is according to formula (I) and/or (II), wherein Y, $R^2$, $R^4$, $R^5$, and $R^8$ are as described herein, and $R^1$ is according to formula (III), wherein $R^6$ and $R^7$ are each independently selected from H and unsubstituted $C_1$-$C_6$ alkyl. In an exemplary embodiment, the compound is according to formula (I) and/or (II), wherein Y, $R^2$, $R^5$, and $R^8$ are as described herein, and $R^1$ is according to formula (III), wherein $R^4$ is H, and wherein $R^6$ and $R^7$ are each independently selected from H and unsubstituted $C_1$-$C_6$ alkyl. In an exemplary embodiment, the compound is according to formula (I) and/or (II), wherein Y, $R^2$, $R^5$, and $R^8$ are as described herein, and $R^1$ is according to formula (III), wherein $R^4$ is H, $R^6$ is H, and $R^7$ is unsubstituted $C_1$-$C_6$ alkyl. In an exemplary embodiment, the compound is according to formula (I) and/or (II), wherein Y, $R^2$, and $R^8$ are as described herein, and $R^1$ is according to formula (III), wherein $R^4$ is H, $R^6$ is H, and $R^5$ is methyl or ethyl or propyl or isopropyl and $R^7$ is methyl or ethyl or propyl or isopropyl. In an exemplary embodiment, the compound is according to formula (I) and/or (II), wherein Y, $R^2$, and $R^8$ are as described herein, and $R^1$ is according to formula (III), wherein $R^4$ is H, $R^6$ is H, and $R^5$ is methyl and $R^7$ is methyl. In an exemplary embodiment, the compound is according to formula (I) and/or (II), wherein Y, $R^2$, and $R^8$ are as described herein, and $R^1$ is according to formula (III), wherein $R^4$ is H; $R^5$ is H; $R^6$ is H; $R^7$ is methyl or ethyl or propyl or isopropyl. In an exemplary embodiment, the compound is according to formula (I) and/or (II), wherein Y, $R^2$, and $R^8$ are as described herein, and $R^1$ is according to formula (III), wherein $R^4$ is H; $R^5$ is H; $R^6$ is H; $R^7$ is methyl. In an exemplary embodiment, the compound is according to formula (I) and/or (II), wherein Y, $R^2$, and $R^8$ are as described herein, and $R^1$ is according to formula (III), wherein $R^4$ is H; $R^5$ is H; $R^6$ is methyl or ethyl; and $R^7$ is methyl or ethyl. In an exemplary embodiment, the compound is according to formula (I) and/or (II), wherein Y, $R^2$, and $R^8$ are as described herein, and $R^1$ is according to formula (III), wherein $R^4$ is H; $R^5$ is H; $R^6$ is methyl; and $R^7$ is methyl. In an exemplary embodiment, the compound is according to formula (I) and/or (II), wherein Y, $R^2$, and $R^8$ are as described herein, and $R^1$ is according to formula (III), wherein $R^4$ is H; $R^5$ is H; and $R^6$ and $R^7$ are each independently selected from H and unsubstituted $C_1$-$C_6$ alkyl.

In an exemplary embodiment, the compound is according to formula (I) and/or (II), wherein Y, $R^2$, and $R^8$ are as described herein, and $R^1$ is according to formula (III), wherein $R^6$ is H; $R^7$ is H; and $R^4$ and $R^5$ are each independently selected from H and unsubstituted $C_1$-$C_6$ alkyl. In an exemplary embodiment, the compound is according to formula (I) and/or (II), wherein Y, $R^2$, $R^6$, $R^7$, and $R^8$ are as described herein, and $R^1$ is according to formula (III), wherein $R^4$ and $R^5$ are each independently selected from H and unsubstituted $C_1$-$C_6$ alkyl. In an exemplary embodiment, the compound is according to formula (I) and/or (II), wherein Y, $R^2$, $R^7$, and $R^8$ are as described herein, and $R^1$ is according to formula (III), wherein $R^6$ is H, and wherein $R^4$ and $R^5$ are each independently selected from H and unsubstituted $C_1$-$C_6$ alkyl. In an exemplary embodiment, the compound is according to formula (I) and/or (II), wherein Y, $R^2$, $R^7$, and $R^8$ are as described herein, and $R^1$ is according to formula (III), wherein $R^4$ is H, $R^6$ is H, and $R^5$ is unsubstituted $C_1$-$C_6$ alkyl. In an exemplary embodiment, the compound is according to formula (I) and/or (II), wherein Y, $R^2$, and $R^8$ are as described herein, and $R^1$ is according to formula (III), wherein $R^6$ is H; $R^7$ is H; $R^4$ is H; $R^5$ is ethyl. In an exemplary embodiment, the compound is according to formula (I) and/or (II), wherein Y, $R^2$, and $R^8$ are as described herein, and $R^1$ is according to formula (III), wherein $R^6$ is H; $R^7$ is H; $R^4$ is H; $R^5$ is propyl or isopropyl. In an exemplary embodiment, the compound is according to formula (I) and/or (II), wherein Y, $R^2$, and $R^8$ are as described herein, and $R^1$ is according to formula (III), wherein $R^6$ is H; $R^7$ is H; $R^4$ is H; $R^5$ is butyl or isobutyl or secbutyl or tert-butyl. In an exemplary embodiment, the compound is according to formula (I) and/or (II), wherein Y, $R^2$, and $R^8$ are as described herein, and $R^1$ is according to formula (III), wherein $R^6$ is H; $R^7$ is H; $R^4$ is H; $R^5$ is methyl. In an exemplary embodiment, the compound is according to formula (I) and/or (II), wherein Y, $R^2$, and $R^8$ are as described herein, and $R^1$ is according to formula (III), wherein $R^6$ is H; $R^7$ is H; $R^4$ is methyl or ethyl; and $R^5$ is methyl or ethyl. In an exemplary embodiment, the compound is according to formula (I) and/or (II), wherein Y, $R^2$, and $R^8$ are as described herein, and $R^1$ is according to formula (III), wherein $R^6$ is H; $R^7$ is H; $R^4$ is methyl; and $R^5$ is methyl. In an exemplary embodiment, the compound is according to formula (I) and/or (II), wherein Y, $R^2$, and $R^8$ are as described herein, and $R^1$ is according to formula (III), wherein $R^6$ is H; $R^7$ is H; and $R^4$ and $R^5$ are each independently selected from H and unsubstituted $C_1$-$C_6$ alkyl.

In an exemplary embodiment, the compound is according to formula (I) and/or (II), wherein Y, $R^2$, $R^6$, $R^7$, and $R^8$ are as described herein, and $R^1$ is according to formula (III), and wherein $R^4$ and $R^5$, along with the atoms to which they are attached, are joined to form a substituted or unsubstituted 3 or 4 or 5 membered ring. In an exemplary embodiment, the compound is according to formula (I) and/or (II), wherein Y, $R^2$, $R^6$, $R^7$, and $R^8$ are as described herein, and $R^1$ is according to formula (III), and wherein $R^4$ and $R^5$, along with the atoms to which they are attached, are joined to form a substituted or unsubstituted 6 or 7 or 8 membered ring. In an exemplary embodiment, the compound is according to formula (I) and/or (II), wherein Y, $R^2$, and $R^8$ are as described herein, and $R^1$ is according to formula (III), wherein $R^6$ is H; $R^7$ is H; and $R^4$ and $R^5$, along with the atoms to which they are attached, are joined to form a substituted or unsubstituted 3 or 4 or 5 or 6 or 7 or 8 membered ring. In an exemplary embodiment, the compound is according to formula (I) and/or (II), wherein Y, $R^2$, and $R^8$ are as described herein, and $R^1$ is according to formula (III), wherein $R^6$ is H; $R^7$ is H; and $R^4$ and $R^5$, along with the atoms to which they are attached, are joined to form a cyclopropyl ring.

In an exemplary embodiment, the compound is according to formula (I) and/or (II), wherein Y, $R^2$, $R^4$, $R^5$, and $R^8$ are as described herein, and $R^1$ is according to formula (III), and wherein $R^6$ and $R^7$, along with the atoms to which they are attached, are joined to form a substituted or unsubstituted 3 or 4 or 5 membered ring. In an exemplary embodiment, the compound is according to formula (I) and/or (II), wherein Y, $R^2$, $R^4$, $R^5$, and $R^8$ are as described herein, and $R^1$ is according to formula (III), and wherein $R^6$ and $R^7$, along with the atoms to which they are attached, are joined to form a substituted or unsubstituted 6 or 7 or 8 membered ring. In an exemplary embodiment, the compound is according to formula (I) and/or (II), wherein Y, $R^2$, and $R^8$ are as described herein, and $R^1$ is according to formula (III), wherein $R^4$ is H; $R^5$ is H; and $R^6$ and $R^7$, along with the atoms to which they are attached, are joined to form a substituted or unsubstituted 3 or 4 or 5 or 6 or 7 or 8 membered ring. In an exemplary embodiment, the compound is according to formula (I) and/or (II), wherein Y, $R^2$, and $R^8$ are as described herein, and $R^1$ is according to formula (III), wherein $R^4$ is H; $R^5$ is H; and $R^6$ and $R^7$, along with the atoms to which they are attached, are joined to form a cyclopropyl ring.

In an exemplary embodiment, the compound is according to formula (I) and/or (II), wherein Y, $R^2$, $R^4$, $R^7$, and $R^8$ are as described herein, and $R^1$ is according to formula (III), and $R^5$ and $R^6$, along with the atoms to which they are attached, are joined to form a substituted or unsubstituted 3 or 4 or 5 membered ring. In an exemplary embodiment, the compound is according to formula (I) and/or (II), wherein Y, $R^2$, $R^4$, $R^7$, and $R^8$ are as described herein, and $R^1$ is according to formula (III), and $R^5$ and $R^6$, along with the atoms to which they are attached, are joined to form a substituted or unsubstituted 6 or 7 or 8 membered ring. In an exemplary embodiment, the compound is according to formula (I) and/or (II), wherein Y, $R^2$, and $R^8$ are as described herein, and $R^1$ is according to formula (III), wherein $R^4$ is H; $R^7$ is H; and wherein $R^5$ and $R^6$, along with the atoms to which they are attached, are joined to form a substituted or unsubstituted 3 or 4 or 5 or 6 or 7 or 8 membered ring. In an exemplary embodiment, the compound is according to formula (I) and/or (II), wherein Y and $R^2$, and $R^1$ is according to formula (III), wherein $R^4$ is H; $R^7$ is H; $R^8$ is H; and wherein $R^5$ and $R^6$, along with the atoms to which they are attached, are joined to form a substituted or unsubstituted 3 or 4 or 5 or 6 or 7 or 8 membered ring. In an exemplary embodiment, the compound is according to formula (I) and/or (II), wherein Y, $R^2$, and $R^8$ are as described herein, and $R^1$ is according to formula (III), wherein $R^4$ is H; $R^7$ is H; and wherein $R^5$ and $R^6$, along with the atoms to which they are attached, are joined to form a 3 or 4 or 5 or 6 or 7 or 8 membered ring substituted with hydroxy. In an exemplary embodiment, the compound is according to formula (I) and/or (II), wherein Y, $R^2$, and $R^8$ are as described herein, and $R^1$ is according to formula (III), wherein $R^4$ is H; $R^7$ is H; and wherein $R^5$ and $R^6$, along with the atoms to which they are attached, are joined to form a cyclopentyl ring.

In an exemplary embodiment, the compound is according to formula (I) and/or (II), wherein Y, $R^2$, $R^4$, $R^5$, and $R^8$ are as described herein, and $R^1$ is according to formula (III), and $R^6$ and $R^8$, along with the atoms to which they are attached, are joined to form a substituted or unsubstituted 3 or 4 or 5 membered ring. In an exemplary embodiment, the compound is according to formula (I) and/or (II), wherein Y, $R^2$, $R^4$, $R^5$, and $R^8$ are as described herein, and $R^1$ is according to formula (III), and $R^6$ and $R^8$, along with the atoms to which they are attached, are joined to form a substituted or unsubstituted 6 or 7 or 8 membered ring. In an exemplary embodiment, the compound is according to formula (I) and/or (II), wherein Y, $R^2$, and $R^5$ are as described herein, and $R^1$ is according to formula (III), wherein $R^4$ is H; $R^7$ is H; and wherein $R^6$ and $R^8$, along with the atoms to which they are attached, are joined to form a substituted or unsubstituted 3 or 4 or 5 or 6 or 7 or 8 membered ring.

In an exemplary embodiment, the compound is according to formula (I), wherein Y is as described herein, and $R^1$ and $R^2$, along with the nitrogen to which they are attached, are joined to form a substituted or unsubstituted 3 to 8 membered ring. In an exemplary embodiment, the compound is according to formula (I), wherein Y is —$CH_3$, and $R^1$ and $R^2$, along with the nitrogen to which they are attached, are joined to form a substituted or unsubstituted 3 to 8 membered ring.

In an exemplary embodiment, the compound is according to formula (II), wherein Y is as described herein, and $R^1$ and $R^2$, along with the nitrogen to which they are attached, are joined to form a substituted or unsubstituted 3 to 8 membered ring. In an exemplary embodiment, the compound is according to formula (II), wherein Y is —$CH_3$, and $R^1$ and $R^2$, along with the nitrogen to which they are attached, are joined to form a substituted or unsubstituted 3 to 8 membered ring. In an exemplary embodiment, the compound is according to formula (I) and/or (II), wherein Y is as described herein, and $R^1$ and $R^2$, along with the nitrogen to which they are attached, are joined to form hydroxy substituted $C_3$-$C_8$ heterocycloalkyl. In an exemplary embodiment, the compound is according to formula (I) and/or (II), wherein Y is $CH_3$, and $R^1$ and $R^2$, along with the nitrogen to which they are attached, are joined to form hydroxy substituted $C_3$-$C_8$ heterocycloalkyl.

In an exemplary embodiment, the compound is according to formula (I) wherein $R^1$ is according to formula (III), $R^4$, $R^5$, $R^6$, and $R^7$ are as described herein, $R^8$ is H, $R^2$ is H, and Y is $CH_3$. In an exemplary embodiment, the compound is according to formula (I) wherein $R^1$ is according to formula (III), $R^4$, $R^5$, $R^6$, and $R^7$ are as described herein, $R^8$ is H, $R^2$ is $CH_3$, and Y is $CH_3$. In an exemplary embodiment, the compound is according to formula (II) wherein $R^1$ is according to formula (III), $R^4$, $R^5$, $R^6$, and $R^7$ are as described herein, $R^8$ is H, $R^2$ is H, and Y is $CH_3$. In an exemplary embodiment, the compound is according to formula (II) wherein $R^1$ is according to formula (III), $R^4$, $R^5$, $R^6$, and $R^7$ are as described herein, $R^8$ is H, $R^2$ is $CH_3$, and Y is $CH_3$.

In an exemplary embodiment, the compound is according to formula (I) and/or (II), wherein $R^2$, $R^8$, are as described herein, and $R^1$ is according to formula (III), wherein Y is $CH_3$, $R^4$ is H; $R^5$ is H; $R^6$ is H; $R^7$ is H. In an exemplary embodiment, the compound is according to formula (I) and/or (II), wherein Y, $R^8$, are as described herein, and $R^1$ is according to formula (III), wherein $R^2$ is H, $R^4$ is H; $R^5$ is H; $R^6$ is H; $R^7$ is H.

In another aspect, the invention provides a compound having a structure according to formula (Ia) and/or (IIa):

(Ia)

(IIa)

wherein Y is H or substituted or unsubstituted $C_1$-$C_3$ alkyl or substituted or unsubstituted $C_3$-$C_8$ cycloalkyl or substituted or unsubstituted $C_1$-$C_3$ alkyloxy, A is a substituted or unsubstituted 3 to 8 membered ring, or a salt, or a hydrate, or a solvate thereof. In an exemplary embodiment, the compound is according to formula (Ia), wherein Y is as described herein, and A is a substituted or unsubstituted 3 to 8 membered ring. In an exemplary embodiment, the compound is according to formula (IIa), wherein Y is as described herein, and A is a substituted or unsubstituted 3 to 8 membered ring. In an exemplary embodiment, the compound is according to formula (Ia), wherein Y is $CH_3$, and A is a substituted or unsubstituted 3 to 8 membered ring. In an exemplary embodiment, the compound is according to formula (IIa), wherein Y is $CH_3$, and A is a substituted or unsubstituted 3 to 8 membered ring.

In an exemplary embodiment, the compound is according to formula (Ia) and/or (IIa), wherein Y is as described herein, and A is an unsubstituted 3 membered ring. In an exemplary embodiment, the compound is according to formula (Ia) and/or (IIa), wherein Y is $CH_3$, and A is an unsubstituted 3 membered ring. In an exemplary embodiment, the compound is according to formula (Ia) and/or (IIa), wherein Y is as described herein, and A is an unsubstituted 4 membered ring. In an exemplary embodiment, the compound is according to formula (Ia) and/or (IIa), wherein Y is $CH_3$, and A is an unsubstituted 4 membered ring. In an exemplary embodiment, the compound is according to formula (Ia) and/or (IIa), wherein Y is as described herein, and A is an unsubstituted 5 membered ring. In an exemplary embodiment, the compound is according to formula (Ia) and/or (IIa), wherein Y is $CH_3$, and A is an unsubstituted 5 membered ring. In an exemplary embodiment, the compound is according to formula (Ia) and/or (IIa), wherein Y is as described herein, and A is an unsubstituted 6 membered ring. In an exemplary embodiment, the compound is according to formula (Ia) and/or (IIa), wherein Y is $CH_3$, and A is an unsubstituted 6 membered ring. In an exemplary embodiment, the compound is according to formula (Ia) and/or (IIa), wherein Y is as described herein, and A is an unsubstituted 7 membered ring. In an exemplary embodiment, the compound is according to formula (Ia) and/or (IIa), wherein Y is $CH_3$, and A is an unsubstituted 7 membered ring. In an exemplary embodiment, the compound is according to formula (Ia) and/or (IIa), wherein Y is as described herein, and A is an unsubstituted 8 membered ring. In an exemplary embodiment, the compound is according to formula (Ia) and/or (IIa), wherein Y is $CH_3$, and A is an unsubstituted 8 membered ring.

In an exemplary embodiment, the compound is according to formula (Ia) and/or (IIa), wherein Y is as described herein, and A is substituted with hydroxy. In an exemplary embodiment, the compound is according to formula (Ia) and/or (IIa), wherein Y is as described herein, and A is substituted with substituted or unsubstituted alkyl. In an exemplary embodiment, the compound is according to formula (Ia) and/or (IIa), wherein Y is as described herein, and A is substituted with unsubstituted $C_1$-$C_6$ alkyl. In an exemplary embodiment, the compound is according to formula (Ia) and/or (IIa), wherein Y is as described herein, and A is substituted with substituted $C_1$-$C_6$ alkyl. In an exemplary embodiment, the compound is according to formula (Ia) and/or (IIa), wherein Y is as described herein, and A is substituted with halosubstituted $C_1$-$C_6$ alkyl. In an exemplary embodiment, the compound is according to formula (Ia) and/or (IIa), wherein Y is as described herein, and A is substituted with fluorosubstituted $C_1$-$C_6$ alkyl. In an exemplary embodiment, the compound is according to formula (Ia) and/or (IIa), wherein Y is as described herein, and A is substituted with halosubstituted methyl. In an exemplary embodiment, the compound is according to formula (Ia) and/or (IIa), wherein Y is as described herein, and A is substituted with fluorosubstituted methyl. In an exemplary embodiment, the compound is according to formula (Ia) and/or (IIa), wherein Y is as described herein, and A is substituted with trifluoromethyl. In an exemplary embodiment, the compound is according to formula (Ia) and/or (IIa), wherein Y is as described herein, and A is substituted with unsubstituted $C_6$-$C_8$ cycloalkyl. In an exemplary embodiment, the compound is according to formula (Ia) and/or (IIa), wherein Y is as described herein, and A is substituted with substituted $C_6$-$C_8$ cycloalkyl. In an exemplary embodiment, the compound is according to formula (Ia) and/or (IIa), wherein Y is as described herein, and A is substituted with unsubstituted cyclopropyl. In an exemplary embodiment, the compound is according to formula (Ia) and/or (IIa), wherein Y is as described herein, and A is substituted with substituted cyclopropyl. In an exemplary embodiment, the compound is according to formula (Ia) and/or (IIa), wherein Y is as described herein, and A is substituted with unsubstituted cyclobutyl. In an exemplary embodiment, the compound is according to formula (Ia) and/or (IIa), wherein Y is as described herein, and A is substituted with substituted cyclobutyl. In an exemplary embodiment, the compound is according to formula (Ia) and/or (IIa), wherein Y is as described herein, and A is substituted with unsubstituted cyclopentyl. In an exemplary embodiment, the compound is according to formula (Ia) and/or (IIa), wherein Y is as described herein, and A is substituted with substituted cyclopentyl.

In an exemplary embodiment, the compound is according to formula (Ia) and/or (IIa), wherein Y is as described herein, and is

, $R^8$ is H or substituted or unsubstituted alkyl, and $R^4$ or $R^5$ or $R^6$ are each independently selected from H, substituted or unsubstituted $C_1$-$C_6$ alkyl, substituted or unsubstituted heteroalkyl, substituted or unsubstituted $C_3$-$C_8$ cycloalkyl, substituted or unsubstituted aryl, or substituted or unsubstituted heteroaryl, and wherein $R^4$ and $R^5$, along with the atoms to which they are attached, can be optionally joined to form a substituted or unsubstituted 3 to 8 membered ring, and wherein $R^5$ and $R^6$, along with the atoms to which they are attached, can be optionally joined to form a substituted or unsubstituted 3 to 8 membered ring, wherein $R^6$ and $R^8$, along with the atoms to which they are attached, can be optionally joined to form a substituted or unsubstituted 3 to 8 membered ring. In an exemplary embodiment, the compound is according to formula (Ia) and/or (IIa), wherein Y is as described herein, and/is

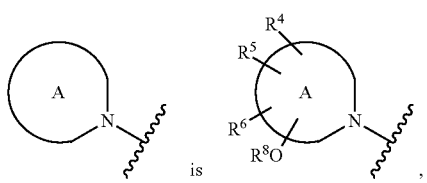

wherein $R^8$ is H or substituted or unsubstituted alkyl, and $R^4$ or $R^5$ or $R^6$ are each independently selected from H or methyl or ethyl or ethenyl or unsubstituted $C_3$-$C_6$ alkyl, or $C_1$-$C_6$ alkyl substituted with one or more halogen, or $C_1$-$C_6$ alkyl substituted with phenyl, or unsubstituted $C_3$-$C_6$ cycloalkyl, or unsubstituted phenyl, or $C_1$-$C_3$ alkyl substituted with $C_1$-$C_3$ alkoxy, or $C_1$-$C_3$ alkyl substituted with $C_1$-$C_3$ alkylthio, or $C_1$-$C_3$ alkyl substituted with $C_1$-$C_3$ alkylsulfonyl. In an exemplary embodiment, the compound is according to formula (Ia) and/or (IIa), wherein Y and $R^2$ are as described herein, and

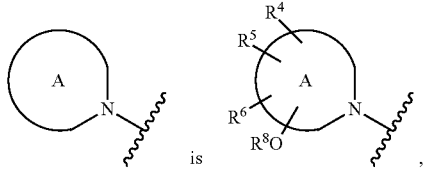

wherein $R^8$ is substituted or unsubstituted alkyl, and $R^4$ or $R^5$ or $R^6$ are each independently selected from H or methyl or ethyl or trifluoromethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl. In an exemplary embodiment, the compound is according to formula (I) and/or (II), wherein Y and $R^2$ are as described herein, and

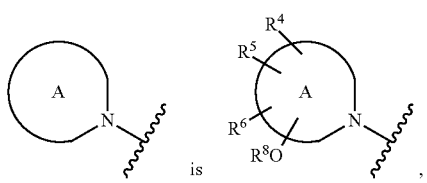

wherein $R^8$ is H, and $R^4$ or $R^5$ or $R^6$ are each independently selected from H or methyl or ethyl or propyl or isopropyl or butyl or isobutyl or secbutyl or t-butyl or phenyl or benzyl or 2-phenylethyl or 1-phenylethyl or ethenyl or cyclopropyl or cyclobutyl or cyclopentyl or cyclohexyl or methoxymethyl or methylthiomethyl or methylsulfonylmethyl or 2,2,2 trifluoroethyl.

In an exemplary embodiment, the compound is according to formula (Ia) and/or (IIa), wherein Y is as described herein, and

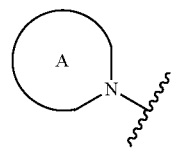

is substituted

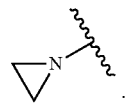

In an exemplary embodiment, the compound is according to formula (Ia) and/or (IIa), wherein Y is as described herein, and

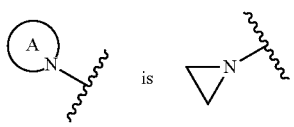

substituted with hydroxy or substituted with $C_1$-$C_4$ alkyl or combinations thereof.

In an exemplary embodiment, the compound is according to formula (Ia) and/or (IIa), wherein Y is as described herein, and

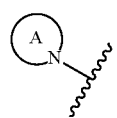

is substituted

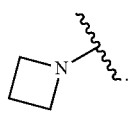

In an exemplary embodiment, the compound is according to formula (Ia) and/or (IIa), wherein Y is as described herein, and

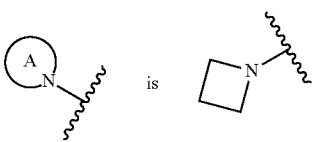 is 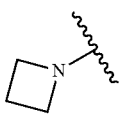

is substituted with hydroxy or substituted with $C_1$-$C_4$ alkyl or combinations thereof.

In an exemplary embodiment, the compound is according to formula (Ia) and/or (IIa), wherein Y is as described herein, and

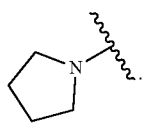

is substituted

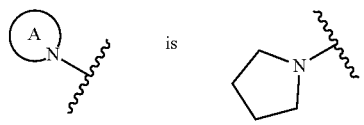

In an exemplary embodiment, the compound is according to formula (Ia) and/or (IIa), wherein Y is as described herein, and

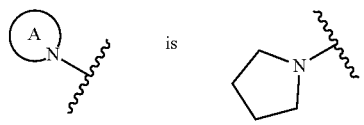 is 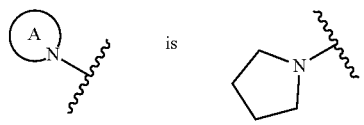

substituted with hydroxy or substituted with $C_1$-$C_4$ alkyl or combinations thereof.

In an exemplary embodiment, the compound is according to formula (Ia) and/or (IIa), wherein Y is as described herein, and

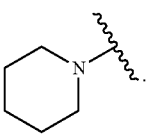 [SMILES: *N1CCCCC1]

is substituted

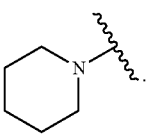 [SMILES: *N1CCCCC1]

In an exemplary embodiment, the compound is according to formula (Ia) and/or (IIa), wherein Y is as described herein, and

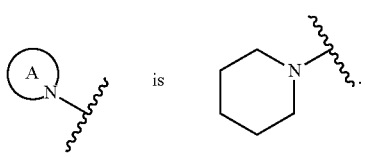 is 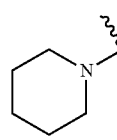

substituted with hydroxy or substituted with $C_1$-$C_4$ alkyl or combinations thereof.

In an exemplary embodiment, the compound is according to formula (Ia) and/or (IIa), wherein Y is as described herein, and

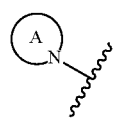

is substituted

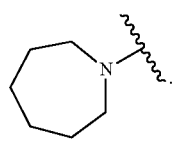 [SMILES: *N1CCCCCC1]

In an exemplary embodiment, the compound is according to formula (Ia) and/or (IIa), wherein Y is as described herein, and

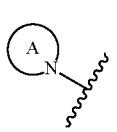 is 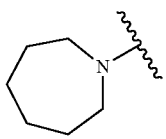

substituted with hydroxy or substituted with $C_1$-$C_4$ alkyl or combinations thereof.

In an exemplary embodiment, the compound is according to formula (Ia) and/or (IIa), wherein Y is as described herein, and

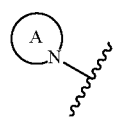

is substituted

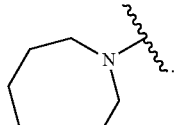

In an exemplary embodiment, the compound is according to formula (Ia) and/or (IIa), wherein Y is as described herein, and

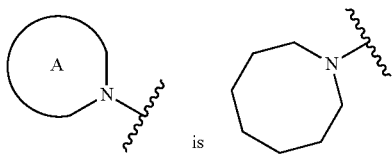 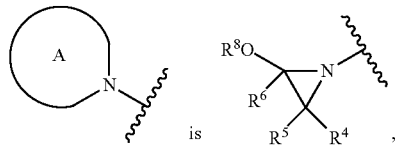

substituted with hydroxy or substituted with $C_1$-$C_4$ alkyl or combinations thereof.

In an exemplary embodiment, the compound is according to formula (Ia) and/or (IIa), wherein Y is as described herein, and

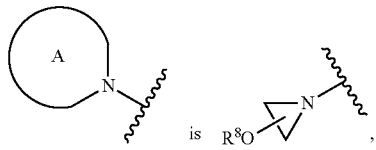

wherein $R^8$ is as described herein. In an exemplary embodiment, the compound is according to formula (Ia) and/or (IIa), wherein Y is as described herein, and

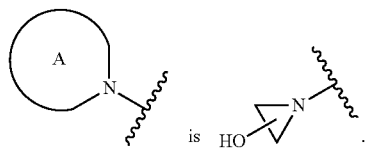

In an exemplary embodiment, the compound is according to formula (Ia) and/or (IIa), wherein Y is as described herein, and

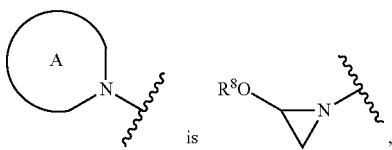

wherein $R^8$ is as described herein. In an exemplary embodiment, the compound is according to formula (Ia) and/or (IIa), wherein Y is as described herein, and

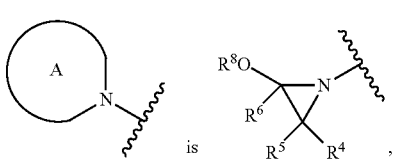

wherein $R^4$ or $R^5$ or $R^6$ are as described herein. In an exemplary embodiment, the compound is according to formula (Ia) and/or (IIa), wherein Y is as described herein, and wherein $R^4$ or $R^5$ are as described herein, $R^8$ is H, and $R^6$ is unsubstituted $C_1$-$C_4$ alkyl or halosubstituted $C_1$-$C_4$ alkyl or unsubstituted $C_3$-$C_5$ cycloalkyl, $R^8$ are as described herein. In an exemplary embodiment, the compound is according to formula (Ia) and/or (IIa), wherein Y is as described herein, and

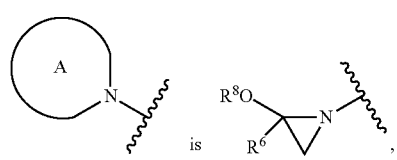

wherein $R^6$ or $R^8$ are as described herein.

In an exemplary embodiment, the compound is according to formula (Ia) and/or (IIa), wherein Y is as described herein, and

wherein $R^8$ is as described herein. In an exemplary embodiment, the compound is according to formula (Ia) and/or (IIa), wherein Y is as described herein, and

wherein $R^8$ is as described herein. In an exemplary embodiment, the compound is according to formula (Ia) and/or (IIa), wherein Y is as described herein, and

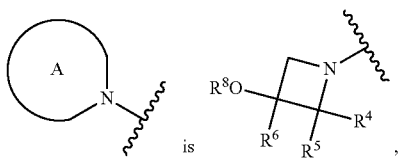

wherein $R^4$ or $R^5$ or $R^6$ or $R^8$ are as described herein. In an exemplary embodiment, the compound is according to formula (Ia) and/or (IIa), wherein Y is as described herein, and

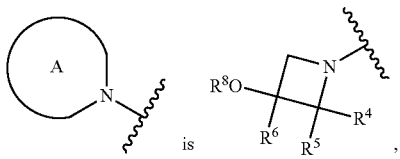

wherein $R^4$ or $R^5$ or $R^8$ are as described herein, $R^8$ is H, and $R^6$ is unsubstituted $C_1$-$C_4$ alkyl or halosubstituted $C_1$-$C_4$ alkyl or unsubstituted $C_3$-$C_5$ cycloalkyl. In an exemplary embodiment, the compound is according to formula (Ia) and/or (IIa), wherein Y is as described herein, and

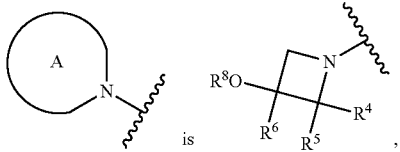

wherein $R^4$ or $R^5$ or $R^8$ are as described herein, and $R^6$ is methyl or ethyl or propyl or isopropyl or trifluoromethyl or difluoromethyl or trifluoroethyl or cyclopropyl. In an exemplary embodiment, the compound is according to formula (Ia) and/or (IIa), wherein Y is as described herein, and

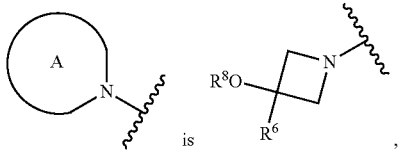

wherein $R^6$ or $R^8$ are as described herein. In an exemplary embodiment, the compound is according to formula (Ia) and/or (IIa), wherein Y is as described herein, and

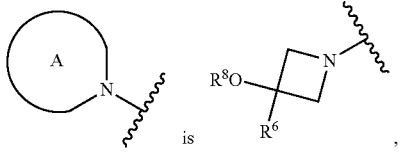

wherein $R^8$ is H and $R^6$ is methyl or ethyl or propyl or isopropyl or trifluoromethyl or difluoromethyl or trifluoroethyl or cyclopropyl.

In an exemplary embodiment, the compound is according to formula (Ia) and/or (IIa), wherein Y is as described herein, and

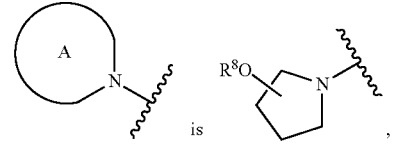

wherein $R^8$ is as described herein. In an exemplary embodiment, the compound is according to formula (Ia) and/or (IIa), wherein Y is as described herein, and

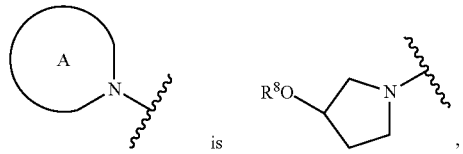

wherein $R^8$ is as described herein. In an exemplary embodiment, the compound is according to formula (Ia) and/or (IIa), wherein Y is as described herein, and

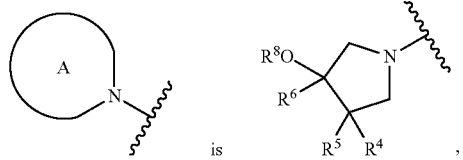

wherein $R^4$ or $R^5$ or $R^6$ or $R^8$ are as described herein.

In an exemplary embodiment, the compound is according to formula (Ia) and/or (IIa), wherein Y is as described herein, and

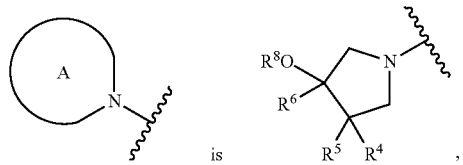

wherein $R^4$ or $R^5$ are as described herein, $R^8$ is H, and $R^6$ is unsubstituted $C_1$-$C_4$ alkyl or halosubstituted $C_1$-$C_4$ alkyl or unsubstituted $C_3$-$C_5$ cycloalkyl, $R^8$ are as described herein. In an exemplary embodiment, the compound is according to formula (Ia) and/or (IIa), wherein Y is as described herein, and

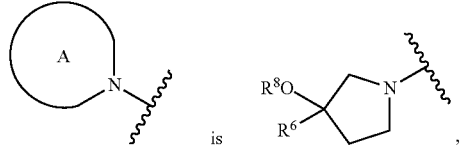

wherein $R^6$ or $R^8$ are as described herein.

In an exemplary embodiment, the compound is according to formula (Ia) and/or (IIa), wherein Y is as described herein, and

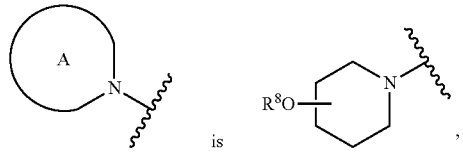

wherein $R^8$ is as described herein. In an exemplary embodiment, the compound is according to formula (Ia) and/or (IIa), wherein Y is as described herein, and

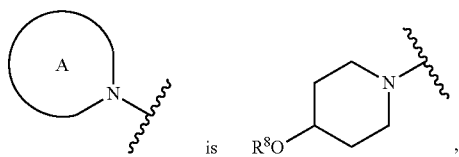 is 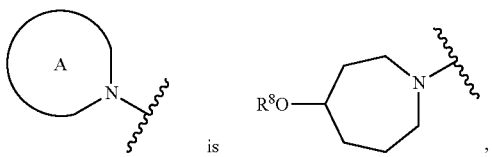, wherein $R^8$ is as described herein. In an exemplary embodiment, the compound is according to formula (Ia) and/or (IIa), wherein Y is as described herein, and

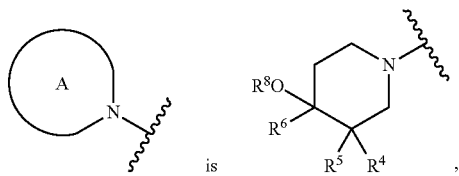 is , wherein $R^4$ or $R^5$ or $R^6$ or $R^8$ are as described herein. In an exemplary embodiment, the compound is according to formula (Ia) and/or (IIa), wherein Y is as described herein, and

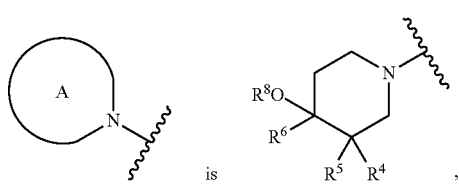 is , wherein $R^4$ or $R^5$ are as described herein, $R^8$ is H, and $R^6$ is unsubstituted $C_1$-$C_4$ alkyl or halosubstituted $C_1$-$C_4$ alkyl or unsubstituted $C_3$-$C_5$ cycloalkyl, $R^8$ are as described herein. In an exemplary embodiment, the compound is according to formula (Ia) and/or (IIa), wherein Y is as described herein, and

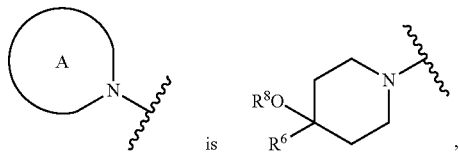 is , wherein $R^6$ or $R^8$ are as described herein.

In an exemplary embodiment, the compound is according to formula (Ia) and/or (IIa), wherein Y is as described herein, and

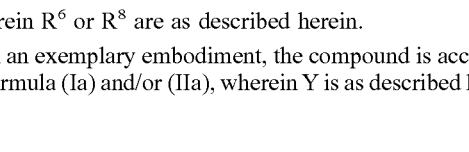 is , wherein $R^8$ is as described herein. In an exemplary embodiment, the compound is according to formula (Ia) and/or (IIa), wherein Y is as described herein, and wherein $R^8$ is as described herein. In an exemplary embodiment, the compound is according to formula (Ia) and/or (IIa), wherein Y is as described herein, and

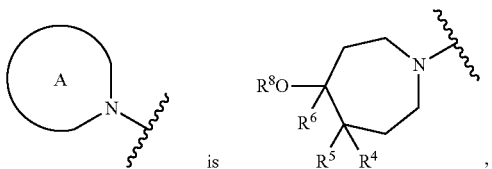 is , wherein $R^4$ or $R^5$ or $R^6$ or $R^8$ are as described herein. In an exemplary embodiment, the compound is according to formula (Ia) and/or (IIa), wherein Y is as described herein, and

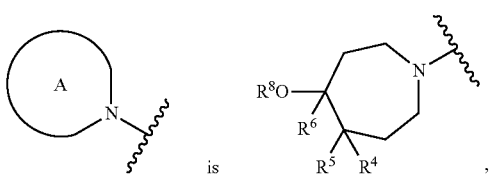 is , wherein $R^4$ or $R^5$ are as described herein, $R^8$ is H, and $R^6$ is unsubstituted $C_1$-$C_4$ alkyl or halosubstituted $C_1$-$C_4$ alkyl or unsubstituted $C_3$-$C_5$ cycloalkyl, $R^8$ are as described herein. In an exemplary embodiment, the compound is according to formula (Ia) and/or (IIa), wherein Y is as described herein, and

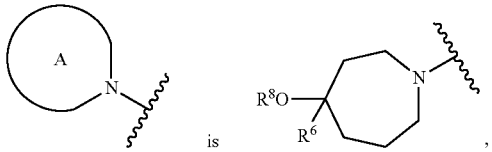 is , wherein $R^6$ or $R^8$ are as described herein.

In an exemplary embodiment, the compound is according to formula (Ia) and/or (IIa), wherein Y is as described herein, and

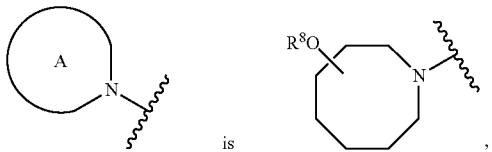 is , wherein $R^8$ is as described herein. In an exemplary embodiment, the compound is according to formula (Ia) and/or (IIa), wherein Y is as described herein, and

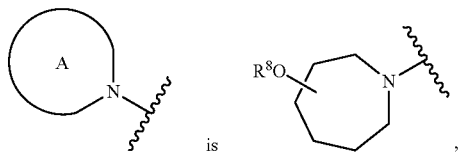

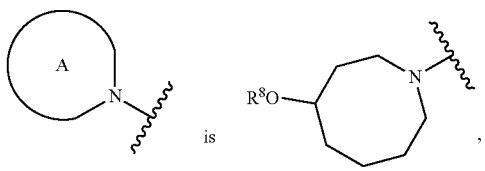

is wherein $R^8$ is as described herein. In an exemplary embodiment, the compound is according to formula (Ia) and/or (IIa), wherein Y is as described herein, and

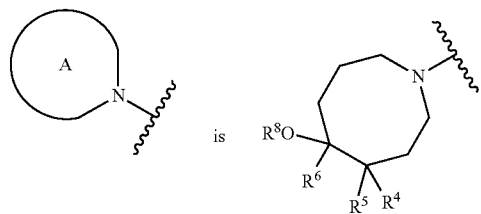

is wherein $R^4$ or $R^5$ or $R^6$ or $R^8$ are as described herein. In an exemplary embodiment, the compound is according to formula (Ia) and/or (IIa), wherein Y is as described herein, and

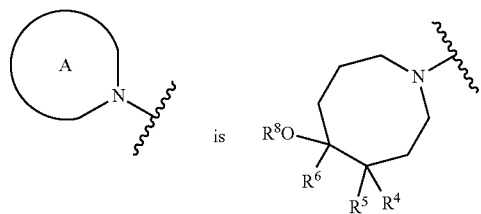

is wherein $R^4$ or $R^5$ are as described herein, $R^8$ is H, and $R^6$ is unsubstituted $C_1$-$C_4$ alkyl or halosubstituted $C_1$-$C_4$ alkyl or unsubstituted $C_3$-$C_5$ cycloalkyl, $R^8$ are as described herein. In an exemplary embodiment, the compound is according to formula (Ia) and/or (IIa), wherein Y is as described herein, and

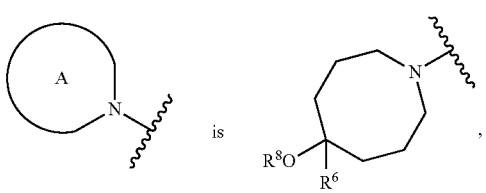

is wherein $R^6$ or $R^8$ are as described herein.

In an exemplary embodiment, the compound is according to formula (Ia) and/or (IIa), wherein Y is as described herein, and

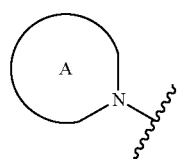

is unsubstituted piperazinyl. In an exemplary embodiment, the compound is according to formula (Ia) and/or (IIa), wherein Y is as described herein, and

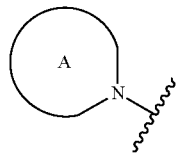

is substituted piperazinyl. In an exemplary embodiment, the compound is according to formula (Ia) and/or (IIa), wherein Y is as described herein, and

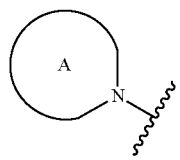

is piperazinyl substituted with a hydroxy$C_1$-$C_6$alkyl.

In an exemplary embodiment, the compound is according to formula (Ia) wherein A is as described herein, and Y is $CH_3$. In an exemplary embodiment, the compound is according to formula (IIa) wherein A is as described herein, and Y is $CH_3$.

In another embodiment, the invention provides a compound having a structure according to formula (Ib) and/or (IIb):

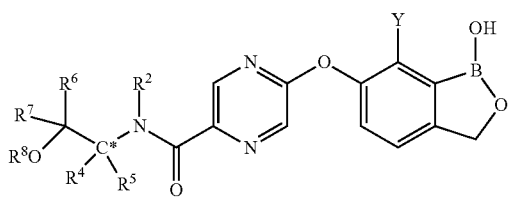

(Ib)

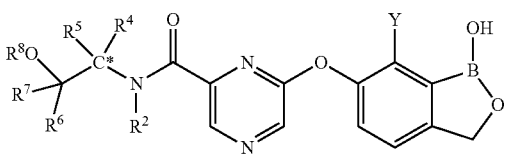

(IIb)

wherein Y, $R^2$, $R^4$, $R^5$, $R^6$, $R^7$, and $R^8$ are as described herein, and C* is a carbon atom which is a stereocenter having a configuration which is (R) or (S). In another embodiment, the compound has a structure according to formula (Ib), wherein Y, $R^2$, $R^4$, $R^5$, $R^6$, $R^7$, and $R^8$ are as described herein, and C* is a stereocenter with an (R) configuration. In another embodiment, the compound has a structure according to formula (Ib), wherein Y, $R^2$, $R^4$, $R^5$, $R^6$, $R^7$, and $R^8$ are as described herein, and C* is a stereocenter with an (S) configuration. In another embodiment, the compound has a structure according to formula (IIb), wherein Y, $R^2$, $R^4$, $R^5$, $R^6$, $R^7$, and $R^8$ are as described herein, and C* is a stereocenter with an (R) configuration. In another embodiment, the compound has a structure according to formula (IIb), wherein Y, $R^2$, $R^4$, $R^5$, $R^6$, $R^7$, and $R^8$ are as described herein, and C* is a stereocenter with an (S) configuration.

In another embodiment, the invention provides a compound having a structure according to formula (Ic) and/or (IIc):

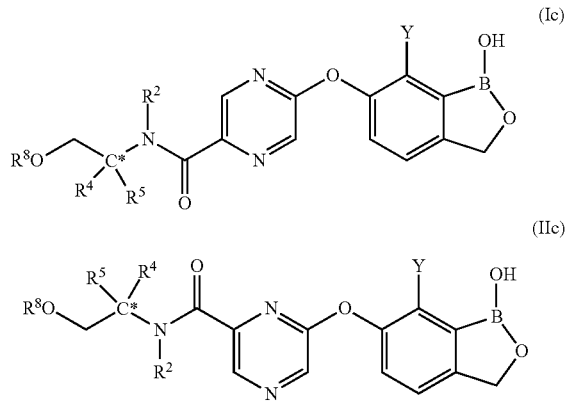

wherein Y, $R^2$, $R^4$, $R^5$, and $R^8$ are as described herein, and C* is a carbon atom which is a stereocenter having a configuration which is (R) or (S). In another embodiment, the compound has a structure according to formula (Ic), wherein Y, $R^2$, $R^4$, $R^5$, and $R^8$ are as described herein, and C* is a stereocenter with an (R) configuration. In another embodiment, the compound has a structure according to formula (Ic), wherein Y, $R^2$, $R^4$, $R^5$, and $R^8$ are as described herein, and C* is a stereocenter with an (S) configuration. In another embodiment, the compound has a structure according to formula (IIc), wherein Y, $R^2$, $R^4$, $R^5$, and $R^8$ are as described herein, and C* is a stereocenter with an (R) configuration. In another embodiment, the compound has a structure according to formula (IIc), wherein Y, $R^2$, $R^4$, $R^5$, and $R^8$ are as described herein, and C* is a stereocenter with an (S) configuration.

In another embodiment, the invention provides a compound having a structure according to formula (Id) and/or (IId):

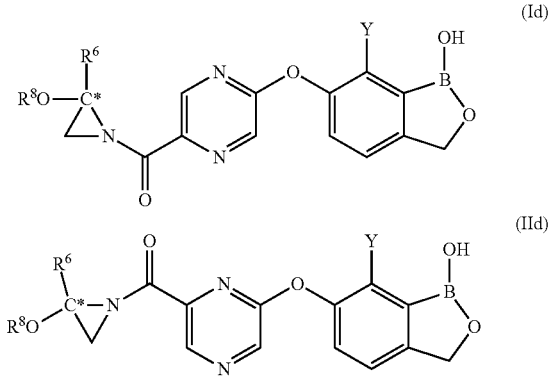

wherein Y, $R^6$, and $R^8$ are as described herein, and C* is a carbon atom which is a stereocenter having a configuration which is (R) or (S). In another embodiment, the compound has a structure according to formula (Id), wherein Y, $R^6$, and $R^8$ are as described herein, and C* is a stereocenter with an (R) configuration. In another embodiment, the compound has a structure according to formula (Id), wherein Y, $R^6$, and $R^8$ are as described herein, and C* is a stereocenter with an (S) configuration. In another embodiment, the compound has a structure according to formula (IId), wherein Y, $R^6$, and $R^8$ are as described herein, and C* is a stereocenter with an (R) configuration. In another embodiment, the compound has a structure according to formula (IId), wherein Y, $R^6$, and $R^8$ are as described herein, and C* is a stereocenter with an (S) configuration.

In another embodiment, the invention provides a compound having a structure according to formula (Ie) and/or (IIe) and/or (If) and/or (IIf):

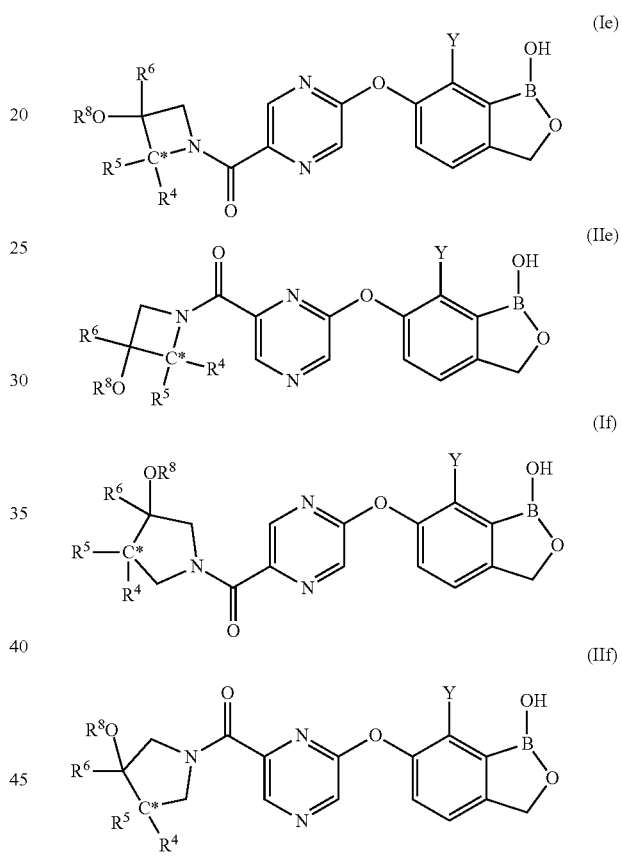

wherein Y, $R^2$, $R^4$, $R^5$, $R^6$, and $R^8$ are as described herein, and C* is a carbon atom which is a stereocenter having a configuration which is (R) or (S). In another embodiment, the compound has a structure according to formula (Ie), wherein Y, $R^2$, $R^4$, $R^5$, $R^6$, and $R^8$ are as described herein, and C* is a stereocenter with an (R) configuration. In another embodiment, the compound has a structure according to formula (Ie), wherein Y, $R^2$, $R^4$, $R^5$, $R^6$, and $R^8$ are as described herein, and C* is a stereocenter with an (S) configuration. In another embodiment, the compound has a structure according to formula (Iie), wherein Y, $R^2$, $R^4$, $R^5$, $R^6$, and $R^8$ are as described herein, and C* is a stereocenter with an (R) configuration. In another embodiment, the compound has a structure according to formula (IIe), wherein Y, $R^2$, $R^4$, $R^5$, $R^6$, and $R^8$ are as described herein, and C* is a stereocenter with an (S) configuration. In another embodiment, the compound has a structure according to formula (If), wherein Y, $R^2$, $R^4$, $R^5$, $R^6$, and $R^8$ are as described herein, and C* is a stereocenter with an (R) configuration. In another embodiment, the compound has a structure according to formula (If), wherein Y, $R^2$, $R^4$, $R^5$, $R^6$, and $R^8$ are as described herein, and C* is a stereocenter with an (S) configuration. In another embodiment, the compound has a structure according to formula (IIf), wherein Y, $R^2$, $R^4$, $R^5$, $R^6$, and $R^8$ are as described herein, and C* is a stereocenter with an (R) configuration. In another embodiment, the compound has a structure according to formula (IIf), wherein Y, $R^2$, $R^4$, $R^5$, $R^6$, and $R^8$ are as described herein, and C* is a stereocenter with an (S) configuration.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

III.b) Compositions Involving Stereoisomers

As used herein, the term "chiral", "enantiomerically enriched" or "diastereomerically enriched" refers to a composition having an enantiomeric excess (ee) or a diastereomeric excess (de) of greater than about 50%, preferably greater than about 70% and more preferably greater than about 90%. In general, higher than about 90% enantiomeric or diastereomeric excess is particularly preferred, e.g., those compositions with greater than about 95%, greater than about 97% and greater than about 99% ee or de.

When a first compound and a second compound are present in a composition, and the first compound is a non-superimposable mirror image of the second compound, and the first compound is present in the composition in a greater amount than the second compound, then the first compound is referred to herein as being present in "enantiomeric excess".

The term "enantiomeric excess" of a compound z, as used herein, is defined as:

$$ee_z = \left(\frac{conc.\ of\ z - conc.\ of\ y}{conc.\ of\ z + conc.\ of\ y}\right) \times 100$$

wherein z is a first compound in a composition, y is a second compound in the composition, and the first compound is a non-superimposable mirror image of the second compound.

The term "enantiomeric excess" is related to the older term "optical purity" in that both are measures of the same phenomenon. The value of ee will be a number from 0 to 100, zero being racemic and 100 being enantiomerically pure. A composition which in the past might have been called 98% optically pure is now more precisely characterized by 96% ee. A 90% ee reflects the presence of 95% of one enantiomer and 5% of the other(s) in the material in question.

When a first compound and at least one additional compound are present in a composition, and the first compound and each of the additional compounds are stereoisomers, but not mirror images, of one another, and the first compound is present in the composition in a greater amount than each of the additional compounds, then the first compound is referred to herein as being present in "diastereomeric excess".

When dealing with mixtures of diastereomers, the term "diastereomeric excess" or "de" is defined analogously to enantiomeric excess. Thus:

$$de_w = \left(\frac{conc.\ of\ major\ diastereomer - conc.\ of\ min\ or\ diastereomer(s)}{conc.\ of\ major\ diastereomer + conc.\ of\ min\ or\ diastereomer(s)}\right) \times 100$$

wherein the major diastereomer is a first compound in a composition, and the minor diastereomer(s) is at least one additional compound in the composition, and the major diastereomer and minor diastereomer(s) are stereoisomers, but not mirror images, of one another.

The value of de will likewise be a number from 0 to 100, zero being an equal mixture of a first diastereomer and the remaining diastereomer(s), and 100 being 100% of a single diastereomer and zero % of the other(s)—i.e. diastereomerically pure. Thus, 90% de reflects the presence of 95% of one diastereomer and 5% of the other diastereomer(s) in the material in question.

Hence, in one embodiment, the invention provides a composition including a first compound of the invention, wherein the first compound of the invention has at least one stereocenter, and at least one stereoisomer of the first compound of the invention. In another embodiment, the invention provides a composition including a first compound of the invention, wherein the first compound of the invention has at least one stereocenter, and a second compound of the invention, wherein the first compound of the invention is a stereoisomer of the second compound of the invention. In another embodiment, the invention provides a composition including a first compound of the invention, wherein the first compound of the invention has at least one stereocenter, and only one stereoisomer of the first compound of the invention.

In another embodiment, the invention provides a composition including a first compound of the invention, wherein the first compound of the invention has only one stereocenter, and an enantiomer of the first compound of the invention. In another embodiment, the invention provides a composition including a first compound of the invention, wherein the first compound of the invention has two stereocenters, and an enantiomer of the first compound of the invention. In another embodiment, the invention provides a composition including a first compound of the invention, wherein the first compound of the invention has two stereocenters, and at least one diastereomer of the first compound of the invention. In another embodiment, the invention provides a composition including a first compound of the invention, wherein the first compound of the invention has two stereocenters, and only one diastereomer of the first compound of the invention.

In situations where the first compound of the invention and its enantiomer are present in a composition, the first compound of the invention can be present in an enantiomeric excess of at least about 80%, or at least about 90%, or at least about 92% or at least about 95%. In another embodiment, where the first compound of the invention and its enantiomer are present in a composition, the first compound of the invention can be present in an enantiomeric excess of at least about 96%, at least about 97%, at least about 98%, at least about 99% or at least about 99.5%. In another embodiment, the first compound of the invention has at least one stereocenter and is enantiomerically pure (enantiomeric excess is about 100%).

In situations where the first compound of the invention and at least one diastereomer of the first compound of the invention are present in a composition, the first compound of the invention can be present in a diastereomeric excess of at least about 80%, or at least about 90%, or at least about 92% or at least about 95%. In situations where the first compound of the invention and at least one diastereomer of the first compound of the invention are present in a composition, the first compound of the invention can be present in a diastereomeric excess of at least about 96%, at least about 97%, at least about 98%, at least about 99% or at least about 99.5%. In another embodiment, the first compound of the invention has at least two stereocenters and is diastereomerically pure (diastereomeric excess is about 100%).

Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

As used herein, and unless otherwise indicated, a composition that is "substantially free" of a compound means that the composition contains less than about 20% by weight, or less than about 15% by weight, or less than about 10% by weight, or less than about 5% by weight, or less than about 3% by weight, or less than about 2% by weight, or less than about 1% by weight of the compound.

As used herein, the term "substantially free of the (or its) enantiomer" means that a composition contains a significantly greater proportion of a first compound of the invention than a second compound of the invention, wherein the first compound is a non-superimposable mirror image of the second compound. In one embodiment of the invention, the term "substantially free of the enantiomer" means that the composition is made up of at least about 90% by weight of a first compound of the invention, and about 10% by weight or less of a second compound of the invention, wherein the first compound is a non-superimposable mirror image of the second compound. In one embodiment of the invention, the term "substantially free of the (R) enantiomer" means that the composition is made up of at least about 90% by weight of a first compound of the invention which has only one stereocenter and the stereocenter is in an (S) configuration, and about 10% by weight or less of a second compound of the invention, wherein the second compound is the enantiomer of the first compound. In one embodiment of the invention, the term "substantially free of the enantiomer" means that the composition is made up of at least about 95% by weight of a first compound of the invention, and about 5% by weight or less of a second compound of the invention, wherein the first compound is a non-superimposable mirror image of the second compound. In one embodiment of the invention, the term "substantially free of the (R) enantiomer" means that the composition is made up of at least about 95% by weight of a first compound of the invention which has only one stereocenter and the stereocenter is in an (S) configuration, and about 5% by weight or less of a second compound of the invention, wherein the second compound is the enantiomer of the first compound. In one embodiment of the invention, the term "substantially free of the enantiomer" means that the composition is made up of at least about 98% by weight of a first compound of the invention, and about 2% by weight or less of a second compound of the invention, wherein the first compound is a non-superimposable mirror image of the second compound. In one embodiment of the invention, the term "substantially free of the (R) enantiomer" means that the composition is made up of at least about 98% by weight of a first compound of the invention which has only one stereocenter and the stereocenter is in an (S) configuration, and about 2% by weight or less of a second compound of the invention, wherein the second compound is the enantiomer of the first compound. In one embodiment of the invention, the term "substantially free of the enantiomer" means that the composition is made up of at least about 99% by weight of a first compound of the invention, and about 1% by weight or less of a second compound of the invention, wherein the first compound is a non-superimposable mirror image of the second compound. In one embodiment of the invention, the term "substantially free of the (R) enantiomer" means that the composition is made up of at least about 99% by weight of a first compound of the invention which has only one stereocenter and the stereocenter is in an (S) configuration, and about 1% by weight or less of a second compound of the invention, wherein the second compound is the enantiomer of the first compound.

In an exemplary embodiment, the invention provides a composition comprising a) first compound described herein; and b) the enantiomer of the first compound, wherein the first compound described herein is present in an enantiomeric excess of at least 80%. In an exemplary embodiment, the enantiomeric excess is at least 92%.

III.c) Combinations Comprising Additional Therapeutic Agents

The compounds of the invention may also be used in combination with additional therapeutic agents. The invention thus provides, in a further aspect, a combination comprising a compound of the invention together with at least one additional therapeutic agent. In an exemplary embodiment, the combination comprises a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom. In an exemplary embodiment, the combination comprises: a) a compound of the invention and b) a first additional therapeutic agent. In an exemplary embodiment, the combination comprises: a) a compound of the invention; b) a first additional therapeutic agent; and c) a second additional therapeutic agent. In an exemplary embodiment, the combination comprises: a)

compound of the invention; b) a first additional therapeutic agent; c) a second additional therapeutic agent; and d) a third additional therapeutic agent.

When a compound of the invention is used in combination with at least one additional therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. In an exemplary embodiment, the additional therapeutic agent is berenil. In an exemplary embodiment, the additional therapeutic agent is diminazene. In an exemplary embodiment, the additional therapeutic agent is an antiprotozoal. In an exemplary embodiment, the additional therapeutic agent is selected from the group consisting of benznidazole, buparvaquone, carbarsone, clioquinol, disulfiram, eflornithine, emetine, etofamide, furazolidone, meglumine antimoniate, melarsoprol, metronidazole, miltefosine, nifurtimox, nimorazole, nitazoxanide, ornidazole, paromomycin sulfate, pentamidine, pyrimethamine, secnidazole and tinidazole. In an exemplary embodiment, the additional therapeutic agent is pentamidine. In an exemplary embodiment, the additional therapeutic agent is suramin. In an exemplary embodiment, the additional therapeutic agent is eflornithine. In an exemplary embodiment, the additional therapeutic agent is melarsoprol. In an exemplary embodiment, the additional therapeutic agent is nifurtimox. In an exemplary embodiment, the additional therapeutic agent contains a 5-nitrofuran moiety. In an exemplary embodiment, the additional therapeutic agent contains a 5-nitroimidazolyl moiety. In an exemplary embodiment, the additional therapeutic agent is fexinidazole. In an exemplary embodiment, the additional therapeutic agent is an antiparasitic. In an exemplary embodiment, the additional therapeutic agent is selected from the group consisting of amitraz, avermectin, carbadox, diethylcarbamazine, dimetridazole, diminazene, ivermectin, macrofilaricide, malathion, mitaban, organophosphate, oxamniquine, permethrin, praziquantel, pyrantel pamoate, selamectin, sodium stibogluconate and thiabendazole. In an exemplary embodiment, the additional therapeutic agent is selected from the group consisting of antimony, meglumine antimoniate, sodium stibogluconate, amphotericin, miltefosine and paromomycin.

In an exemplary embodiment, the additional therapeutic agent is an antimalarial. In an exemplary embodiment, the additional therapeutic agent is artemisinin. In an exemplary embodiment, the additional therapeutic agent is an artemisinin derivative. In an exemplary embodiment, the additional therapeutic agent is an artemisinin derivative which is artesunate or artemether or artemotil or dihydroartemisinin. In an exemplary embodiment, the additional therapeutic agent is a member selected from lumefantrine, artemether-lumefantrine, amodiaquine, artesunate-amodiaquine, artesunate-mefloquine, artesunate-sulfadoxine/pyrimethamine, atovaquone-proguanil, quinine, chloroquine, cotrifazid, doxycycline, mefloquine, primaquine, proguanil, sulfadoxine-pyrimethamine, hydroxychloroquine, sulfalene-pyrimethamine, dapsone, proguanil-dapsone and chloroproguanil-dapsone. In an exemplary embodiment, the additional therapeutic agent is a member selected from amodiaquine, chloroquine and sulfadoxine-pyrimethamine. In an exemplary embodiment, the additional therapeutic agent is mefloquine. In an exemplary embodiment, the additional therapeutic agent is a member selected from halofantrine, dihydroartemisinin-piperaquine, piperaquine, pyronaridine and tetracycline.

The compounds of the invention, or pharmaceutical formulations thereof may also be used in combination with other therapeutic agents, for example immune therapies [e.g. interferon, such as interferon alfa-2a (ROFERON®-A; Hoffmann-La Roche), interferon alpha-2b (INTRON®-A; Schering-Plough), interferon alfacon-1 (INFERGEN®; Intermune), peginterferon alpha-2b (PEGINTRON™; Schering-Plough) or peginterferon alpha-2a (PEGASYS®; Hoffmann-La Roche)], therapeutic vaccines, antifibrotic agents, anti-inflammatory agents [such as corticosteroids or NSAIDs], bronchodilators [such as beta-2 adrenergic agonists and xanthines (e.g. theophylline)], mucolytic agents, anti-muscarinics, anti-leukotrienes, inhibitors of cell adhesion [e.g. ICAM antagonists], anti-oxidants [e.g. N-acetylcysteine], cytokine agonists, cytokine antagonists, lung surfactants and/or antimicrobial. The compositions according to the invention may also be used in combination with gene replacement therapy.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

It is to be understood that the invention covers all combinations of aspects and/or embodiments, as well as suitable, convenient and preferred groups described herein.

III.d) Preparation of Boron-Containing Compounds

Compounds of use in the invention can be prepared using commercially available starting materials, known intermediates, or by using the synthetic methods described herein, or published in references described and incorporated by reference herein, such as U.S. Prov. Pat. App. 60/654,060; Filed Feb. 16, 2005 ; U.S. patent application Ser. No. 11/357,687, Filed Feb. 16, 2006 ; U.S. patent application Ser. No. 11/505,591, Filed Aug. 16, 2006, U.S. Prov. Pat. App. 60/823,888 filed on Aug. 29, 2006 and 60/774,532 filed on Feb. 16, 2006; U.S. patent application Ser. No. 11/676,120, Filed Feb. 16, 2007; U.S. patent application Ser. No. 12/142,692, Filed Jun. 19, 2008; U.S. patent application Ser. No. 12/399,015, Filed Mar. 5, 2009; U.S. patent application Ser. No. 12/464,829, Filed May 12, 2009; which are herein incorporated by reference in their entirety for all purposes. Methods of producing the compounds of the invention are also described in these patent applications.

The compounds in this invention can be prepared as shown in the reaction schemes below.

In an aspect of the invention, compounds of the invention can be synthesized according to at least one of the following schemes:

General Synthetic Scheme:

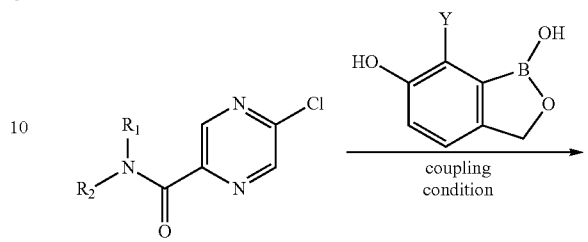

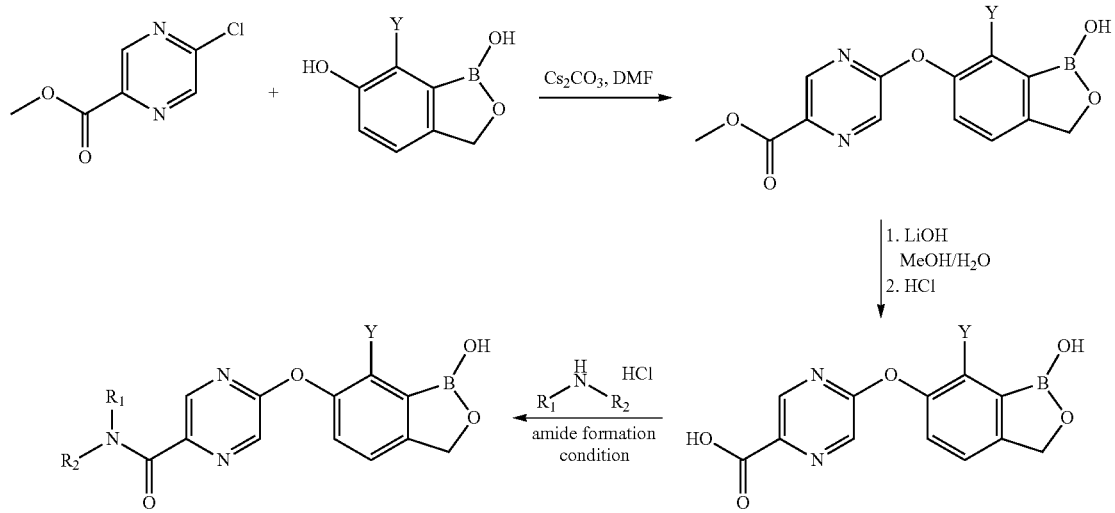

Alternative General Synthetic Scheme:

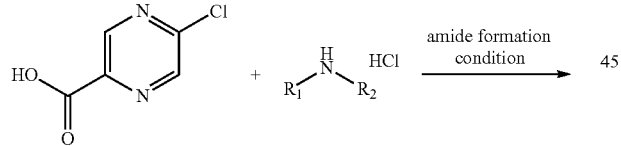

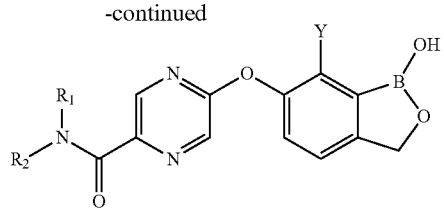

General Synthetic Scheme:

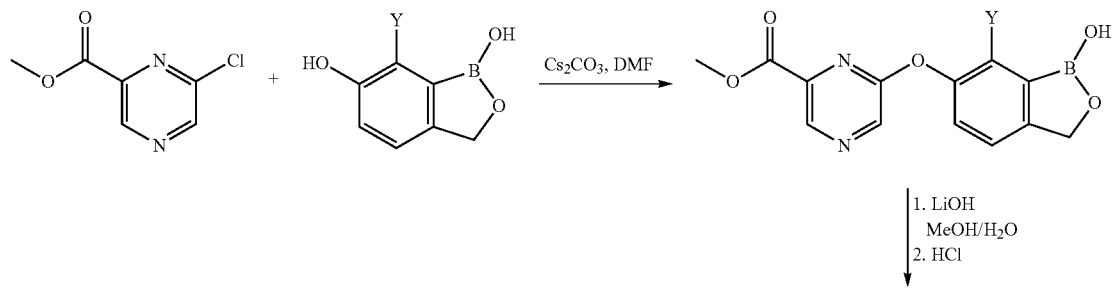

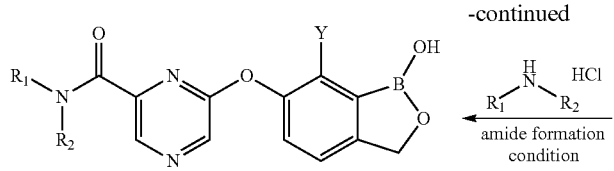 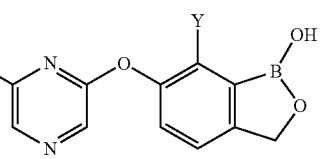

Alternative General Synthetic Scheme:

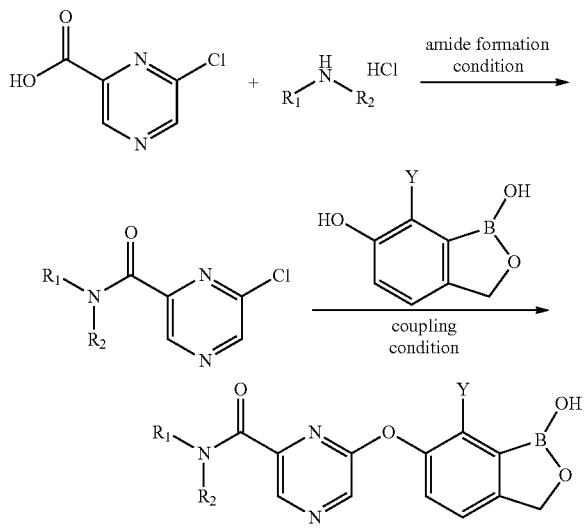

General Synthetic Scheme:

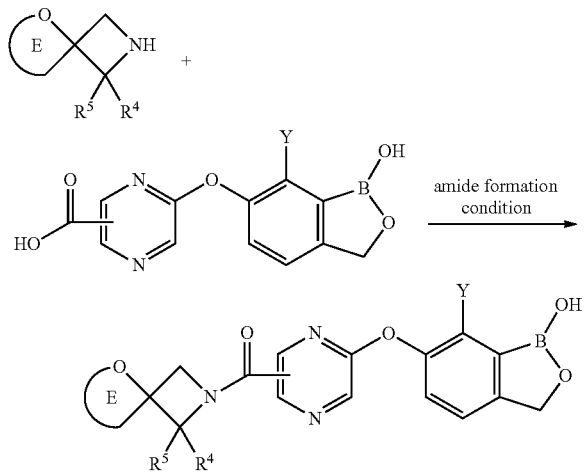

wherein the E-ring is substituted or unsubstituted cycloalkoxy (ring sizes from 3 to 8).

General Synthetic Scheme:

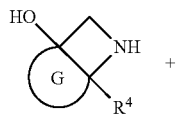

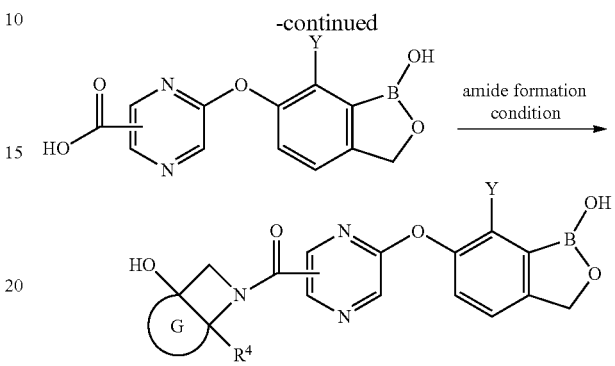

wherein the G-ring is substituted or unsubstituted cycloalkyl (ring sizes from 3 to 8).

Compounds described herein can be converted into hydrates and solvates by methods similar to those described herein.

IV. Methods of Inhibiting Microorganism Growth or Killing Microorganisms

The compounds of the invention exhibit potency against microorganisms, such as protozoa, and therefore have the potential to kill and/or inhibit the growth of microorganisms.

In a further aspect, the invention provides a method of killing and/or inhibiting the growth of a microorganism, said method comprising: contacting said microorganism with an effective amount of a compound of the invention, thereby killing and/or inhibiting the growth of the microorganism. In an exemplary embodiment, the microorganism is a protozoa. In an exemplary embodiment, the microorganism is a kinetoplastid. In another exemplary embodiment, the protozoa is a *Trypanosoma*. In an exemplary embodiment, the *Trypanosoma* is a member selected from *T. avium, T. boissoni, T. brucei, T. carassii, T. cruzi, T. congolense, T equinum, T. equiperdum, T. evansi, T. hosei, T. levisi, T. melophagium, T. parroti, T percae, T. rangeli, T. rotatorium, T. rugosae, T. sergenti, T. simiae, T. sinipercae, T suis, T. theileri, T. triglae* and *T. vivax*. In another exemplary embodiment, the protozoa is a *Trypanosoma brucei*. In another exemplary embodiment, the protozoa is a member selected from *Trypanosoma brucei brucei, Trypanosoma brucei* rhodesiense and *Trypanosoma brucei* gambiense. In another exemplary embodiment, the protozoa is a member selected from *Trypanosoma brucei* rhodesiense and *Trypanosoma brucei* gambiense. In another exemplary embodiment, the protozoa is *Trypanosoma cruzi*. In another exemplary embodiment, the protozoa is a member of the genus *Leishmania*. In another exemplary embodiment, the protozoa is a member of *Leishmania* Viannia. In an exemplary embodiment, the protozoa is a member selected from *L. donovani, L. infantum, L. chagasi; L. mexicana, L. amazonensis, L. venezuelensis, L. tropica, L. major, L. aethiopica, L. (V.) braziliensis, L. (V.) guyanensis, L. (V) panamensis*, and *L. (V.) peruviana*. In an exemplary embodiment, the protozoa is *L. donovani*. In an exemplary embodiment, the protozoa is *L. infantum*. In another exemplary embodiment, the protozoa is a member of the genus

*Plasmodium*. In another exemplary embodiment, the protozoa is a member selected from *Plasmodium falciparum, Plasmodium vivax, Plasmodium ovale, Plasmodium vivax, Plasmodium malariae* and *Plasmodium knowlesi*. In another exemplary embodiment, the protozoa is *Plasmodium vivax*. In another exemplary embodiment, the protozoa is *Plasmodium ovale*. In another exemplary embodiment, the protozoa is *Plasmodium malariae*. In another exemplary embodiment, the protozoa is *Plasmodium falciparum*. In another exemplary embodiment, the protozoa is transmitted to the animal described herein by a mosquito infected with the protozoa. In another exemplary embodiment, wherein the protozoa is transmitted to the animal described herein by an *Anopheles* mosquito containing the protozoa. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another aspect, the microorganism is inside, or on the surface of an animal. In an exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism is killed or its growth is inhibited through oral administration of the compound of the invention. In an exemplary embodiment, the microorganism is killed or its growth is inhibited through intravenous administration of the compound of the invention. In an exemplary embodiment, the microorganism is killed or its growth is inhibited through topical administration of the compound of the invention. In an exemplary embodiment, the microorganism is killed or its growth is inhibited through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

V. Methods of Treating and/or Preventing Disease

The compounds of the invention exhibit potency against microorganisms, such as protozoa, and therefore have the potential to achieve therapeutic efficacy in the animals described herein.

In another aspect, the invention provides a method of treating and/or preventing a disease. The method includes administering to the animal a therapeutically effective amount of the compound of the invention, sufficient to treat and/or prevent the disease. In another aspect, the invention provides a method of treating a disease in an animal comprising administering to the animal a therapeutically effective amount of the compound of the invention, wherein the animal is in need of treatment, sufficient to treat the disease. In another aspect, the invention provides a method of treating a disease in an animal comprising administering to the animal a therapeutically effective amount of the compound of the invention, wherein the animal is not otherwise in need of treatment with the compound of the invention, sufficient to treat the disease. In another aspect, the invention provides a method of preventing a disease in an animal comprising administering to the animal a therapeutically effective amount of the compound of the invention, sufficient to prevent the disease. In an exemplary embodiment, the compound of the invention can be used in human or veterinary medical therapy, particularly in the treatment or prophylaxis of protozoa-associated disease. In an exemplary embodiment, the compound of the invention can be used in human or veterinary medical therapy, particularly in the treatment or prophylaxis of kinetoplastid-associated disease. In an exemplary embodiment, the disease is associated with a *Trypanosoma*. In an exemplary embodiment, the *Trypanosoma* is a member selected from *T. avium, T. boissoni, T. brucei, T. carassii, T. cruzi, T. congolense, T. equinum, T. equiperdum, T. evansi, T. hosei, T. levisi, T. melophagium, T. parroti, T. percae, T. rangeli, T. rotatorium, T. rugosae, T. sergenti, T. simiae, T. sinipercae, T. suis, T. theileri, T. triglae* and *T. vivax*. In an exemplary embodiment, the disease is associated with a *Trypanosoma brucei*. In an exemplary embodiment, the disease is associated with a member selected from *Trypanosoma brucei brucei, Trypanosoma brucei* rhodesiense and *Trypanosoma brucei* gambiense. In an exemplary embodiment, the disease is associated with *Trypanosoma brucei* rhodesiense. In an exemplary embodiment, the disease is associated with *Trypanosoma brucei* gambiense. In an exemplary embodiment, the disease is associated with *Trypanosoma cruzi*. In an exemplary embodiment, the disease is a trypanosomiasis. In an exemplary embodiment, the disease is a human trypanosomiasis. In an exemplary embodiment, the disease is an animal trypanosomiasis. In an exemplary embodiment, the disease is a member selected from nagana, surra, mal de caderas, murrina de caderas, dourine, cachexial fevers, Gambian horse sickness, baleri, kaodzera, tahaga, galziekte or galzietzke and peste-boba. In an exemplary embodiment, the disease is a member selected from Chagas disease (or Human American trypanosomiasis), nagana, surra, Covering sickness (or dourine) and sleeping sickness (or African sleeping sickness or Human African trypanosomiasis). In an exemplary embodiment, the disease is Chagas disease. In an exemplary embodiment, the disease is sleeping sickness (or African sleeping sickness). In an exemplary embodiment, the disease is acute phase sleeping sickness. In an exemplary embodiment, the disease is chronic phase sleeping sickness. In an exemplary embodiment, the disease is an acute phase of a trypanosomiasis. In an exemplary embodiment, the disease is a chronic phase of a trypanosomiasis. In an exemplary embodiment, the disease is the non-CNS form of a trypanosomiasis. In an exemplary embodiment, the disease is the CNS form of a trypanosomiasis. In an exemplary embodiment, the disease is the non-CNS form of sleeping sickness. In an exemplary embodiment, the disease is the CNS form of sleeping sickness. In an exemplary embodiment, the disease is early stage Human African trypanosomiasis. In an exemplary embodiment, the disease is late stage Human African trypanosomiasis. In another exemplary embodiment, the disease is associated with a member of the genus *Leishmania*. In another exemplary embodiment, the disease is associated with a member of *Leishmania* Viannia. In an exemplary embodiment, the disease is associated with a member selected from *L. donovani, L. infantum, L. chagasi; L. mexicana, L. amazonensis, L. venezuelensis, L. tropica, L. major, L. aethiopica, L. (V.) braziliensis, L. (V.) guyanensis, L. (V.) panamensis*, and *L. (V.) peruviana*. In an exemplary embodiment, the disease is associated with *L. donovani*. In an exemplary embodiment, the disease is associated with *L. infantum*. In an exemplary embodiment, the disease is leishmaniasis. In an exemplary embodiment, the disease is visceral leishmaniasis. In an exemplary embodiment, the disease is cutaneous leishmaniasis. In an exemplary embodiment, the disease is diffuse cutaneous leishmaniasis and/or mucocutaneous leishmaniasis. In another exemplary embodiment, the disease is associated with a member of the genus *Plasmodium*. In another exemplary embodiment, the disease is associated with a member selected from *Plasmodium falciparum, Plasmodium vivax, Plasmodium ovale, Plasmodium vivax, Plasmodium malariae* and *Plasmodium knowlesi*. In another exemplary embodiment, the disease is associated with a member selected from *Plasmodium vivax, Plasmodium ovale, Plasmodium vivax* and *Plasmodium malariae*. In another exemplary embodiment, the disease is associated with *Plasmodium falciparum*. In another exemplary embodiment, the disease is transmitted to the animal described herein by a mosquito infected with the protozoa. In another exemplary embodiment, the disease is transmitted to the animal described herein by an *Anopheles* mosquito containing the protozoa. In another exemplary embodiment, the disease is malaria. In another exemplary embodiment, the disease is cerebral malaria. In another exemplary embodiment, the disease is chronic malaria. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a mouse. In another exemplary embodiment, the animal is a member selected from a human, cattle, goat, pig, sheep, horse, cow, bull, dog, guinea pig, gerbil, rabbit, cat, chicken and turkey. In another exemplary embodiment, the animal is a human.

In an exemplary embodiment, the disease is treated through oral administration of the compound of the invention. In an exemplary embodiment, the disease is treated through intravenous administration of the compound of the invention. In an exemplary embodiment, the disease is treated through topical administration of the compound of the invention. In an exemplary embodiment, the disease is treated through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

In an exemplary embodiment, the disease is associated with an infection by a microorganism described herein. In an exemplary embodiment, the disease is associated with an infection by a protozoa described herein.

VI. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another exemplary embodiment, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered in a topically effective dose. In an exemplary embodiment, the pharmaceutical formulation is administered in a cosmetically effective dose. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

VI. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat*. B677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

VI. b) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of protozoa cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain protozoa cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m²/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

Exemplary embodiments are summarized herein below.

In an exemplary embodiment, the invention is a compound having a structure according to formula (I) and/or (II):

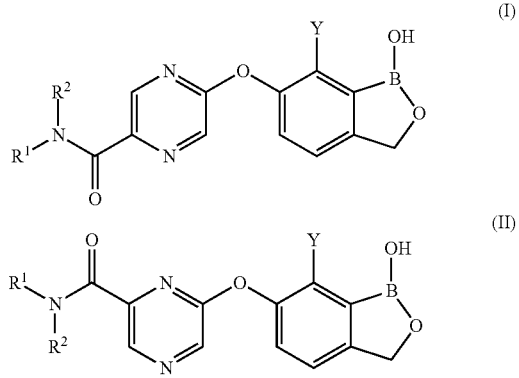

wherein Y is substituted or unsubstituted $C_1$-$C_3$ alkyl or substituted or unsubstituted $C_1$-$C_3$ alkyloxy, and $R^1$ and $R^2$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^1$ and $R^2$, along with the nitrogen to which they are attached, can be optionally joined to form a substituted or unsubstituted 3 to 8 membered ring, or a salt, or a hydrate, or a solvate thereof.

In an exemplary embodiment, according to the above paragraph, $R^1$ is according to formula (III):

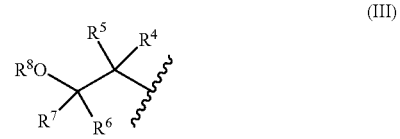

wherein $R^8$ is H or substituted or unsubstituted alkyl, and $R^4$ or $R^5$ or $R^6$ or $R^7$ are each independently selected from H, substituted or unsubstituted $C_1$-$C_6$ alkyl, substituted or unsubstituted heteroalkyl, substituted or unsubstituted $C_3$-$C_8$ cycloalkyl, substituted or unsubstituted aryl, or substituted or unsubstituted heteroaryl, and wherein $R^4$ and $R^5$, along with the atoms to which they are attached, can be optionally joined to form a substituted or unsubstituted 3 to 8 membered ring, and wherein $R^7$ and $R^8$, along with the atoms to which they are attached, can be optionally joined to form a substituted or unsubstituted 3 to 8 membered ring, and wherein $R^5$ and $R^6$, along with the atoms to which they are attached, can be optionally joined to form a substituted or unsubstituted 3 to 8 membered ring.

In an exemplary embodiment, according to any of the above paragraphs, the compound has a structure according to formula (Ia) and/or (IIa):

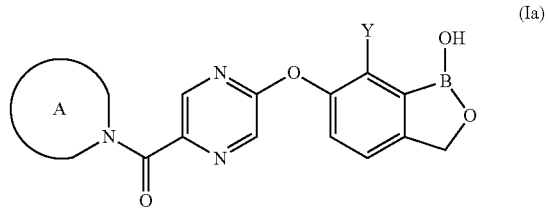

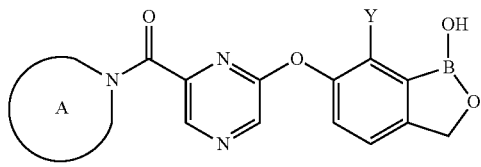

(IIa)

wherein A is a substituted or unsubstituted 3 to 8 membered ring.

In an exemplary embodiment, the invention provides a combination comprising the compound according to any of the above paragraphs, together with at least one additional therapeutic agent.

In an exemplary embodiment, the invention provides a pharmaceutical formulation comprising: a) the compound according to any of the above paragraphs, or a salt thereof; and b) a pharmaceutically acceptable excipient.

In an exemplary embodiment, according to any of the above paragraphs, the pharmaceutical formulation is a unit dosage form.

In an exemplary embodiment, according to any of the above paragraphs, the salt of the compound according to any of the above paragraphs is a pharmaceutically acceptable salt.

In an exemplary embodiment, the invention provides a method of killing and/or preventing the growth of a protozoa, comprising: contacting the protozoa with an effective amount of the compound of the invention, thereby killing and/or preventing the growth of the protozoa.

In an exemplary embodiment, according to any of the above paragraphs, the protozoa is a member of the trypanosome genus.

In an exemplary embodiment, according to any of the above paragraphs, the protozoa is a member of the *leishmania* genus.

In an exemplary embodiment, according to any of the above paragraphs, the protozoa is a member of the *plasmodium* genus.

In an exemplary embodiment, according to any of the above paragraphs, the protozoa is *Trypanosoma brucei*.

In an exemplary embodiment, according to any of the above paragraphs, the *Trypanosoma brucei* is a member selected from *Trypanosoma brucei brucei*, *Trypanosoma brucei* gambiense and *Trypanosoma brucei* rhodesiense.

In an exemplary embodiment, according to any of the above paragraphs, the protozoa is a member selected from *Leishmania donovani, Leishmania infantum, Leishmania chagasi, Leishmania mexicana, Leishmania amazonensis, Leishmania venezuelensis, Leishmania tropica, Leishmania major, Leishmania aethiopica*.

In an exemplary embodiment, according to any of the above paragraphs, the protozoa is *Leishmania donovani*.

In an exemplary embodiment, according to any of the above paragraphs, the protozoa is a member selected from *Plasmodium falciparum, Plasmodium vivax, Plasmodium ovale, Plasmodium vivax, Plasmodium malariae* and *Plasmodium knowlesi*.

In another exemplary embodiment, according to any of the above paragraphs, the protozoa is *Plasmodium falciparum*.

In an exemplary embodiment, the invention provides a method of treating and/or preventing a disease in an animal, comprising: administering to the animal a therapeutically effective amount of the compound of the invention, thereby treating and/or preventing the disease.

In an exemplary embodiment, according to any of the above paragraphs, the disease is African sleeping sickness.

In an exemplary embodiment, according to any of the above paragraphs, the disease is leishmaniasis.

In an exemplary embodiment, according to any of the above paragraphs, the leishmaniasis is a member selected from visceral leishmaniasis, cutaneous leishmaniasis, diffuse cutaneous leishmaniasis and mucocutaneous leishmaniasis.

In an exemplary embodiment, according to any of the above paragraphs, the leishmaniasis is visceral leishmaniasis.

In an exemplary embodiment, according to any of the above paragraphs, the leishmaniasis is cutaneous leishmaniasis.

In an exemplary embodiment, according to any of the above paragraphs, the disease is malaria.

In an exemplary embodiment, according to any of the above paragraphs, the disease is cerebral malaria.

In an exemplary embodiment, according to any of the above paragraphs, the animal is a human.

In an exemplary embodiment, according to any of the above paragraphs, the invention is a use of a compound of the invention or a combination of the invention in the manufacture of a medicament for the treatment and/or prophylaxis of protozoal infection.

The invention is further illustrated by the Examples that follow. The Examples are not intended to define or limit the scope of the invention.

EXAMPLES

The following Examples illustrate the synthesis of representative compounds used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

All temperatures are given in degrees Centigrade. Room temperature means 20 to 25° C. Reagents were purchased from commercial sources or prepared following standard literature procedures. Unless otherwise noted, reactions were carried out under a positive pressure of nitrogen. Reaction vessels were sealed with either rubber septa or Teflon screw caps. Nitrogen was introduced through Tygon tubing, fitted with a large bore syringe needle. Concentration under vacuum refers to the removal of solvent on a Büchi Rotary Evaporator.

Analytical HPLC was performed using a Supelco discovery $C_{18}$ 15 cm×4.6 mm/5 μm column coupled with an Agilent 1050 series VWD UV detector at 210 nm. Conditions: Solvent A: $H_2O$/1% acetonitrile/0.1% $HCO_2H$; Solvent B: methanol.

Proton magnetic resonance ($^1H$ NMR) spectra were recorded on a Varian INOVA NMR spectrometer [400 MHz ($^1H$) or 500 MHz ($^1H$)]. All spectra were determined in the solvents indicated. Although chemical shifts are reported in ppm downfield of tetramethylsilane, they are referenced to the residual proton peak of the respective solvent peak for $^1H$ NMR. Interproton coupling constants are reported in Hertz (Hz).

LCMS spectra were obtained using a ThermoFinnigan AQA MS ESI instrument utilizing a Phenomenex Aqua 5 micron $C_{18}$ 125 Å 50×4.60 mm column. The spray setting for the MS probe was at 350 μL/min with a cone voltage at 25 mV and a probe temperature at 450° C. The spectra were recorded using ELS and UV (254 nm) detection. Alternatively, LCMS spectra were obtained using an Agilent 1200SL HPLC equipped with a 6130 mass spectrometer operating with electrospray ionization.

Silica gel chromatography was carried out on either a Teledyne ISCO CombiFlash Companion or Companion Rf Flash Chromatography System with a variable flow rate from 5-100 mL/min. The columns used were Teledyne ISCO RediSep Disposable Flash Columns (4, 12, 40, 80, or 120 g prepacked silica gel), which were run with a maximum capacity of 1 g crude sample per 10 g silica gel. Samples were preloaded on Celite in Analogix Sample Loading Cartridges with frits (1/in, 1/out). The eluent was 0-100% EtOAc in heptane or 0-10% MeOH in $CH_2Cl_2$ as a linear gradient over the length of the run (14-20 minutes). Peaks were detected by variable wavelength UV absorption (200-360 nm). The resulting fractions were analyzed, combined as appropriate, and evaporated under reduced pressure to provide purified material.

HPLC purification was performed using a 50 mm Varian Dynamax HPLC 21.4 mm Microsorb Guard-8 $C_{18}$ column, Dyonex Chromeleon operating system coupled with a Varian Prostar 320 UV-vis detector (254 nm) and a Sedex55 ELS detector. Conditions: Solvent A: $H_2O$/1% acetonitrile/ 0.1% $HCO_2H$; Solvent B: MeOH. The appropriate solvent gradient for purification was determined based on the results of analytical HPLC experiments. The resulting fractions were analyzed, combined as appropriate, and evaporated under reduced pressure to provide purified material.

The following experimental sections illustrate procedures for the preparation of intermediates and methods for the preparation of products according to this invention. It should be evident to those skilled in the art that appropriate substitution of both the materials and methods disclosed herein will produce the examples illustrated below and those encompassed by the scope of the invention.

All solvents used were commercially available and were used without further purification. Reactions were typically run using anhydrous solvents under an inert atmosphere of $N_2$.

Compounds are named using the AutoNom 2000 add-on for MDL ISIS™ Draw 2.5 SP2 or their catalogue name if commercially available.

Starting materials used were either available from commercial sources or prepared according to literature procedures and had experimental data in accordance with those reported. 6-aminobenzo[c][1,2]oxaborol-1 (3H)-ol (C50), for example, can be synthesized according to the methods described in U.S. Pat. Pubs. US20060234981 and US20070155699.

Example 1

5-((1-hydroxy-7-methyl-1,3-dihydrobenzo[c][1,2] oxaborol-6-yl)oxy)-N-(2-hydroxyethyl)pyrazine-2-carboxamide

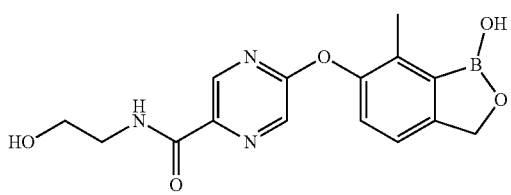 [SMILES: Cc1c(Oc2cnc(C(=O)NCCO)cn2)ccc2c1B(O)OC2]

Step 1: Preparation of 5-chloro-N-(2-hydroxyethyl)pyrazine-2-carboxamide

To a solution of 5-chloropyrazine-2-carboxylic acid (600 mg, 4 mmol, 1 eq), 2-aminoethanol (300 mg, 4.8 mmol, 1.2 eq), HOBT (700 mg, 5.2 mmol, 1.3 eq) and EDC (1 g, 5.2 mmol, 1.3 eq) in DCM (25 mL, c=0.16) was added TEA (1.2 g, 12 mmol, 3 eq). The reaction was stirred at room temperature for 30 min. The mixture was washed with 1N HCl, saturated $NaHCO_3$, brine, dried over $MgSO_4$, filtered and evaporated to give the desired product (610 mg, 80% yield) as yellow oil.

Step 2: Preparation of 3-(benzyloxy)-6-formyl-2-methylphenyl trifluoromethanesulfonate 4-(benzyloxy)-2-hydroxy-3-methylbenzaldehyde (180 g, 742.97 mmol, 1.0 eq) in DCM (2000 mL) was charged into a 3-L 3-necked flask and pyridine (176.31 g, 2.23 mol, 3.0 eq) was then added. Trifluoromethanesulfonic anhydride (314.43 g, 1.114 mol, 1.5 eq) was added dropwise at <25° C. for 2.5 h and then the mixture was stirred at 10-25° C. for 3 h. HPLC showed that the reaction was completed. 1 N HCl (750 mL) was added to the mixture. The separated organic layer was washed by water (2×1000 mL) and concentrated to give the desired product as light yellow solid (240.1 g, yield 86.3%, HPLC purity 98%).

Step 3: Preparation of 4-(benzyloxy)-3-methyl-2-(4, 4,5,5-tetramethyl-1,3,2-dioxaborolan-2-yl) benzaldehyde 3-(Benzyloxy)-6-formyl-2-methylphenyl trifluoromethanesulfonate (110.25 g, 294.53 mmol, 1.0 eq), $Pin_2B_2$(82.26 g, 323.98 mmol, 1.1 eq), potassium acetate (57.84 g, 589.05 mmol, 2.0 eq), $Pd(PPh_3)_2Cl_2$ (14.47 g, 20.62 mmol, 0.07 eq) and 1,4-dioxane (1100 mL) were added to a 2-L 3-necked flask and $N_2$ gas was purged. The resulting mixture was stirred at 90-95° C. for 4 h. TLC showed that the reaction was completed. It was filtered and the filtrate was concentrated at 50° C. to give crude product. EA (600 mL) was charged into the crude product and the solution was washed with water (600 mL×2). The EA layer was concentrated at 40° C. to about 400 g solution of crude product in EA. The solution was charged into a 2 L 3-necked flask and then heated to 60-65° C. Heptane (850 mL) was added dropwise into the solution, which was then cooled slowly to 10-20° C. It was stirred at 10-20° C. for 2 h and then filtered. The solid cake was dried at 40° C. to give the desired product as light yellow solid. (82.2 g, yield 79.3%). $^1$H NMR (500 MHz, DMSO-$d_6$): δ 9.75 (s, 1H), 7.77 (d, 1H), 7.48-7.21 (m, 6H), 5.27 (s, 2H), 2.23 (s, 3H), 1.37 (s, 12H) ppm; HPLC purity 95%.

Step 4: Preparation of 6-(benzyloxy)-7-methylbenzo[c][1,2]oxaborol-1 (3H)-ol 4-(Benzyloxy)-3-methyl-2-(4,4,5,5-tetramethyl-1,3,2-dioxaborolan-2-yl)benzaldehyde (179 g, 508.19 mmol, 1.0 eq), DCM (540 mL) and EtOH (1080 mL) were added into a 3-L 3-necked flask. NaBH$_4$ (19.21 g, 508.19 mmol, 1.0 eq) was added in portions for 1 h and the resulting mixture was stirred at 10-25° C. for another 1 h. TLC showed that the reaction was completed and then 350 mL 1N HCl was added into the reaction mixture. It was stirred for 20 min and some solid was precipitated. The mixture was concentrated at 30° C. to remove the DCM and then 960 mL water was added into the mixture. Solid was precipitated. It was filtered and the solid cake was dissolved in 2.8 L EA and washed with water (100 mL×2). The organic layer was separated and concentrated to give crude product. A mixed solvent of DCM and PE (750 ml, v/v=2:3) was added into the crude product and it was stirred at room temperature for 1 h. It was filtered and the solid cake was dried at 40° C. in vacuum for 2 h to give the pure product as light gray solid (94.1 g, yield 72.9%, and purity 98%). $^1$H NMR (500 MHz, DMSO-$d_6$): δ 8.91 (s, 1H), 7.48-7.32 (m, 5H), 7.14 (s, 2H) 5.12 (s, 2H), 4.88 (s, 2H), 2.35 (s, 3H) ppm.

Step 5: Preparation of 7-methylbenzo[c][1,2]oxaborole-1,6(3H)-diol 6-(Benzyloxy)-7-methylbenzo[c][1,2]oxaborol-1 (3H)-ol (69.0 g, 271.56 mmol, 1.0 eq), Pd/C (6.9 g, 0.1 w/w) and MeOH (1050 mL) were charged into a 2-L 3-necked flask under N$_2$ with mechanical stirring. The flask was set under vacuum (−0.085 MPa) and then H$_2$ gas was purged. The resulting mixture was stirred at 30-35° C. for 6 h. TLC showed that the reaction was completed. It was filtered and the filtrate was concentrated at 40° C. to remove MeOH. Water (150 mL) was added into the mixture. It was stirred at room temperature for 1 h and filtered. The cake was dried at 40° C. in vacuum for 2 h to give the pure product as white solid (35.1 g, yield 79.1%). $^1$H NMR (300 MHz, DMSO-$d_6$): δ 9.03 (s, 1H), 8.76 (s, 1H), 6.98 (d, J=8.1 Hz, 1H), 6.88 (d, J=8.1 Hz, 1H), 4.83 (s, 2H), 2.25 (s, 3H) ppm; HPLC purity: 97.3% at 220 nm.

Step 6: Preparation of 5-((1-hydroxy-7-methyl-1,3-dihydrobenzo[c][1,2]oxaborol-6-yl)oxy)-N-(2-hydroxyethyl)pyrazine-2-carboxamide 7-Methylbenzo[c][1,2]oxaborole-1,6(3H)-diol (10.0 g, 60.99 mmol, 1.0 eq), 5-chloro-N-(2-hydroxyethyl)pyrazine-2-carboxamide (12.29 g, 60.99 mmol, 1.0 eq), Cs$_2$CO$_3$ (49.68 g, 152.47 mmol, 2.5 eq) and DMF (80 mL) were added into a 250-mL 3-necked flask with mechanical stirring. It was stirred at 35-40° C. for 24 h and HPLC showed that the reaction was completed. Water (100 mL) was added and then 700 mL 0.35N HCl was added into the reaction mixture dropwise while white solid was precipitated. The mixture was stirred for 20 min and then filtered. The solid cake was stirred in water (200 mL) for 30 min and filtered. And then the solid was stirred in acetone (300 mL) and filtered. The solid was dissolved in 100 ml DMF at 65° C. and then MeCN (200 mL) was slowly added. The resulting mixture was cooled to room temperature with stirring while light yellow solid was precipitated. It was filtered and the solid cake was stirred again in acetone (300 mL) for 30 min. After filtration, the solid was dried under high vacuum to give the desired product as off-white solid (10.3 g, yield 51.3%). $^1$H NMR (300 MHz, DMSO-$d_6$): δ 9.05 (s, 1H), 8.65 (s, 1H), 8.59 (s, 1H), 8.58-8.55 (m, 1H), 7.28 (d, J=8.1 Hz, 1H), 7.24 (d, J=8.1 Hz, 1H), 4.98 (s, 2H), 4.76 (t, J=5.4 Hz, 1H), 3.54-3.48 (m, 2H), 3.39-3.30 (m, 2H), 2.21 (s, 3H) ppm; HPLC purity: 99.6% at 220 nm and 99.3% at 254 nm; Mass: m/z=330 (M+1).

Example 2

5-(1-hydroxy-7-methyl-1,3-dihydrobenzo[c][1,2]oxaborol-6-yloxy)-N-(2-methoxyethyl)pyrazine-2-carboxamide

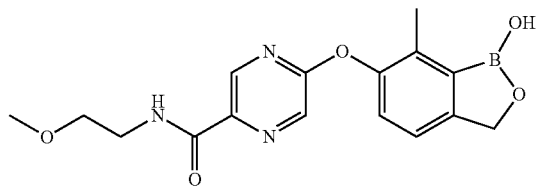 [SMILES: COCCNC(=O)c1cnc(Oc2ccc3c(c2C)B(O)OC3)cn1]

Step 1: Preparation of 5-chloro-N-(2-methoxyethyl)pyrazine-2-carboxamide

To a solution of 5-chloropyrazine-2-carbonyl chloride (600 mg, 3.16 mmol, 1 eq) in DCM (25 mL) were added 2-methoxyethanamine (285 mg, 3.8 mmol, 1.2 eq) and TEA (960 mg, 4.1 mmol, 2.5 eq) at room temperature. The reaction was stirred at room temperature for 2 h. After completion, the reaction was poured into H$_2$O (100 mL) and extracted with DCM (2×20 mL). The combined organic phases were washed with brine, dried over MgSO$_4$, filtered and concentrated in vacuum. The residue was purified by column chromatography to give the desired product (350 mg, 51% yield) as a yellow solid.

Step 2: Preparation of 5-(1-hydroxy-7-methyl-1,3-dihydrobenzo[c][1,2]oxaborol-6-yloxy)-N-(2-methoxyethyl)pyrazine-2-carboxamide To a solution of 5-chloro-N-(2-methoxyethyl)pyrazine-2-carboxamide (216 mg, 1 mmol, 1 eq) in DMF (2 mL) were added 7-methylbenzo[c][1,2]oxaborole-1,6(3H)-diol (164 mg, 1 mmol, 1 eq) and Cs$_2$CO$_3$ (812 mg, 2.5 mmol, 2.5 eq) at room temperature. The reaction was stirred at 50° C. for 2 h. After completion, the reaction was poured into 2N HCl (20 mL) and extracted with EA (2×10 mL). The combined organic phases were washed with brine, dried over MgSO$_4$, filtered and concentrated in vacuum. The residue was purified by column chromatography to give the desired product (45 mg, 13% yield) as a white solid. $^1$H NMR (300 MHz, DMSO-$d_6$): δ 9.07 (s, 1H), 8.66 (s, 1H), 8.62-8.59 (m, 1H), 8.60 (s, 1H), 7.29 (d, J=8.1 Hz, 1H), 7.25 (d, J=8.1 Hz, 1H), 4.98 (s, 2H), 3.47-3.46 (m, 4H), 3.26 (s, 3H), 2.22 (s, 3H) ppm. HPLC purity: 98.2% at 220 nm and 96.9% at 254 nm; Mass: m/z=344 (M+1, ESI+).

Example 3

N-(1-hydroxy-2-methylpropan-2-yl)-5-(1-hydroxy-7-methyl-1,3-dihydrobenzo[c][1,2]oxaborol-6-yloxy)pyrazine-2-carboxamide

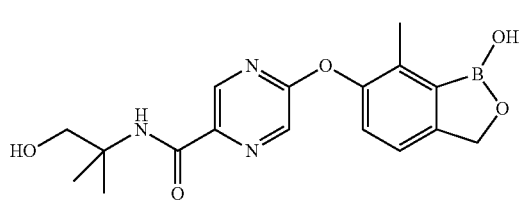 [SMILES: Cc1c(Oc2cnc(C(=O)NC(C)(C)CO)cn2)ccc2c1B(O)OC2]

Step 1: Preparation of 5-chloro-N-(1-hydroxy-2-methylpropan-2-yl)pyrazine-2-carboxamide To a solution of 5-chloropyrazine-2-carboxylic acid (1 g, 6.33 mmol, 1 eq), HOBT (1.11 g, 8.23 mmol, 1.3 eq), and EDC-HCl (1.58 g, 8.23 mmol, 1.3 eq) in DCM (48 mL, c=0.13) were added TEA (1.9 g, 19.0 mmol, 3 eq) and 2-amino-2-methylpropan-1-ol (676 mg, 7.60 mmol, 1.2 eq). The solution was stirred for 2 h. After completion, the reaction was poured into 1N HCl (60 mL) and extracted with DCM (1×20 mL). The combined organic phases were washed with brine, dried over MgSO$_4$, filtered and concentrated in vacuum. The residue was purified by column chromatography to give the 5-chloro-N-(1-hydroxy-2-methylpropan-2-yl)pyrazine-2-carboxamide (200 mg, 14% yield).

Step 2: Preparation of N-(1-hydroxy-2-methylpropan-2-yl)-5-(1-hydroxy-7-methyl-1, 3-dihydrobenzo[c][1,2]oxaborol-6-yloxy)pyrazine-2-carboxamide To a solution of 5-chloro-N-(1-hydroxy-2-methylpropan-2-yl)pyrazine-2-carboxamide (100 mg, 0.437 mmol, 1.1 eq) in DMF (1.3 mL, c=0.3) were added 7-methylbenzo[c][1,2]oxaborole-1,6(3H)-diol (65 mg, 0.397 mmol, 1 eq) and Cs$_2$CO$_3$ (258 mg, 0.794 mmol, 2 eq) at room temperature. The reaction was stirred at 50° C. for 2 h. Then the reaction was poured into water (15 mL), adjusted to pH=5 with 2N HCl. The precipitated solid was filtered. The filter cake was washed with PE. Then the filter cake was dried in vacuum to give the desired product (54 mg, 38% yield). $^1$H NMR (500 MHz, DMSO-d$_6$): δ 9.04 (s, 1H), 8.65 (s, 1H), 8.57 (s, 1H), 7.94 (s, 1H), 7.29 (d, J=8 Hz, 1H), 7.24 (d, J=8 Hz, 1H), 5.13 (t, J=5 Hz, 1H) 4.98 (s, 2H), 3.45 (d, J=5 Hz, 2H), 2.21 (s, 3H), 1.35 (s, 6H) ppm. HPLC purity: 97.8% at 220 nm and 96.8% at 254 nm; Mass: m/z=358.3 (M+1, ESI+).

Example 4

N-(2-hydroxy-2-methylpropyl)-5-(1-hydroxy-7-methyl-1,3-dihydrobenzo[c][1,2]oxaborol-6-yloxy)pyrazine-2-carboxamide

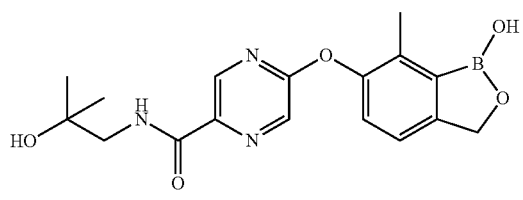 [SMILES: Cc1c(Oc2cnc(C(=O)NCC(C)(C)O)cn2)ccc2c1B(O)OC2]

Step 1: Preparation of 5-chloro-N-(2-hydroxy-2-methylpropyl)pyrazine-2-carboxamide To a solution of 5-chloropyrazine-2-carboxylic acid (1 g, 6.33 mmol, 1 eq), HOBT (1.1 g, 8.23 mmol, 1.3 eq), and EDC-HCl (1.58 g, 8.23 mmol, 1.3 eq) in DCM (48 mL) were added TEA (1.9 g, 19.0 mmol, 3 eq) and 1-amino-2-methylpropan-2-ol (676 mg, 7.60 mmol, 1.2 eq). The solution was stirred for 4 h. After completion, the reaction was poured into 1N HCl (10 mL) and extracted with DCM (1×10 mL). The organic phase was dried over MgSO$_4$, filtered and concentrated in vacuum. The residue was purified by column chromatography to give the 5-chloro-N-(2-hydroxy-2-methylpropyl)pyrazine-2-carboxamide (1. g, 75% yield).

Step 2: Preparation of N-(2-hydroxy-2-methylpropyl)-5-(1-hydroxy-7-methyl-1,3-dihydrobenzo[c][1,2]oxaborol-6-yloxy)pyrazine-2-carboxamide To a solution of 5-chloro-N-(2-hydroxy-2-methylpropyl)pyrazine-2-carboxamide (115 mg, 0.5 mmol, 1 eq) in DMF (1.67 mL) were added 7-methylbenzo[c][1,2]oxaborole-1,6(3H)-diol (82 mg, 0.5 mmol, 1 eq) and Cs$_2$CO$_3$ (326 mg, 1 mmol, 2 eq) at room temperature. The reaction was stirred at 50° C. for 2 h. Then the reaction was poured into water (20 mL), adjusted to pH=4 with 2N HCl. The precipitated solid was filtered. The filter cake was washed with PE. Then the filter cake was dried in vacuum to give the desired product (123 mg, 68% yield). $^1$H NMR (300 MHz, DMSO-d$_6$): δ 9.10 (s, 1H), 8.68 (s, 1H), 8.64 (s, 1H), 8.25-8.40 (m, 1H), 7.30 (d, J=8 Hz, 1H), 7.25 (d, J=8 Hz, 1H), 4.99 (s, 2H), 4.73 (s, 1H), 3.28 (d, J=6.3 Hz, 2H), 2.22 (s, 3H), 1.11 (s, 6H), ppm. HPLC purity: 99.5% at 220 nm and 99.2% at 254 nm; Mass: m/z=358.5 (M+1, ESI+).

Example 5

5-(1-hydroxy-7-methyl-1,3-dihydrobenzo[c][1,2]oxaborol-6-yloxy)-N-(1-hydroxypropan-2-yl)pyrazine-2-carboxamide

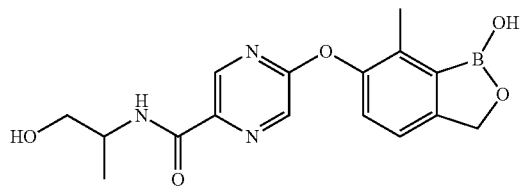 [SMILES: Cc1c(Oc2cnc(C(=O)NC(C)CO)cn2)ccc2c1B(O)OC2]

Step 1: Preparation of 5-chloro-N-(1-hydroxypropan-2-yl)pyrazine-2-carboxamide To a solution of 5-chloropyrazine-2-carboxylic acid (1 g, 6.33 mmol, 1 eq) and TEA (704 mg, 6.96 mmol, 1.1 eq) in DCM (31.6 mL) was added isobutyl chloroformate (944 mg, 6.96 mmol, 1.1 eq) at 0° C. The reaction was stirred for 20 min. Then 2-aminopropan-1-ol (523 mg, 6.96 mmol, 1.1 eq) was added and stirred for 1 h. After completion, the reaction was added 1N HCl (4 mL) and extracted with DCM (2×8 mL). The combined organic phases were dried over MgSO$_4$, filtered, evaporated and purified by column chromatography to give the 5-chloro-N-(1-hydroxypropan-2-yl)pyrazine-2-carboxamide (0.8 g, 58% yield).

Step 2: Preparation of 5-(1-hydroxy-7-methyl-1,3-dihydrobenzo[c][1,2]oxaborol-6-yloxy)-N-(1-hydroxypropan-2-yl)pyrazine-2-carboxamide To a solution of 5-chloro-N-(1-hydroxypropan-2-yl)pyrazine-2-carboxamide (150 mg, 0.7 mmol, 1.1 eq) in DMF (2.1 mL, c=0.3) were added 7-methylbenzo[c][1,2]oxaborole-1,6(3H)-diol (104 mg, 0.63 mmol, 1 eq) and Cs$_2$CO$_3$ (413 mg, 12.7 mmol, 2 eq) at room temperature. The reaction was stirred at 50° C. for 1 h. Then the reaction was poured into water (30 mL), adjusted to pH=4 with 2N HCl. The precipitated solid was filtered. The filter cake was washed with PE. Then the filter cake was dried in vacuum to give the product (124 mg, 57% yield). $^1$H NMR (500 MHz, DMSO-d$_6$): δ 9.04 (s, 1H), 8.66 (s, 1H), 8.59 (s, 1H), 8.27 (d, J=8.5 Hz, 1H), 7.29 (d, J=8 Hz, 1H), 7.25 (d, J=8.5 Hz, 1H), 4.98 (s, 2H), 4.80 (t, J=5.5 Hz, 1H), 4.10-4.00 (m, 1H), 3.50-3.40 (m, 2H), 2.22 (s, 3H), 1.15 (d, J=7 Hz, 3H) ppm. HPLC purity: 96.5% at 220 nm and 95.1% at 254 nm; Mass: m/z=344 (M+1, ESI+).

Example 6

5-(1-hydroxy-7-methyl-1,3-dihydrobenzo[c][1,2]oxaborol-6-yloxy)-N,N-bis(2-hydroxyethyl)pyrazine-2-carboxamide

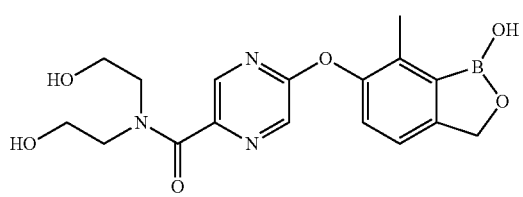 [SMILES: Cc1c(Oc2cnc(C(=O)N(CCO)CCO)cn2)ccc2c1B(O)OC2]

Step 1: Preparation of 5-chloro-N,N-bis(2-hydroxyethyl)pyrazine-2-carboxamide To a solution of 5-chloropyrazine-2-carboxylic acid (1 g, 6.33 mmol, 1 eq) and TEA (704 mg, 6.96 mmol, 1.1 eq) in DCM (31.6 mL) was added isobutyl chloroformate (944 mg, 6.96 mmol, 1.1 eq) at 0° C. The reaction was stirred for 20 min. Then 2,2'-azanediyldiethanol (732 mg, 6.96 mmol, 1.1 eq) was added and stirred for 1 h. After completion, the reaction was added 1N HCl (4 mL) and extracted with DCM (2×8 mL). The combined organic phase was dried over MgSO$_4$, filtered, evaporated and purified by column chromatography to 5-chloro-N,N-bis(2-hydroxyethyl)pyrazine-2-carboxamide (700 mg, 45% yield).

Step 2: Preparation of 5-(1-hydroxy-7-methyl-1,3-dihydrobenzo[c][1,2]oxaborol-6-yloxy)-N,N-bis(2-hydroxyethyl)pyrazine-2-carboxamide To a solution of 5-chloro-N,N-bis(2-hydroxyethyl)pyrazine-2-carboxamide (123 mg, 0.5 mmol, 1 eq) in DMF (1.67 mL) were added 7-methylbenzo[c][1,2]oxaborole-1,6(3H)-diol (82 mg, 0.5 mmol, 1 eq) and Cs$_2$CO$_3$ (326 mg, 1 mmol, 2 eq) at room temperature. The reaction was stirred at 50° C. for 2 h. Then the reaction was poured into water (30 mL), adjusted to pH=4 with 2N HCl and extracted with EA (2×10 mL). The combined organic phase was washed with brine, dried over MgSO$_4$, filtered and concentrated in vacuum. The residue was purified by column chromatography to give the desired product (16 mg, 8% yield). $^1$H NMR (500 MHz, DMSO-d$_6$): δ 9.02 (s, 1H), 8.49 (s, 1H), 8.30 (s, 1H), 7.27 (d, J=8 Hz, 1H), 7.23 (d, J=8 Hz, 1H), 4.97 (s, 2H), 4.76 (t, J=5 Hz, 1H), 4.55-4.70 (m, 1H), 3.61-3.59 (m, 2H), 3.54-3.51 (m, 2H), 3.49 (s, 4H), 2.22 (s, 3H) ppm. HPLC purity: 96.7% at 254 nm; Mass: m/z=374 (M+1, ESI+).

Example 7

N-(1-hydroxy-3-methylbutan-2-yl)-5-(1-hydroxy-7-methyl-1,3-dihydrobenzo[c][1,2]oxaborol-6-yloxy)pyrazine-2-carboxamide

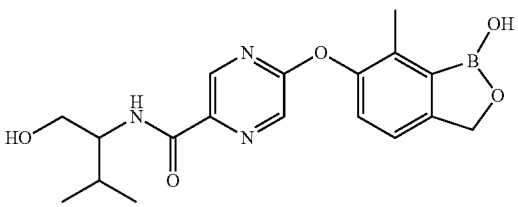 [SMILES: Cc1c(Oc2cnc(C(=O)NC(CO)C(C)C)cn2)ccc2c1B(O)OC2]

Step 1: Preparation of 5-chloro-N-(1-hydroxy-3-methylbutan-2-yl)pyrazine-2-carboxamide To a solution of 5-chloropyrazine-2-carboxylic acid (500 mg, 3.16 mmol, 1 eq) and TEA (352 mg, 3.48 mmol, 1.1 eq) in DCM (15.8 mL, c=0.20) was added isobutyl chloroformate (472 mg, 3.48 mmol, 1.1 eq) at 0° C. The solution was stirred for 0.5 h. Then 2-amino-3-methylbutan-1-ol (359 mg, 3.48 mmol, 1.1 eq) was added and stirred for 1 h. After completion, the reaction was poured into 2N HCl (20 mL) and extracted with DCM (2×5 mL). The combined organic phase was dried over MgSO$_4$, filtered, evaporated and purified by column chromatography to give 5-chloro-N-(1-hydroxy-3-methylbutan-2-yl)pyrazine-2-carboxamide (270 mg, 35% yield).

Step 2: Preparation of N-(1-hydroxy-3-methylbutan-2-yl)-5-(1-hydroxy-7-methyl-1,3-dihydrobenzo[c][1,2]oxaborol-6-yloxy)pyrazine-2-carboxamide To a solution of 5-chloro-N-(1-hydroxy-3-methylbutan-2-yl)pyrazine-2-carboxamide (134 mg, 0.55 mmol, 1.1 eq) in DMF (2.5 mL) were added 7-methylbenzo[c][1,2]oxaborole-1,6(3H)-diol (82 mg, 0.5 mmol, 1 eq) and Cs$_2$CO$_3$ (325 mg, 1 mmol, 2 eq) at room temperature. The reaction was stirred at 50° C. for 2 h. Then the reaction was poured into water (20 mL), adjusted to pH=4 with 2N HCl. The precipitated solid was filtered. The filter cake was washed with EA/PE (1/2 mixture). Then the filter cake was dried in vacuum to give the desired product (74 mg, 20% yield). $^1$H NMR (500 MHz, DMSO-$d_6$): δ 9.04 (s, 1H), 8.67 (s, 1H), 8.61 (s, 1H), 8.11 (d, J=9.5 Hz, 1H), 7.30 (d, J=8 Hz, 1H), 7.25 (d, J=8 Hz, 1H), 4.99 (s, 2H), 4.70 (t, J=5 Hz, 1H), 3.78-3.76 (m, 1H), 3.61-3.56 (m, 1H), 3.53-3.29, 2.23 (s, 3H), 1.97-1.92 (m, 1H), 0.92 (d, J=7 Hz, 3H), 0.87 (d, J=7 Hz, 3H) ppm. HPLC purity: 96.3% at 220 nm and 97.8% at 254 nm; Mass: m/z=372 (M+1, ESI+).

Example 8

N-(1-hydroxy-4-methylpentan-2-yl)-5-((1-hydroxy-7-methyl-1,3-dihydrobenzo[c][1,2]oxaborol-6-yl)oxy)pyrazine-2-carboxamide

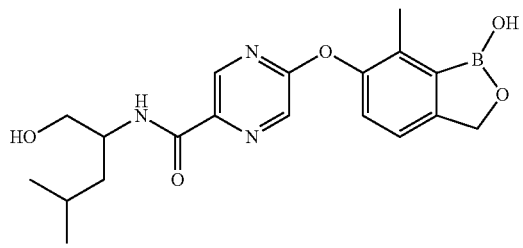 [SMILES: Cc1c(Oc2cnc(C(=O)NC(CO)CC(C)C)cn2)ccc2c1B(O)OC2]

Step 1: Preparation of 2-amino-4-methylpentan-1-ol

To a solution of 2-amino-4-methylpentanoic acid (10 g, 76 mmol, 1 eq) in THF (200 mL) were added NaBH$_4$ (6.92 g, 183 mmol, 2.4 eq) and then a solution of I$_2$ (19.3 g, 76 mmol, 1 eq) in THF (50 mL) dropwise at 0° C. After addition, the reaction was allowed to warm to room temperature. Once no bubble was emerged from the mixture, the reaction mixture was allowed to reflux overnight. Then the reaction was quenched slowly with MeOH (25 mL) and concentrated directly to give a residue. 20% KOH (150 mL) was added and extracted with DCM (3×150 mL). The combined organic phase was washed with brine, dried over Na$_2$SO$_4$, filtered and evaporated to give the desired product (8.67 g, 97% yield) as oil.

Step 2: Preparation of 5-chloro-N-(1-hydroxy-4-methylpentan-2-yl)pyrazine-2-carboxamide To a solution of 5-chloropyrazine-2-carboxylic acid (1 g, 6.3 mmol, 1 eq) in DCM (31 mL, c=0.2) were added TEA (703 mg, 6.96 mmol, 1.1 eq) and a solution of isobutyl chloroformate (943 mg, 6.96 mmol, 1.1 eq) in DCM (3 mL) dropwise at −10° C. In 15 min, 2-amino-4-methylpentan-1-ol (814 mg, 6.96 mmol, 1.1 eq) was added and the reaction was monitored by TLC. The reaction was quenched with 1N HCl (10 mL), poured into water (20 mL) and extracted with DCM (2×30 mL). The combined organic phase was washed with brine, dried over MgSO$_4$, filtered and concentrated in vacuum. The residue was purified by column chromatography to give the desired product (380 mg, 23% yield) as a solid.

Step 3: Preparation of N-(1-hydroxy-4-methylpentan-2-yl)-5-((1-hydroxy-7-methyl-1, 3-dihydrobenzo[c][1,2]oxaborol-6-yl)oxy)pyrazine-2-carboxamide To a solution of 5-chloro-N-(1-hydroxy-4-methylpentan-2-yl)pyrazine-2-carboxamide (100 mg, 0.4 mmol, 1 eq) in DMF (1 mL) were added 7-methylbenzo[c][1,2]oxaborole-1,6(3H)-diol (65 mg, 0.4 mmol, 1 eq) and Cs$_2$CO$_3$ (325 mg, 1 mmol, 2.5 eq) at room temperature. The reaction was stirred at 40° C. for 2 h. After completion, the reaction was poured into 1N HCl (20 mL) and extracted with EA (2×10 mL). The combined organic phase was washed with brine, dried over MgSO$_4$, filtered and concentrated in vacuum. The residue was purified by column chromatography to give the desired product (50 mg, 33% yield) as a solid. $^1$H NMR (300 MHz, DMSO-$d_6$): δ 9.05 (s, 1H), 8.66 (s, 1H), 8.59 (s, 1H), 8.20 (d, J=9.3 Hz, 1H), 7.30 (d, J=8 Hz, 1H), 7.25 (d, J=8 Hz, 1H), 4.99 (s, 2H), 4.73 (t, J=7.8 Hz, 1H), 4.06-4.04 (m, 1H), 3.47-3.39 (m, 2H), 2.23 (s, 3H), 1.55-1.48 (m, 2H), 1.40-1.37 (m, 1H), 0.88 (d, J=6.3 Hz, 6H) ppm. HPLC purity: 97.3% at 220 nm and 97.2% at 254 nm; Mass: m/z=386 (M+1, ESI+).

Example 9

5-(1-hydroxy-7-methyl-1,3-dihydrobenzo[c][1,2]oxaborol-6-yloxy)-N-(2-hydroxypropyl)pyrazine-2-carboxamide

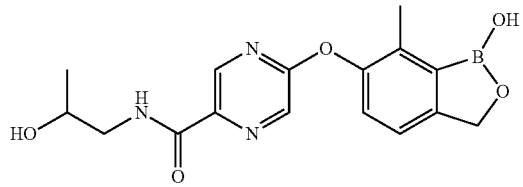 [SMILES: Cc1c(Oc2cnc(C(=O)NCC(C)O)cn2)ccc2c1B(O)OC2]

Preparation of 5-((1-hydroxy-7-methyl-1,3-dihydrobenzo[c][1,2]oxaborol-6-yl)oxy)-N-(2-hydroxypropyl) pyrazine-2-carboxamide 5-chloro-N-(2-hydroxypropyl)pyrazine-2-carboxamide was synthesized from 5-chloropyrazine-2-carboxylic acid and 1-aminopropan-2-ol by using the method in the previous example. To a solution of the obtained amide (130 mg, 0.60 mmol, 1 eq) in DMF (1.2 mL) were added 7-methylbenzo[c][1,2]oxaborole-1,6(3H)-diol (100 mg, 0.6 mmol, 1 eq) and Cs$_2$CO$_3$ (495 mg, 1.5 mmol, 2.5 eq) at room temperature. The reaction was stirred at 40° C. for 2 h, poured into 1N HCl (20 mL) and extracted with EA (2×20 mL). The combined organic phase was washed with brine, dried over MgSO$_4$, filtered and concentrated in vacuum. The residue was purified by column chromatography to give the desired product (65 mg, 29% yield) as a solid. $^1$H NMR (300 MHz, DMSO-$d_6$): δ 9.06 (s, 1H), 8.66 (s, 1H), 8.60 (s, 1H), 8.48 (t, J=6.0 Hz, 1H), 7.29 (d, J=8 Hz, 1H), 7.25 (d, J=8 Hz, 1H), 4.98 (s, 2H), 4.82 (d, J=4.8 Hz, 1H), 3.83-3.76 (m, 1H), 3.28-3.19 (m, 2H), 2.22 (s, 3H), 1.06 (d, J=6.0 Hz, 3H) ppm. HPLC purity: 99.1% at 220 nm and 98.9% at 254 nm; Mass: m/z=344 (M+1, ESI+), 366 (M+23, ESI+).

Example 10

5-(1-hydroxy-7-methyl-1,3-dihydrobenzo[c][1,2]oxaborol-6-yloxy)-N-(2-hydroxyethyl)-N-methyl-pyrazine-2-carboxamide

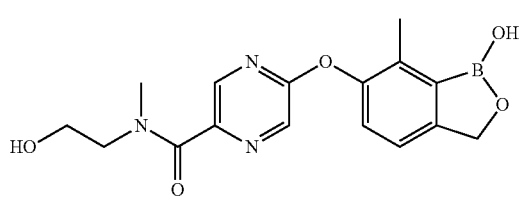 [SMILES: Cc1c(Oc2cnc(C(=O)N(C)CCO)cn2)ccc2c1B(O)OC2]

Step 1: Preparation of 5-chloro-N-(2-hydroxyethyl)-N-methylpyrazine-2-carboxamide To a solution of 5-chloropyrazine-2-carboxylic acid (500 mg, 3.16 mmol, 1 eq) and TEA (352 mg, 3.48 mmol, 1.1 eq) in DCM (158 mL) was added isobutyl chloroformate (472 mg, 3.48 mmol, 1.1 eq) at 0° C. The solution was stirred for 20 min. Then 2-(methylamino)ethan-1-ol (261 mg in 5 mL DCM) was added and stirred for 20 min. After completion, the reaction was poured into 2N HCl (10 mL) and extracted with DCM (2×5 mL). The combined organic phase was dried over MgSO$_4$, filtered, evaporated and purified by column chromatography to give 5-chloro-N-(2-hydroxyethyl)pyrazine-2-carboxamide (480 mg, 70% yield).

Step 2: Preparation of 5-(1-hydroxy-7-methyl-1,3-dihydrobenzo[c][1,2]oxaborol-6-yloxy)-N-(2-hydroxyethyl)-N-methylpyrazine-2-carboxamide To a solution of 5-chloro-N-(2-hydroxyethyl)-N-methylpyrazine-2-carboxamide (236 mg, 1.1 mmol, 1.1 eq) in DMF (5 mL) were added 7-methylbenzo[c][1,2]oxaborole-1,6(3H)-diol (164 mg, 1 mmol, 1 eq) and Cs$_2$CO$_3$ (650 mg, 2 mmol, 2 eq) at room temperature. The reaction was stirred at 50° C. for 1 h. After completion, the reaction was poured into water (30 mL), adjusted to pH=4 with 2N HCl and extracted with EA (2×15 mL). The combined organic phase was washed with brine, dried over MgSO$_4$, filtered and concentrated in vacuum. The residue was purified by column chromatography to give the desired product (90 mg, 26% yield). $^1$H NMR (300 MHz, DMSO-d$_6$): δ 9.07 (s, 1H), 8.60-8.45 (m, 1H), 8.40-8.25 (m, 1H), 7.35-7.20 (m, 2H), 4.98 (s, 2H), 4.82-4.62 (m, 1H), 3.70-3.30 (m, 4H), 3.12-2.95 (m, 3H), 2.24 (s, 3H) ppm. HPLC purity: 100% at 220 nm and 98% at 254 nm; Mass: m/z=344 (M+1, ESI+), 366 (M+23, ESI+).

Example 11

((R)-5-(1-hydroxy-7-methyl-1,3-dihydrobenzo[c][1,2]oxaborol-6-yloxy)-N-(1-hydroxypropan-2-yl)pyrazine-2-carboxamide

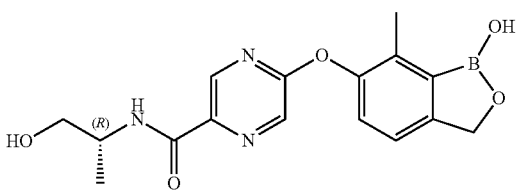

Step 1: Preparation of (R)-5-chloro-N-(1-hydroxypropan-2-yl)pyrazine-2-carboxamide To a solution of 5-chloropyrazine-2-carboxylic acid (1.5 g, 9.5 mmol, 1.0 eq) in DCM (48 mL, c=0.20) were added TEA (1.06 g, 10.4 mmol, 1.1 eq) and isobutyl chloroformate (1.4 g, 10.4 mmol, 1.1 eq) in ice-water bath. (R)-2-amino-propan-1-ol (784 mg, 10.4 mmol, 1.1 eq) was added after 10 min. The reaction was stirred at room temperature for 20 min. After completion, the reaction mixture was adjusted to pH=4 with 1N HCl. The mixture was extracted with DCM (2×50 mL). The combined organic phase was washed with brine, dried over MgSO$_4$, filtered and concentrated to give a residue. The residue was purified by column chromatography to give the desired product (1.1 g, 55% yield) as a white solid.

Step 2: Preparation of (R)-5-(1-hydroxy-7-methyl-1,3-dihydrobenzo[c][1,2]oxaborol-6-yloxy)-N-(1-hydroxypropan-2-yl)pyrazine-2-carboxamide To a solution of (R)-5-chloro-N-(1-hydroxypropan-2-yl)pyrazine-2-carboxamide (550 mg, 2.5 mmol, 1.0 eq) and 7-methylbenzo[c][1,2]oxaborole-1,6(3H)-diol (420 mg, 2.5 mmol, 1.0 eq) in DMF (8.5 mL) was added Cs$_2$CO$_3$ (1.65 g, 5.1 mmol, 2.0 eq) under nitrogen. The solution was stirred at 30° C. for 1 h. After completion, the reaction mixture was adjusted to pH=6 slowly with 1N HCl and then filtered to give the desired product (340 mg, 40% yield) as a white solid. $^1$H NMR (300 MHz, DMSO-d$_6$): δ 9.08 (s, 1H), 8.66 (s, 1H), 8.60 (s, 1H), 8.30 (d, J=8.4 Hz, 1H), 7.29 (d, J=8 Hz, 1H), 7.25 (d, J=8 Hz, 1H), 4.99 (s, 2H), 4.83 (t, 1H), 4.04 (m, 1H), 3.43-3.45 (m, 2H), 2.22 (s, 3H), 1.15 (d, J=6.6 Hz, 3H) ppm. HPLC purity: 99.3% at 220 nm and 99.7% at 254 nm; Mass: m/z=344 (M+1, ESI+).

Example 12

(S)-5-(1-hydroxy-7-methyl-1,3-dihydrobenzo[c][1,2]oxaborol-6-yloxy)-N-(1-hydroxypropan-2-yl)pyrazine-2-carboxamide

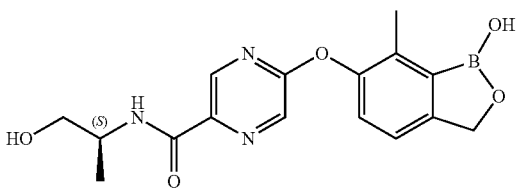

Step 1: Preparation of (S)-5-chloro-N-(1-hydroxypropan-2-yl)pyrazine-2-carboxamide To a solution of 5-chloropyrazine-2-carboxylic acid (500 mg, 3.2 mmol, 1.0 eq) in DCM (16 mL) was added TEA (352 mg, 3.5 mmol, 1.1 eq) and isobutyl chloroformate (472 mg, 3.5 mmol, 1.1 eq) in ice-water bath under nitrogen. (S)-2-aminopropan-1-ol (261 mg, 3.5 mmol, 1.1 eq) was added after 10 min. The solution was stirred at room temperature for 2 h. After completion, the reaction mixture was adjusted to pH=3 with 1N HCl. The mixture was extracted with DCM (2×30 mL) to give a residue. The residue was purified by column chromatography to give the desired product (500 mg, 73% yield).

Step 2: Preparation of (S)-5-(1-hydroxy-7-methyl-1,3-dihydrobenzo[c][1,2]oxaborol-6-yloxy)-N-(1-hydroxypropan-2-yl)pyrazine-2-carboxamide To a solution of (S)-5-chloro-N-(1-hydroxypropan-2-yl)pyrazine-2-carboxamide (100 mg, 0.46 mmol, 1.0 eq) and 7-methylbenzo[c][1,2]oxaborole-1,6(3H)-diol (76 mg, 0.46 mmol, 1.0 eq) in DMF (1.5 mL) was added $Cs_2CO_3$ (303 mg, 0.93 mmol, 2 eq). The solution was stirred at room temperature for 1 h and then at 30° C. for 1 h. After completion, the reaction mixture was adjusted to pH=3 with 1N HCl. The aqueous phase was extracted with DCM (2×30 mL). The combined organic phase was washed with brine, dried over $MgSO_4$, filtered and concentrated to give a residue. The residue was purified by column chromatography to give the desired product (77 mg, 10% yield). $^1$H NMR (300 MHz, DMSO-$d_6$): δ 9.08 (s, 1H), 8.66 (s, 1H), 8.60 (s, 1H), 8.30 (d, J=8.4 Hz, 1H), 7.29 (d, J=8 Hz, 1H), 7.25 (d, J=8 Hz, 1H), 4.99 (s, 2H), 4.83 (t, J=5.7 Hz, 1H), 4.10-4.00 (m, 1H), 3.47-3.40 (m, 2H), 2.22 (s, 3H), 1.15 (d, J=6.6 Hz, 3H) ppm. HPLC purity: 99.3% at 220 nm and 99.6% at 254 nm; Mass: m/z=344 (M+1, ESI+).

Example 13

(S)-5-(1-hydroxy-7-methyl-1,3-dihydrobenzo[c][1,2]oxaborol-6-yloxy)-N-(1-hydroxypentan-2-yl)pyrazine-2-carboxamide

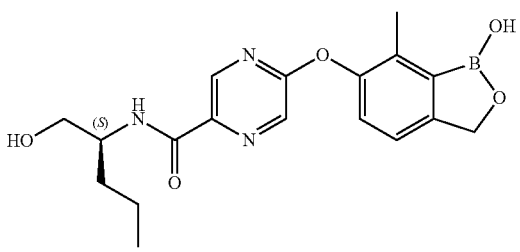

Step 1: Preparation of (S)-2-aminopentan-1-ol hydrochloride

To a solution of $NaBH_4$ (7.75 g, 205 mmol, 2.4 eq) in THF (200 mL) was added (S)-2-aminobutanoic acid (10 g, 85.4 mmol, 1 eq) at −10° C. A solution of $I_2$ (21.7 g, 83.4 mole, 1 eq) in THF (85 mL) was added dropwise into the reaction with stirring at −10° C. After no gas released, the reaction was stirred at 68° C. for 21 h. MeOH (40 mL) was added dropwise into the reaction with stirring at 0° C. until the reaction was clarified and then concentrated directly. The residue was dissolved in 4M $KOH/H_2O$ (150 mL), stirred at room temperature for 4 h and extracted with DCM (3×150 mL). The combined organic phase was washed with brine, dried over $MgSO_4$, filtered and evaporated to give the (S)-2-aminopentan-1-ol (8 g, 91% yield). To a solution of (S)-2-aminopentan-1-ol (8 g, 77.5 mmol, 1 eq) in MeOH (75 mL) was added 4N HCl (80 mL). The reaction was stirred at room temperature for 2 h and then concentrated directly. The residue was washed with EA/PE (1/3 mixture), dried in vacuuo to give the (S)-2-aminopentan-1-ol hydrochloride (8.5 g, 78% yield).

Step 2: Preparation of (S)-5-chloro-N-(1-hydroxypentan-2-yl)pyrazine-2-carboxamide To a solution of 5-chloropyrazine-2-carboxylic acid (500 mg, 3.16 mol, 1 eq) in NMP (21 mL) was added 2-chloro-1-methylpyridinium iodide (CMPI, 2.02 g, 7.91 mmol, 2.5 eq). The reaction was stirred at room temperature for 1 h. Then (S)-2-aminopentan-1-ol hydrochloride (442 mg, 3.16 mmol, 1 eq) and DIPEA (2.45 g, 19.0 mmol, 6 eq) were added and stirred for 1 h. After completion, the reaction was poured into water (250 mL), adjusted to pH=4 with 2N HCl and extracted with EA (2×90 mL). The combined organic phase was washed with brine, dried over MgSO4, filtered and concentrated in vacuum. The residue was purified by column chromatography to give (S)-5-chloro-N-(1-hydroxypentan-2-yl)pyrazine-2-carboxamide (710 mg, yield 90%).

Step 3: Preparation of (S)-5-(1-hydroxy-7-methyl-1,3-dihydrobenzo[c][1,2]oxaborol-6-yloxy)-N-(1-hydroxypentan-2-yl)pyrazine-2-carboxamide To a solution of (S)-5-chloro-N-(1-hydroxypentan-2-yl)pyrazine-2-carboxamide (700 mg, 2.87 mmol, 1 eq) in DMF (14.4 mL) were added 7-methylbenzo[c][1,2]oxaborole-1,6(3H)-diol (471 mg, 2.87 mmol, 1 eq) and $Cs_2CO_3$ (1.87 g, 5.75 mmol, 2 eq) at room temperature. The reaction was stirred at 50° C. for 2 h. After completion, the reaction was poured into water (150 mL), adjusted to pH=4 with 2N HCl. The precipitated solid was filtered. The filter cake was purified by column chromatography to give the desired product (330 mg, 31% yield). $^1$H NMR (300 MHz, DMSO-$d_6$): δ 9.08 (s, 1H), 8.66 (s, 1H), 8.60 (s, 1H), 8.22 (d, J=9 Hz, 1H), 7.29 (d, J=8 Hz, 1H), 7.26 (d, J=8 Hz, 1H), 4.99 (s, 2H), 4.72-4.82 (m, 1H), 4.05-3.90 (m, 1H), 3.55-3.35 (m, 2H), 2.22 (s, 3H), 1.68-1.40 (m, 2H), 1.40-1.20 (m, 2H), 0.87 (t, J=7.2 Hz, 3H) ppm. HPLC purity: 99.7% at 220 nm and 99.5% at 254 nm; Mass: m/z=372 (M+1, ESI+).

Example 14

(R)-5-(1-hydroxy-7-methyl-1,3-dihydrobenzo[c][1,2]oxaborol-6-yloxy)-N-(1-hydroxypentan-2-yl)pyrazine-2-carboxamide

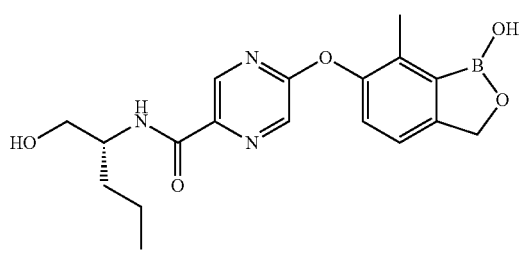 [SMILES: CCC[C@H](CO)NC(=O)c1cnc(Oc2ccc3c(c2C)B(O)OC3)cn1]

Step 1: Preparation of (R)-5-chloro-N-(1-hydroxypentan-2-yl)pyrazine-2-carboxamide To a solution of 5-chloropyrazine-2-carboxylic acid (500 mg, 3.2 mmol, 1.0 eq) in DCM (16 mL) were added TEA (352 mg, 3.5 mmol, 1.1 eq) and isobutyl chloroformate (472 mg, 3.5 mmol, 1.1 eq) at 0° C. under nitrogen. After 10 min, (R)-2-aminopentan-1-ol (359 mg, 3.5 mmol, 1.1 eq) was added in portions. The solution was stirred at room temperature for 2 h. After completion, the reaction mixture was adjusted to pH=3 with 1N HCl and extracted with DCM (2×30 mL). The combined organic phase was washed with brine, dried over MgSO₄, filtered and concentrated to give a residue. The residue was purified by column chromatography to give the desired product (500 mg, 73% yield).

Step 2: Preparation of (R)-5-(1-hydroxy-7-methyl-1,3-dihydrobenzo[c][1,2]oxaborol-6-yloxy)-N-(1-hydroxypentan-2-yl)pyrazine-2-carboxamide To a solution of (R)-5-chloro-N-(1-hydroxypentan-2-yl)pyrazine-2-carboxamide (63 mg, 0.26 mmol, 1.0 eq) and 7-methylbenzo[c][1,2]oxaborole-1,6(3H)-diol (42 mg, 0.26 mmol, 1.0 eq) in DMF (1.5 mL, c=0.30) was added $Cs_2CO_3$ (168 mg, 0.52 mmol, 2 eq). The mixture was stirred at 30° C. for 1 h. After completion, the reaction mixture was adjusted to pH=3 with 1N HCl and filtered. The filtered cake was dissolved by EA (1 mL), dried over MgSO₄, filtered and concentrated to give a residue. The residue was purified by column chromatography to give the desired product (60 mg, 63% yield) as a white solid. ¹H NMR (500 MHz, DMSO-$d_6$): δ 9.09 (s, 1H), 8.66 (s, 1H), 8.61 (s, 1H), 8.24 (d, J=9.0 Hz, 1H), 7.30 (d, J=8 Hz, 1H), 7.25 (d, J=8 Hz, 1H), 4.99 (s, 2H), 4.78 (t, J=5.5 Hz, 1H), 4.01-3.94 (m, 1H), 3.51-3.45 (m, 1H), 3.45-3.40 (m, 1H), 2.22 (s, 3H), 1.61-1.45 (m, 2H), 1.40-1.20 (m, 2H), 0.87 (t, J=6.9 Hz, 3H) ppm. HPLC purity: 99.2% at 220 nm and 99.3% at 254 nm; Mass: m/z=372 (M+1, ESI+).

Example 15

N-(1-hydroxy-3-phenylpropan-2-yl)-5-(1-hydroxy-7-methyl-1,3-dihydrobenzo[c][1,2]oxaborol-6-yloxy)pyrazine-2-carboxamide

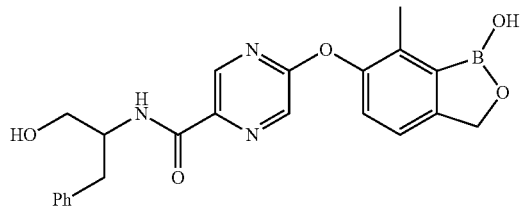 [SMILES: Cc1c(Oc2cnc(C(=O)NC(CO)Cc3ccccc3)cn2)ccc2c1B(O)OC2]

Step 1: Preparation of 6-chloro-N-(1-hydroxy-3-phenylpropan-2-yl)pyrazine-2-carboxamide To a solution of 5-chloropyrazine-2-carboxylic acid (500 mg, 3.2 mmol, 1 eq) in NMP (21 mL) was added 2-chloro-1-methylpyridinium iodide (CMPI, 352 mg, 3.5 mmol, 1.1 eq) with stirring for 30 min. And then to the reaction mixture were added 2-amino-3-phenylpropan-1-ol (478 mg, 3.16 mmol, 1 eq) and DIPEA (2.78 g, 21.5 mmol, 6 eq) for 5 min. The solution was stirred at room temperature for 2 h. After completion, the reaction mixture was adjusted pH=3 with 2N HCl, extracted with DCM (2×30 mL). The organic phase was washed with brine (50 mL), dried over anhydrous $Na_2SO_4$, filtered and concentrated in vacuum. The residue was purified by column chromatography to give the desired product (650 mg, 71% yield) as a white solid.

Step 2: Preparation of N-(1-hydroxy-3-phenylpropan-2-yl)-5-(1-hydroxy-7-methyl-1, 3-dihydrobenzo[c][1,2]oxaborol-6-yloxy)pyrazine-2-carboxamide To a solution of 6-chloro-N-(1-hydroxy-3-phenylpropan-2-yl)pyrazine-2-carboxamide (293 mg, 1.0 mmol, 1.1 eq) and 7-methylbenzo[c][1,2]oxaborole-1,6(3H)-diol (150 mg, 0.91 mmol, 1.0 eq) in DMF (5 mL) was added $Cs_2CO_3$ (0.74 g, 2.27 mmol, 2.5 eq). The solution was stirred at 50° C. for 2 h. After completion, the reaction was poured into 1N HCl (50 mL) and extracted with EA (3×30 mL). The combined organic phase was washed with brine, dried over $Na_2SO_4$, filtered and concentrated in vacuum. The residue was purified by column chromatography to give the desired product (145 mg, 38% yield) as a white solid. ¹H NMR (300 MHz, DMSO-$d_6$): δ 9.08 (s, 1H), 8.60 (s, 2H), 8.39 (d, J=9.0 Hz, 1H), 7.30-7.10 (m, 7H), 4.98 (s, 2H), 4.95-4.90 (m, 1H), 4.30-4.10 (m, 1H), 3.55-3.40 (m, 2H), 3.00-2.80 (m, 2H), 2.21 (s, 3H) ppm. HPLC purity: 96.2% at 220 nm and 96.1% at 254 nm; Mass: m/z=420 (M+1, ESI+).

Example 16

N-(2-hydroxy-1-phenylethyl)-5-(1-hydroxy-7-methyl-1,3-dihydrobenzo[c][1,2]oxaborol-6-yloxy)pyrazine-2-carboxamide

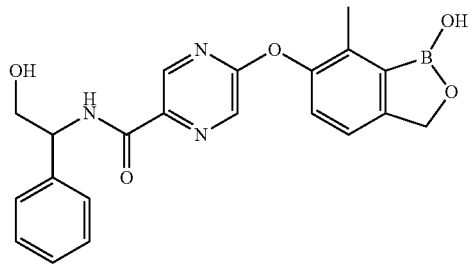 [SMILES: Cc1c(Oc2cnc(C(=O)NC(CO)c3ccccc3)cn2)ccc2c1B(O)OC2]

Step 1: Preparation of 5-chloro-N-(2-hydroxy-1-phenylethyl)pyrazine-2-carboxamide To a solution of 5-chloropyrazine-2-carboxylic acid (500 mg, 3.16 mmol, 1 eq) in NMP (21 mL) was added CMPI (2.02 g, 7.91 mmol, 2.5 eq). The reaction was stirred at room temperature for 1 h. Then 2-amino-2-phenylethanol (434 mg, 3.16 mmol, 1 eq) and DIPEA (2.78 g, 21.5 mmol, 6.8 eq) were added and stirred for 1 h. After completion, the reaction was poured into water (200 mL), adjusted to pH=4 with 2N HCl and extracted with EA (2×20 mL). The combined organic phase was washed with brine, dried over $MgSO_4$, filtered and concentrated in vacuum to give 5-chloro-N-(2-hydroxy-1-phenylethyl)pyrazine-2-carboxamide (600 mg, 68% yield).

Step 2: Preparation of N-(2-hydroxy-1-phenylethyl)-5-(1-hydroxy-7-methyl-1,3-dihydrobenzo[c][1,2]oxaborol-6-yloxy)pyrazine-2-carboxamide To a solution of 5-chloro-N-(2-hydroxy-1-phenylethyl)pyrazine-2-carboxamide (277 mg, 1 mmol, 1 eq) in DMF (3.33 mL, c=0.3) were added 7-methybenzo[c][1,2]oxaborole-1,6(3H)-diol (164 mg, 1 mmol, 1 eq) and $Cs_2CO_3$ (650 mg, 2 mmol, 2 eq) at room temperature. The reaction was stirred at 40° C. for 1 h. After completion, the reaction was poured into water (30 mL), adjusted to pH=4 with 2N HCl. The precipitated solid was filtered. The filter cake was washed with EA/PE (1/1 mixture). Then the filter cake was dried in vacuo to give the desired product (130 mg, 32% yield). $^1$H NMR (300 MHz, DMSO-$d_6$): δ 9.07 (s, 1H), 8.90 (d, J=9 Hz, 1H), 8.65 (s, 2H), 7.45-7.20 (m 7H), 5.10-5.00 (m, 2H), 4.98 (s, 2H), 3.85-3.65 (m, 2H), 2.22 (s, 3H) ppm. HPLC purity: 96.7% at 220 nm and 95.7% at 254 nm; Mass: m/z=406 (M+1, ESI+).

Example 17

5-((1-hydroxy-7-methyl-1,3-dihydrobenzo[c][1,2]oxaborol-6-yl)oxy)-N-(1-(hydroxymethyl)cyclopropyl)pyrazine-2-carboxamide

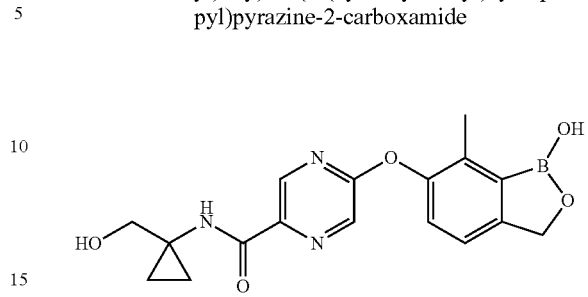

Step 1: Preparation of 5-chloro-N-(1-(hydroxymethyl)cyclopropyl)pyrazine-2-carboxamide To a solution of 5-chloropyrazine-2-carboxylic acid (157 mg, 1 mmol, 1 eq) in NMP (10 mL) was added CMPI (637 mg, 2.5 mmol, 2.5 eq) and then stirred for 0.5 h at room temperature. A solution of (1-aminocyclopropyl)methanol hydrochloride (123 mg, 1 mmol, 1 eq) in NMP (3 mL) and DIPEA (903 mg, 6.8 mmol, 6.8 eq) was added. After completion, the reaction mixture was poured into water (100 mL), adjusted to pH=3 by 1N HCl and extracted with EA (3×50 mL). The combined organic phase was washed with brine, dried over $MgSO_4$, filtered and concentrated in vacuum. The residue was purified by column chromatography to give the desired product (100 mg, 44% yield)

Step 2: Preparation of 5-((1-hydroxy-7-methyl-1,3-dihydrobenzo[c][1,2]oxaborol-6-yl)oxy)-N-(1-(hydroxymethyl)cyclopropyl)pyrazine-2-carboxamide To a solution of 5-chloro-N-(1-(hydroxymethyl)cyclopropyl)pyrazine-2-carboxamide (100 mg, 0.4 mmol, 1 eq) in DMF (1.0 mL) were added 7-methylbenzo[c][1,2]oxaborole-1,6(3H)-diol (72 mg, 0.4 mmol, 1 eq) and $Cs_2CO_3$ (360 mg, 1. mmol, 2.5 eq) at room temperature. The reaction was stirred at 40° C. for 2 h. After completion, the reaction was poured into 1N HCl (20 mL) and extracted with EA (2×20 mL). The combined organic phase was washed with brine, dried over $MgSO_4$, filtered and concentrated in vacuum. The residue was purified by column chromatography to give the desired product (38 mg, 24% yield) as a solid. $^1$H NMR (300 MHz, DMSO-$d_6$): δ 9.07 (s, 1H), 8.67 (s, 1H), 8.64 (s, 1H), 8.57 (s, 1H), 7.30 (d, J=8 Hz, 1H), 7.25 (d, J=8 Hz, 1H), 4.99 (s, 2H), 4.71 (t, J=5.7 Hz, 1H), 3.52 (d, J=5.7 Hz, 2H), 2.21 (s, 3H), 0.78 (s, 4H) ppm. HPLC purity: 96.5% at 220 nm and 99.2% at 254 nm; Mass: m/z=356 (M+1, ESI+).

Example 18

5-(1-hydroxy-7-methyl-1,3-dihydrobenzo[c][1,2]oxaborol-6-yloxy)-N-(1-hydroxybutan-2-yl)pyrazine-2-carboxamide

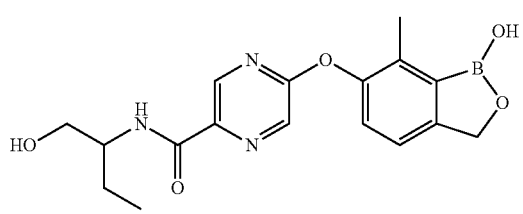 [SMILES: CCC(CO)NC(=O)c1cnc(Oc2ccc3c(c2C)B(O)OC3)cn1]

Step 1: Preparation of 5-chloro-N-(1-hydroxybutan-2-yl)pyrazine-2-carboxamide To a solution of 5-chloropyrazine-2-carboxylic acid (500 mg, 3.16 mmol, 1 eq), TEA (352 mg, 3.47 mmol, 1.1 eq) in DCM (15.8 mL) was added isobutyl chloroformate (944 mg, 10.4 mmol, 1.1 eq). After 10 min, 2-aminobutan-1-ol (338 mg, 3.79 mmol, 1.2 eq) was added at 0° C. The reaction mixture was stirred at room temperature for 10 min. After completion, the reaction was poured into water (100 mL) and extracted with DCM (2×20 mL). The combined organic phase was washed with brine, dried over MgSO$_4$, filtered and concentrated in vacuum. The residue was purified by column chromatography to give the desired product (480 mg, 66% yield) as solid.

Step 2: Preparation of 5-(1-hydroxy-7-methyl-1,3-dihydrobenzo[c][1,2]oxaborol-6-yloxy)-N-(1-hydroxybutan-2-yl)pyrazine-2-carboxamide To a solution of 5-chloro-N-(1-hydroxybutan-2-yl)pyrazine-2-carboxamide (211 mg, 0.92 mmol, 1 eq) in DMF (3 mL, c=0.3) were added 7-methylbenzo[c][1,2]oxaborole-1,6(3H)-diol (166 mg, 1.01 mmol, 1.1 eq) and Cs$_2$CO$_3$ (748 mg, 2.3 mmol, 2.5 eq) at room temperature. The reaction mixture was stirred at 50° C. for 4 h. After completion, the reaction was poured into 2N HCl (20 mL) and extracted with EA (2×10 0 mL). The combined organic phase was washed with brine, dried over MgSO$_4$, filtered and concentrated in vacuum. The residue was purified by column chromatography to give the desired product (247 mg, 75% yield) as a white solid. $^1$H NMR (300 MHz, DMSO-d$_6$): δ 9.08 (s, 1H), 8.66 (s, 1H), 8.60 (s, 1H), 8.22 (d, J=8.7 Hz, 1H), 7.40-7.20 (m, 2H), 4.98 (s, 2H), 4.77 (s, 1H), 4.00-3.80 (m, 1H), 3.60-3.40 (m, 2H), 2.22 (s, 3H), 1.75-1.40 (m, 2H), 1.00-0.80 (m, 3H) ppm. HPLC purity: 95.2% at 220 nm and 97.4% at 254 nm; Mass: m/z=358 (M+1, ESI+).

Example 19

(R)-5-(1-hydroxy-7-methyl-1,3-dihydrobenzo[c][1,2]oxaborol-6-yloxy)-N-(1-hydroxybutan-2-yl)pyrazine-2-carboxamide

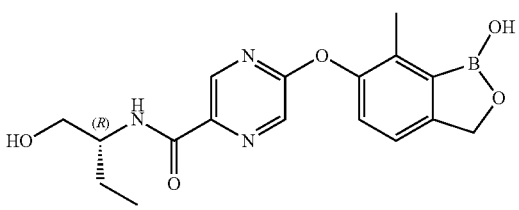

Step 1: Preparation of (R)-5-chloro-N-(1-hydroxybutan-2-yl)pyrazine-2-carboxamide To a solution of 5-chloropyrazine-2-carboxylic acid (1 g, 9.49 mmol, 1 eq), TEA (704 mg, 10.4 mmol, 1.1 eq) in DCM (31.6 mL) were added isobutyl chloroformate (944 mg, 10.4 mmol, 1.1 eq). After 10 min, (R)-2-aminobutan-1-ol (676 mg, 11.4 mmol, 1.2 eq) was added at 0° C. The reaction mixture was stirred at room temperature for 10 min. After completion, the reaction was poured into water (100 mL) and extracted with DCM (2×40 mL). The combined organic phase was washed with brine, dried over MgSO$_4$, filtered and concentrated in vacuum. The residue was purified by column chromatography to give the desired product (740 mg, 51% yield) as a colorless solid.

Step 2: Preparation of (R)-5-(1-hydroxy-7-methyl-1,3-dihydrobenzo[c][1,2]oxaborol-6-yloxy)-N-(1-hydroxybutan-2-yl)pyrazine-2-carboxamide To a solution of (R)-5-chloro-N-(1-hydroxybutan-2-yl)pyrazine-2-carboxamide (500 mg, 2.18 mmol, 1 eq) in DMF (7.3 mL, c=0.3) were added 7-methylbenzo[c][1,2]oxaborole-1,6(3H)-diol (394 mg, 2.4 mmol, 1.1 eq) and Cs$_2$CO$_3$ (1.77 g, 5.45 mmol, 2.5 eq) at room temperature. The reaction was stirred at 50° C. for 3 h. After completion, the reaction was poured into 2N HCl (50 mL) and extracted with EA (2×20 mL). The combined organic phase was washed with brine, dried over MgSO$_4$, filtered and concentrated in vacuum. The residue was purified by column chromatography to give the desired product (460 mg, 59% yield) as a white solid. $^1$H NMR (300 MHz, DMSO-d$_6$): δ 9.08 (s, 1H), 8.66 (s, 1H), 8.61 (s, 1H), 8.23 (d, J=9 Hz, 1H), 7.30 (d, J=8.4 Hz, 1H), 7.25 (d, J=8.4 Hz, 1H), 4.99 (s, 2H), 4.77 (t, J=5.6 Hz, 1H), 3.95-3.80 (m, 1H), 3.50-3.35 (m, 2H), 2.22 (s, 3H), 1.75-1.45 (m, 2H), 0.86 (t, J=7.5 Hz, 3H) ppm. HPLC purity: 100% at 220 nm and 100% at 254 nm; Mass: m/z=358 (M+1, ESI+).

Example 20

5-(1-hydroxy-7-methyl-1,3-dihydrobenzo[c][1,2]oxaborol-6-yloxy)-N-(1-hydroxybut-3-en-2-yl)pyrazine-2-carboxamide

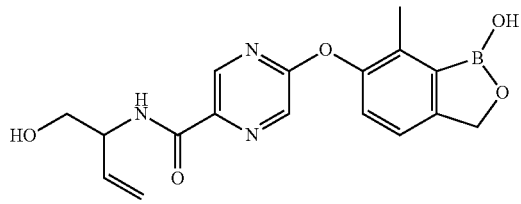 [SMILES: C=CC(CO)NC(=O)c1cnc(Oc2ccc3c(c2C)B(O)OC3)cn1]

Step 1: Preparation of 2-(tert-butyldimethylsilyloxy)ethanol

To a solution of NaH (3.8 g, 159.2 mmol, 1.2 eq) in THF (265 mL) was added ethane-1,2-diol (9.88 g, 159.2 mmol, 1.2 eq). Then the reaction was stirred for 1.5 h. TBSCl (20 g, 132.7 mmol, 1 eq) was added and stirred for 1.5 h. After completion, the reaction was poured into water (150 mL), added 0.8 M K2CO3 (40 mL), extracted with Et$_2$O. The organic phase was washed with brine, dried over MgSO$_4$, filtered and concentrated in vacuum. The residue was purified by column chromatography to give 2-(tert-butyldimethylsilyloxy)ethanol (8.6 g, 36% yield).

Step 2: Preparation of 2-(tert-butyldimethylsilyloxy)acetaldehyde

To a solution of DMSO (7.73 mL, 109 mmol, 2.4 eq) in DCM (130 mL) was added (COCl)$_2$ (4.6 mL in 8 mL DCM) at −78° C. Then reaction was stirred for 30 min. To the reaction mixture was added a solution of pyridine (7.36 mL, 90.85 mmol, 2 eq) and 2-(tert-butyldimethylsilyloxy)ethanol (8 g, 45.42 mmol, 1 eq) in DCM (10 mL). After completion, Et$_3$N (31.6 mL, 227 mmol, 5 eq) was added and stirred for 30 min. Then the reaction was poured into water (100 mL), adjusted to pH=3 with 1N HCl and extracted with EA (3×50 mL). The combined organic phase was washed with brine, dried over MgSO$_4$, filtered and concentrated in vacuum to give 2-(tert-butyldimethylsilyloxy)acetaldehyde (8.3 g, 100% yield).

Step 3: Preparation of (E)-N-(2-(tert-butyldimethylsilyloxy)ethylidene)-2-methylpropane-2-sulfinamide To a solution of 2-(tert-butyldimethylsilyloxy)acetaldehyde (7.9, 45.4 mmol, 1.1 eq) and 2-methylpropane-2-sulfinamide (5 g, 41.25 mmol, 1 eq) in DCM (83 mL) was added Ti(OEt)$_4$ (11.3 g in 20 mL DCM) at room temperature. Then reaction was stirred at 40° C. overnight. After completion, the reaction was poured into sodium bicarbonate solution (200 mL), added diatomite (20 g) and stirred for 0.5 h. The mixture was filtered and extracted with DCM (2×50 mL). The combined organic phase was washed with brine, dried over MgSO$_4$, concentrated in vacuum. The residue was purified by column chromatography to give (E)-N-(2-(tert-butyldimethylsilyloxy)ethylidene)-2-methylpropane-2-sulfinamide (5.1 g, 44% yield).

Step 4: Preparation of N-(1-(tert-butyldimethylsilyloxy)but-3-en-2-yl)-2-methylpropane-2-sulfinamide To a solution of (E)-N-(2-(tert-butyldimethylsilyloxy)ethylidene)-2-methylpropane-2-sulfinamide (2 g, 7.22 mmol, 1 eq) in DCM (36 mL) was added vinylmagnesium bromide (5.4 mL, 10.82 mmol, 1.5 eq) at −78° C. The reaction was stirred for 1 h. After completion, a solution of ammonium chloride was added dropwise, and the mixture was extracted with DCM (2×10 mL). The combined organic phase was washed with brine, dried over MgSO4, filtered and concentrated in vacuum. The residue was purified by column chromatography to give N-(1-(tert-butyldimethylsilyloxy)but-3-en-2-yl)-2-methylpropane-2-sulfinamide (1.2 g, yield 54%).

Step 5: Preparation of 2-aminobut-3-en-1-ol hydrochloride

To a solution of N-(1-(tert-butyldimethylsilyloxy)but-3-en-2-yl)-2-methylpropane-2-sulfinamide (12 g, 3.93 mmol, 1 eq) in MeOH (19.7 mL) was added 4N HCl/MeOH (10 mL). The reaction was stirred at room temperature for 1 h. After completion, the reaction was concentrated directly, washed with EA/PE (1/1 mixture) and dried in vacuum to give 2-aminobut-3-en-1-ol hydrochloride (370 mg, 76% yield).

Step 6: Preparation of 5-chloro-N-(1-hydroxybut-3-en-2-yl)pyrazine-2-carboxamide To a solution of 5-chloropyrazine-2-carboxylic acid (473 mg, 3.0 mol, 1 eq) in NMP (19.9 mL) was added CMPI (1.91 g, 7.5 mmol, 2.5 eq). The reaction was stirred at room temperature for 1 h. Then 2-aminobut-3-en-1-ol hydrochloride (370 mg, 3.0 mmol, 1 eq) and DIPEA (2.32 g, 18.0 mmol, 6 eq) were added and stirred for 1.5 h. And then the reaction was poured into water (200 mL), adjusted to pH=4 with 2N HCl and extracted with EA (2×80 mL). The combined organic phase was washed with brine, dried over MgSO4, filtered and concentrated in vacuum. The residue was purified by column chromatography to give 5-chloro-N-(1-hydroxybut-3-en-2-yl)pyrazine-2-carboxamide (455 mg, yield 66%).

Step 7: Preparation of 5-(1-hydroxy-7-methyl-1,3-dihydrobenzo[c][1,2]oxaborol-6-yloxy)-N-(1-hydroxybut-3-en-2-yl)pyrazine-2-carboxamide To a solution of 5-chloro-N-(1-hydroxybut-3-en-2-yl)pyrazine-2-carboxamide (455 mg, 2.0 mmol, 1 eq) in DMF (10 mL) were added 7-methylbenzo[c][1,2]oxaborole-1,6 (3H)-diol (328 mg, 2.0 mmol, 1 eq) and Cs$_2$CO$_3$(1.3 g, 4 mmol, 2 eq). The reaction was stirred at 40° C. for 2 h. After completion, the reaction was poured into water (120 mL), adjusted to pH=3 with 2N HCl and extracted with EA (2×40 mL). The combined organic phase was washed with brine, dried over MgSO$_4$, filtered and concentrated in vacuum. The residue was purified by column chromatography to give the desired product (260 mg, 36% yield). $^1$H NMR (300 MHz, DMSO-d$_6$): δ 9.08 (s, 1H), 8.67 (s, 1H), 8.63 (s, 1H), 8.46 (d, J=8.7 Hz, 1H), 7.30 (d, J=8.4 Hz, 1H), 7.25 (d, J=8.4 Hz, 1H), 6.00-5.85 (m, 1H), 5.19-5.10 (m, 2H), 4.99 (s, 2H), 4.92 (t, J=5.6 Hz, 1H), 4.60-4.50 (m, 1H), 3.60-3.50 (m, 2H), 2.22 (s, 3H) ppm. HPLC purity: 99.3% at 220 nm and 99.5% at 254 nm; Mass: m/z=356 (M+1, ESI+).

Example 21

(S)-5-(1-hydroxy-7-methyl-1,3-dihydrobenzo[c][1,2] oxaborol-6-yloxy)-N-(1-hydroxybutan-2-yl)pyrazine-2-carboxamide

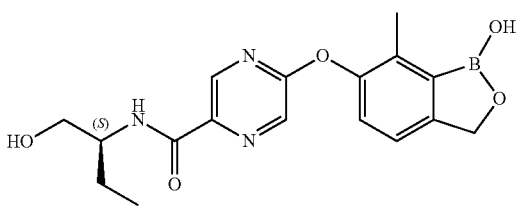

Step 1: Preparation of (S)-5-chloro-N-(1-hydroxybutan-2-yl)pyrazine-2-carboxamide To a solution of 5-chloropyrazine-2-carboxylic acid (1 g, 9.49 mmol, 1 eq) and TEA (704 mg, 10.4 mmol, 1.1 eq) in DCM (31.6 mL) was added isobutyl chloroformate (944 mg, 10.4 mmol, 1.1 eq). The reaction mixture was stirred for 30 min at 0° C., and then (S)-2-aminobutan-1-ol (676 mg, 11.4 mmol, 1.2 eq) was added at 0° C. The reaction mixture was stirred at room temperature for 10 min. After completion, the reaction was poured into water (100 mL) and extracted with DCM (2×40 mL). The combined organic phase was washed with brine, dried over MgSO$_4$, filtered and concentrated in vacuum. The residue was purified by column chromatography to give the desired product (740 mg, 51% yield) as a colorless solid.

Step 2: Preparation of (S)-5-(1-hydroxy-7-methyl-1,3-dihydrobenzo[c][1,2]oxaborol-6-yloxy)-N-(1-hydroxybutan-2-yl)pyrazine-2-carboxamide To a solution of (S)-5-chloro-N-(1-hydroxybutan-2-yl)pyrazine-2-carboxamide 500 mg, 2.18 mmol, 1 eq) in DMF (7.3 mL) were added 7-methylbenzo[c][1,2]oxaborole-1,6(3H)-diol (394 mg, 2.4 mmol, 1.1 eq) and Cs$_2$CO$_3$ (1.77 g, 5.45 mmol, 2.5 eq) at room temperature. The reaction was stirred at 50° C. for 3 h. After completion, the reaction was poured into 2N HCl (50 mL) and extracted with EA (2×20 mL). The combined organic phase was washed with brine, dried over MgSO$_4$, filtered and concentrated in vacuum. The residue was purified by column chromatography to give the desired product (460 mg, 59% yield) as a white solid. $^1$H NMR (300 MHz, DMSO-d$_6$): δ 9.08 (s, 1H), 8.66 (s, 1H), 8.61 (s, 1H), 8.23 (d, J=8.7 Hz, 1H), 7.29 (d, J=8.4 Hz, 1H), 7.25 (d, J=8.4 Hz, 1H), 4.99 (s, 2H), 4.78 (t, J=5 Hz, 1H), 3.95-3.80 (m, 1H), 3.60-3.40 (m, 2H), 2.22 (s, 3H), 1.75-1.45 (m, 2H), 0.86 (t, J=7.4 Hz, 3H) ppm. HPLC purity: 100% at 220 nm and 100% at 254 nm; Mass: m/z=358 (M+1, ESI+).

Example 22

N-(1-cyclopropyl-2-hydroxyethyl)-5-(1-hydroxy-7-methyl-1,3-dihydrobenzo[c][1,2]oxaborol-6-yloxy)pyrazine-2-carboxamide

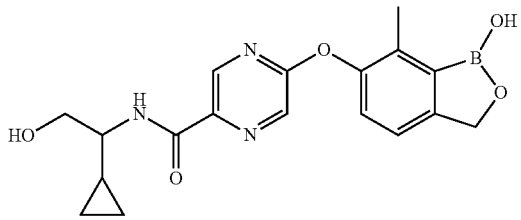 [SMILES: Cc1c(Oc2cnc(C(=O)NC(CO)C3CC3)cn2)ccc2c1B(O)OC2]

Step 1: Preparation of (E)-N-(cyclopropylmethylene)-2-methylpropane-2-sulfinamide To a solution of cyclopropanecarbaldehyde (7.0 g, 99.12 mmol, 1.2 eq) in DCM (138 mL) were added Ti(OEt)$_4$ (22.6 g, 99.12 mmol, 1.2 eq) and 2-methylpropane-2-sulfinamide (10 g, 82.6 mmol, 1 eq) at room temperature. The reaction was stirred at 50° C. overnight. After completion, the reaction was poured into Sq NaHCO$_3$ (138 mL) and diatomite (30 g) with good stirring for 0.5 h. The reaction mixture was filtered and separated. Then, the organic phase was washed with brine, dried over MgSO$_4$, filtered and concentrated in vacuum to give the desired product (12.5 g, 87% yield) as oil.

Step 2 and 3: Preparation of N-(1-cyclopropyl-2-(isopropoxydimethylsilyl)ethyl)-2-methylpropane-2-sulfinamide To a mixture of Mg (2.86 g, 119.16 mmol, 1.65 eq) in THF (75 mL) were added I$_2$ (40 mg) and (chloromethyl)(isopropoxy)dimethylsilane (6.0 g, 36.11 mmol, 0.5 eq) under N$_2$. The reaction was stirred at 100° C. for 1 h, and then additional (chloromethyl)(isopropoxy)dimethylsilane (12 g, 72.22 mmol, 1.0 eq) was added. The reaction was stirred at 85° C. for 2 h. After completion, a solution of (E)-N-(cyclopropylmethylene)-2-methylpropane-2-sulfinamide (12.5 g, 72.22 mmol, 1.0 eq) in THF (37.5 mL) was added into the reaction mixture at −20° C. under N$_2$. The reaction was stirred at room temperature for 1 h. After completion, the reaction was poured into water (300 mL) and extracted with EA (3×100 mL). The combined organic phase was washed with brine, dried over MgSO$_4$, filtered and concentrated in vacuum to give the desired product (22.5 g, 100% yield) as oil.

Step 4: Preparation of N-(1-cyclopropyl-2-hydroxyethyl)-2-methylpropane-2-sulfinamide To a solution of N-(1-cyclopropyl-2-(isopropoxydimethylsilyl)ethyl)-2-methylpropane-2-sulfinamide (22.3 g, 73.07 mmol, 1 eq) in mixed solution (MeOH: 53.5 mL; THF: 53.5 mL) were added KHCO$_3$ (7.32 g, 73.07 mmol, 1 eq), KF (8.5 g, 146.14 mmol, 2 eq) and H$_2$O$_2$ (22.3 mL) under N$_2$ at 0° C. The reaction was stirred at 45° C. for 2 h. After completion, the reaction was poured into water (300 mL) and extracted with EA (3×100 mL). The combined organic phase was washed with brine, dried over MgSO$_4$, filtered and concentrated in vacuum. The residue was purified by column chromatography to give the desired product (10 g, 67% yield) as a white solid.

Step 5: Preparation of 2-amino-2-cyclopropylethanol hydrochloride

To a solution of N-(1-cyclopropyl-2-hydroxyethyl)-2-methylpropane-2-sulfinamide (2 g, 9.75 mmol) in MeOH (48.7 mL) was added HCl (24 mL) at 0° C. The reaction was stirred at room temperature for 2 h. After completion, the reaction was concentrated in vacuum to give the desired product (1.3 g, 100% yield) as a white solid.

Step 6: Preparation of 5-chloro-N-(1-cyclopropyl-2-hydroxyethyl)pyrazine-2-carboxamide To a solution of 5-chloropyrazine-2-carboxylic acid (1.73 g, 10.95 mmol, 1 eq) and CMPI (7 g, 27.375 mmol, 2.5 eq) in NMP (50 mL) was added a solution of DIPEA (8.5 g, 65.7 mmol, 6 eq) and 2-amino-2-cyclopropylethanol hydrochloride (1.8 g, 13.13 mmol, 1.2 eq) in NMP (23 mL) at room temperature. The reaction was stirred at room temperature overnight. After completion, the reaction was poured into water (600 mL) and extracted with EA (3×200 mL). The combined organic phase was washed with brine, dried over $MgSO_4$, filtered and concentrated in vacuum. The residue was purified by column chromatography to give the desired product (1.3 g, 50% yield) as a white solid.

Step 7: Preparation of N-(1-cyclopropyl-2-hydroxyethyl)-5-(1-hydroxy-7-methyl-1,3-dihydrobenzo[c][1,2]oxaborol-6-yloxy)pyrazine-2-carboxamide To a solution of 5-chloro-N-(1-cyclopropyl-2-hydroxyethyl)pyrazine-2-carboxamide (150 mg, 0.91 mmol, 1 eq) in DMF (5 mL) were added 7-methylbenzo[c][1,2]oxaborole-1,6(3H)-diol (250 mg, 1.0 mmol, 1.1 eq) and $Cs_2CO_3$ (0.74 g, 2.27 mmol, 2.5 eq) at room temperature. The reaction mixture was stirred at 50° C. for 2 h. After completion, the reaction was poured into 2N HCl (50 mL) and extracted with EA (3×20 mL). The combined organic phase was washed with brine, dried over $MgSO_4$, filtered and concentrated in vacuum. The residue was purified by column chromatography to give the desired product (20 mg, 7% yield) as a white solid. $^1$H NMR (300 MHz, DMSO-$d_6$): δ 9.08 (s, 1H), 8.66 (s, 1H), 8.62 (s, 1H), 8.45-8.35 (m, 1H), 7.40-7.20 (m, 2H), 4.99 (s, 2H), 4.85-4.75 (m, 1H), 3.70-3.50 (m, 2H), 3.50-3.30 (m, 1H), 2.22 (s, 3H), 1.10-1.00 (m, 1H), 0.50-0.20 (m, 4H) ppm. HPLC purity: 95.8% at 220 nm and 96.4% at 254 nm; Mass: m/z=370 (M+1, ESI+).

Example 23

(S)—N-(1-hydroxy-3-methylbutan-2-yl)-5-(1-hydroxy-7-methyl-1,3-dihydrobenzo[c][1,2]oxaborol-6-yloxy)pyrazine-2-carboxamide

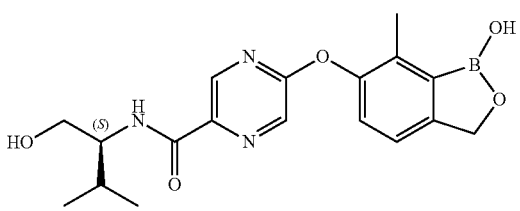

Step 1: Preparation of (S)-5-chloro-N-(1-hydroxy-3-methylbutan-2-yl)pyrazine-2-carboxamide To a solution of 5-chloropyrazine-2-carboxylic acid (250 mg, 1.58 mmol, 1 eq) in NMP (7.9 mL) was added CMPI (1.1 g, 3.96 mmol, 2.5 eq). The reaction was stirred at room temperature for 2 h. Then (S)-2-amino-3-methylbutan-1-ol (163 mg, 1.58 mmol, 1 eq) and DIPEA (1.23 g, 9.49 mmol, 6 eq) were added and stirred for 1 h. After completion, the reaction was poured into water (400 mL), adjusted to pH=4 with 2N HCl and extracted with EA (2×100 mL). The combined organic phase was washed with brine, dried over $MgSO_4$, evaporated and purified by column chromatography to give (S)-5-chloro-N-(1-hydroxy-3-methylbutan-2-yl)pyrazine-2-carboxamide (245 mg, 64% yield).

Step 2: Preparation of (S)—N-(1-hydroxy-3-methylbutan-2-yl)-5-(1-hydroxy-7-methyl-1,3-dihydrobenzo[c][1,2]oxaborol-6-yloxy)pyrazine-2-carboxamide To a solution of (S)-5-chloro-N-(1-hydroxy-3-methylbutan-2-yl)pyrazine-2-carboxamide (134 mg, 0.55 mmol, 1.1 eq) in DMF (5 mL) were added 7-methybenzo[c][1,2]oxaborole-1,6(3H)-diol (82 mg, 0.5 mmol, 1 eq) and $Cs_2CO_3$ (325.8 mg, 1 mmol, 2 eq) at room temperature. The reaction was stirred at 50° C. for 1 h. After completion, the reaction was poured into water (250 mL), adjusted to pH=4 with 2N HCl. The precipitated solid was filtered. The filtrate was purified by column chromatography and then recrystallized to give the desired product (48 mg, 36% yield). $^1$H NMR (300 MHz, DMSO-$d_6$): δ 9.08 (s, 1H), 8.67 (s, 1H), 8.62 (s, 1H), 8.20-8.10 (m, 1H), 7.40-7.20 (m, 2H), 4.99 (s, 2H), 4.80-4.70 (m, 1H), 3.85-3.70 (m, 1H), 3.65-3.45 (m, 2H), 2.22 (s, 3H), 2.02-1.88 (m, 1H), 0.92 (d, J=6.6 Hz, 3H), 0.87 (d, J=6.6 Hz, 3H) ppm. HPLC purity: 99.8% at 220 nm and 99.6% at 254 nm; Mass: m/z=372 (M+1, ESI+).

Example 24

(R)—N-(1-cyclopropyl-2-hydroethyl)-5-(1-hydroxy-7-methyl-1,3-dihydrobenzo[c][1,2]oxaborol-6-yloxy)pyrazine-2-carboxamide

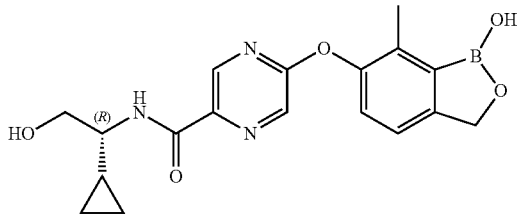

Step 1: Preparation of (S,E)-N-(cyclopropylmethylene)-2-methylpropane-2-sulfinamide To a solution of cyclopropanecarbaldehyde (7.0 g, 99.12 mmol, 1.2 eq) in DCM (138 mL) were added Ti(OEt)$_4$ (22.6 g, 99.12 mmol, 1.2 eq) and (S)-2-methylpropane-2-sulfinamide (10 g, 82.6 mmol, 1 eq) at room temperature. The reaction was stirred at 50° C. overnight. After completion, the reaction was poured into saturated NaHCO$_3$ (138 mL) and diatomite (30 g) with good stirring for 0.5 h. The mixture was filtered and separated. Then, the organic phase was washed with brine, dried over MgSO$_4$, filtered and concentrated in vacuum to give the desired product (12.5 g, 87% yield) as oil.

Step 2 and 3: Preparation of (S)—N—((R)-1-cyclopropyl-2-(isopropoxydimethylsilyl)ethyl)-2-methylpropane-2-sulfinamide To a mixture of Mg (2.86 g, 119.16 mmol, 1.65 eq) in THF (75 mL) were added I$_2$ (40 mg) and (chloromethyl)(isopropoxy)dimethylsilane (6.0 g, 36.11 mmol, 0.5 eq) under N$_2$. The reaction was stirred at 100° C. for 1 h, and then additional (chloromethyl)(isopropoxy)dimethylsilane (12 g, 72.22 mmol, 1.0 eq) was added dropwise slowly. The reaction was stirred at 85° C. for 2 h. After completion, a solution of (S,E)-N-(cyclopropylmethylene)-2-methylpropane-2-sulfinamide (12.5 g, 72.22 mmol, 1.0 eq) in THF (37.5 mL) was added into the reaction mixture at −20° C. under N$_2$. The mixture was stirred at room temperature for 1 h. After completion, the reaction mixture was poured into water (300 mL) and extracted with EA (3×100 mL). The combined organic phase was washed with brine, dried over MgSO$_4$, filtered and concentrated in vacuum to give the desired product (22.5 g, 100% yield) as oil.

Step 4: Preparation of (S)—N—((R)-1-cyclopropyl-2-hydroxyethyl)-2-methylpropane-2-sulfinamide To a solution of (S)—N—((R)-1-cyclopropyl-2-(isopropoxydimethylsilyl)ethyl)-2-methylpropane-2-sulfinamide (22.3 g, 73.07 mmol, 1 eq) in mixed solution (MeOH: 53.5 mL; THF: 53.5 mL) were added KHCO$_3$ (7.32 g, 73.07 mmol, 1 eq), KF (8.5 g, 146.14 mmol, 2 eq) and H$_2$O$_2$(22.3 mL) under N$_2$ at 0° C. The reaction was stirred at 45° C. for 2 h. After completion, the reaction was poured into water (300 mL) and extracted with EA (3×100 mL). The combined organic phase was washed with brine, dried over MgSO$_4$, filtered and concentrated in vacuum. The residue was purified by column chromatography to give the desired product (10 g, 67% yield) as a white solid.

Step 5: Preparation of (R)-2-amino-2-cyclopropylethanol hydrochloride

To a solution of (S)—N—((R)-1-cyclopropyl-2-hydroxyethyl)-2-methylpropane-2-sulfinamide (2 g, 9.75 mmol, 1 eq) in MeOH (48.7 mL) was added HCl (24 mL) at 0° C. The reaction was stirred at room temperature for 2 h. After completion, the reaction was concentrated in vacuum to give the desired product (1.3 g, 100% yield) as a white solid that was used in the next step without further purification.

Step 6: Preparation of (R)-5-chloro-N-(1-cyclopropyl-2-hydroxyethyl)pyrazine-2-carboxamide To a solution of 5-chloropyrazine-2-carboxylic acid (1.73 g, 10.95 mmol, 1 eq) and CMPI (7 g, 27.375 mmol, 2.5 eq) in NMP (73 mL) was added a solution of DIPEA (8.5 g, 65.7 mmol, 6 eq). In 30 min, (R)-2-amino-2-cyclopropylethanol hydrochloride (1.8 g, 13.13 mmol, 1.2 eq) was added at room temperature. The reaction was stirred overnight, poured into water (600 mL) and extracted with EA (3×200 mL). The combined organic phase was washed with brine, dried over MgSO$_4$, filtered and concentrated in vacuum. The residue was purified by column chromatography to give the desired product (1.3 g, 50% yield) as a white solid.

Step 7: Preparation of (R)—N-(1-cyclopropyl-2-hydroxyethyl)-5-(1-hydroxy-7-methyl-1,3-dihydrobenzo[c][1,2]oxaborol-6-yloxy)pyrazine-2-carboxamide To a solution of (R)-5-chloro-N-(1-cyclopropyl-2-hydroxyethyl)pyrazine-2-carboxamide (1.0 g, 4.15 mmol, 1 eq) in DMF (21 mL) were added 7-methylbenzo[c][1,2]oxaborole-1,6(3H)-diol (0.75 g, 4.57 mmol, 1.1 eq) and Cs$_2$CO$_3$ (3.4 g, 10.38 mmol, 2.5 eq) at room temperature. The reaction was stirred at 50° C. for 2 h. After completion, the reaction was poured into 2N HCl (200 mL) and extracted with EA (3×60 mL). The combined organic phase was washed with brine, dried over MgSO$_4$, filtered and concentrated in vacuum. The residue was purified by column chromatography and prep-HPLC to give the desired product (180 mg, 12% yield) as a white solid. $^1$H NMR (300 MHz, DMSO-d$_6$): δ 9.07 (s, 1H), 8.64 (s, 1H), 8.60 (s, 1H), 8.37 (d, J=9.0 Hz, 1H), 7.28 (d, J=8.1 Hz, 1H), 7.24 (d, J=8.1 Hz, 1H), 4.97 (s, 2H), 4.78 (t, 1H), 3.65-3.50 (m, 2H), 3.40-3.30 (m, 1H), 2.20 (s, 3H), 1.10-1.00 (m, 1H), 0.50-0.20 (m, 4H) ppm. HPLC purity: 99.6% at 220 nm and 99.7% at 254 nm; Chiral HPLC purity: 100% at 240 nm; Mass: m/z=370 (M+1, ESI+) and 392 (M+23, ESI+).

Example 25

(R)—N-(1-hydroxy-3-methylbutan-2-yl)-5-(1-hydroxy-7-methyl-1,3-dihydrobenzo[c][1,2]oxaborol-6-yloxy)pyrazine-2-carboxamide

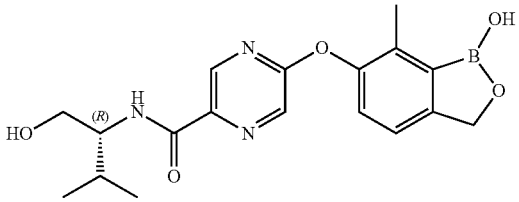

Step 1: Preparation of (R)-5-chloro-N-(1-hydroxy-3-methylbutan-2-yl)pyrazine-2-carboxamide To a solution of 5-chloropyrazine-2-carboxylic acid (250 mg, 1.58 mmol, 1 eq) in NMP (7.9 mL, c=0.20) was added CMPI (1. lg, 3.96 mmol, 2.5 eq). The reaction was stirred at room temperature for 2 h. Then (R)-2-amino-3-methylbutan-1-ol (163 mg, 1.58 mmol, 1 eq) and DIPEA (1.23 g, 9.49 mmol, 6 eq) were added and stirred for 1.5 h. After completion, the reaction was poured into water (80 mL) and extracted with EA (3×25 mL). The combined organic phase was washed with brine, dried over MgSO$_4$, evaporated and purified by column chromatography to give the (R)-5-chloro-N-(1-hydroxy-3-methylbutan-2-yl)pyrazine-2-carboxamide (250 mg, 65% yield).

Step 2: Preparation of (R)—N-(1-hydroxy-3-methylbutan-2-yl)-5-(1-hydroxy-7-methyl-1,3-dihydrobenzo[c][1,2]oxaborol-6-yloxy)pyrazine-2-carboxamide To a solution of (R)-5-chloro-N-(1-hydroxy-3-methylbutan-2-yl)pyrazine-2-carboxamide (243 mg, 1 mmol, 1 eq) in DMF (5 mL) were added 7-methybenzo[c][1,2]oxaborole-1,6(3H)-diol (164 mg, 1 mmol, 1 eq) and Cs$_2$CO$_3$ (650 mg, 2 mmol, 2 eq) at room temperature. The reaction mixture was stirred at 50° C. for 1 h. After completion, the mixture was poured into water (50 mL), adjusted to pH=5 with 2N HCl and extracted with EA (3×50 mL). The combined organic phase was washed with brine, dried over MgSO$_4$, filtered and concentrated in vacuum. The residue was purified by column chromatography and recrystallized to give the desired product (74 mg, 20% yield). $^1$H NMR (500 MHz, DMSO-d$_6$): δ 9.08 (s, 1H), 8.67 (s, 1H), 8.62 (s, 1H), 8.13 (d, J=9.5 Hz, 1H), 7.29 (d, J=8 Hz 1H), 7.26 (d, J=8 Hz, 1H), 4.99 (s, 2H), 4.72 (t, J=5.5 Hz, 1H), 3.82-3.77 (m, 1H), 3.65-3.49 (m, 2H), 2.22 (s, 3H), 1.98-1.92 (m, 1H), 0.92 (d, J=6.5 Hz, 3H), 0.87 (s, J=6.5 Hz, 3H) ppm. HPLC purity: 100% at 220 nm and 100% at 254 nm; Chiral purity: 100% at 240 nm; Mass: m/z=372 (M+1, ESI+).

Example 26

(R)—N-(2-hydroxy-1-phenylethyl)-5-(1-hydroxy-7-methyl-1,3-dihydrobenzo[c][1,2]oxaborol-6-yloxy)pyrazine-2-carboxamide

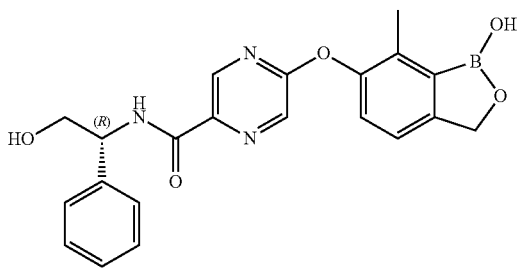

Step 1: Preparation of (R)-5-chloro-N-(2-hydroxy-1-phenylethyl)pyrazine-2-carboxamide To a solution of 5-chloropyrazine-2-carboxylic acid (500 mg, 3.16 mmol, 1 eq) in NMP (21.1 mL) was added CMPI (2.02 g, 7.91 mmol, 2.5 eq). The reaction was stirred at room temperature for 2 h. Then (R)-2-amino-2-phenylethanol (434 mg, 3.16 mmol, 1 eq) and DIPEA (2.45 g, 19 mmol, 6 eq) were added and stirred for 1.5 h. After completion, the reaction was poured into water (500 mL), adjusted to pH=4 with 2N HCl and extracted with EA (2×150 mL). The combined organic phase was washed with brine, dried over MgSO$_4$, filtered and concentrated in vacuum to give (R)-5-chloro-N-(2-hydroxy-1-phenylethyl)pyrazine-2-carboxamide (640 mg, 72% yield).

Step 2: Preparation of (R)—N-(2-hydroxy-1-phenylethyl)-5-(1-hydroxy-7-methyl-1,3dihydrobenzo[c][1,2]oxaborol-6-yloxy)pyrazine-2-carboxamide To a solution of (R)-5-chloro-N-(2-hydroxy-1-phenylethyl)pyrazine-2-carboxamide (554 mg, 2 mmol, 1 eq) in DMF (10 mL) were added 7-methylbenzo[c][1,2]oxaborole-1,6(3H)-diol (316 mg, 2 mmol, 1 eq) and Cs$_2$CO$_3$ (977 mg, 3 mmol, 1.5 eq) at room temperature. The reaction was stirred at 50° C. for 0.5 h. After completion, the reaction was poured into ice-water (150 mL), adjusted to pH=4 with 2N HCl and extracted with EA (2×50 mL). The combined organic phase was washed with brine, dried over MgSO$_4$, filtered and concentrated in vacuum. The residue was purified by column chromatography to give the desired product (270 mg, 33% yield). $^1$H NMR (300 MHz, DMSO-d$_6$): δ 9.08 (s, 1H), 8.92 (d, J=8.4 Hz, 1H), 8.65 (s, 1H), 8.64 (s, 1H), 7.40-7.23 (m, 7H), 5.10-5.00 (m, 2H) 4.98 (s, 2H), 3.85-3.70 (m, 2H), 2.22 (s, 3H) ppm. HPLC purity: 99.9% at 220 nm and 99.8% at 254 nm; Chiral HPLC purity: 100% at 240 nm; Mass: m/z=406 (M+1, ESI+).

Example 27

(R)—N-(1-hydroxy-3-phenylpropan-2-yl)-5-(1-hydroxy-7-methyl-1,3-dihydrobenzo[c][1,2]oxaborol-6-yloxy)pyrazine-2-carboxamide

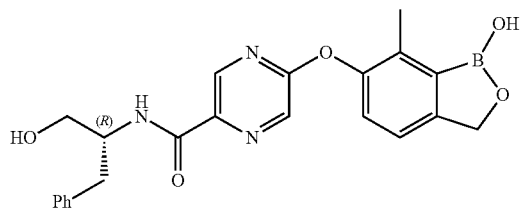

Step 1: Preparation of (R)-6-chloro-N-(1-hydroxy-3-phenylpropan-2-yl)pyrazine-2-carboxamide To a solution of 5-chloropyrazine-2-carboxylic acid (500 mg, 3.2 mmol, 1 eq) in NMP (21 mL) was added CMPI (352 mg, 3.5 mmol, 1.1 eq) with stirring for 30 min. And then (R)-2-amino-3-phenylpropan-1-ol (478 mg, 3.16 mmol, 1 eq) and DIPEA (2.78 g, 21.5 mmol, 6 eq) were added. The solution was stirred at room temperature for 2 h. After completion, the reaction mixture was adjusted to pH=3 by 2N HCl and extracted with DCM (2×30 mL). The combined organic phase was washed with brine (50 mL), dried over anhydrous Na$_2$SO$_4$ and filtered. The residue after rotary evaporation was purified by column chromatography to give the desired product (650 mg, 71% yield) as a white solid.

Step 2: Preparation of (R)—N-(1-hydroxy-3-phenylpropan-2-yl)-5-(1-hydroxy-7-methyl-1,3-dihydrobenzo[c][1,2]oxaborol-6-yloxy) pyrazine-2-carboxamide To a solution of (R)-6-chloro-N-(1-hydroxy-3-phenylpropan-2-yl)pyrazine-2-carboxamide (145 mg, 0.5 mmol, 1.0 eq) and 7-methylbenzo[c][1,2]oxaborole-1,6(3H)-diol (79 mg, 0.46 mmol, 1.0 eq) in DMF (2.5 mL, c=0.2) was added Cs$_2$CO$_3$ (244 mg, 0.75 mmol, 1.5 eq). The reaction mixture was stirred at 50° C. for 2 h. After completion, the mixture was adjusted to pH=3 using IN HCl and extracted with DCM (2×30 mL). The combined organic phase was washed with brine (20 mL), dried over anhydrous Na$_2$SO$_4$ and filtered. The residue after rotary evaporation was purified by column chromatography to give the desired product (126 mg, 60% yield) as a white solid. $^1$H NMR (300 MHz, DMSO-d$_6$): δ 9.08 (s, 1H), 8.60 (s, 2H), 8.39 (d, J=8.4 Hz, 1H), 7.33-7.22 (m, 6H), 7.21-7.13 (m, 1H), 4.98 (s, 2H), 4.93 (t, 1H), 4.25-4.15 (m, 1H), 3.52-3.41 (m, 2H), 2.98-2.84 (m, 2H), 2.21 (s, 3H) ppm. HPLC purity: 98.7% at 220 nm and 100% at 254 nm; Chiral Purity: 100% at 240 nm; Mass: m/z=420 (M+1, ESI+).

Example 28

(R)-5-(1-hydroxy-7-methyl-1,3-dihydrobenzo[c][1,2]oxaborol-6-yloxy)-N-(1-hydroxyhexan-2-yl)pyrazine-2-carboxamide

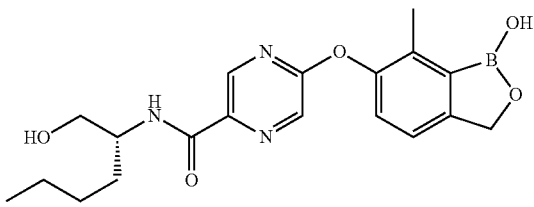 [SMILES: CCCC[C@H](CO)NC(=O)c1cnc(Oc2ccc3c(c2C)B(O)OC3)cn1]

Step 1: Preparation of (R)-2-aminohexan-1-ol

To a solution of (R)-2-aminohexanoic acid (10 g, 76.2 mmol, 1 eq) in THF (200 mL) was added NaBH$_4$ (6.9 g, 182.9 mmol, 2.4 eq) at 0° C. under N$_2$. A solution of I$_2$ (19.3 g, 76.2 mmol, 1 eq) in THF (54 mL) was added dropwise into reaction for 40 min until no gas was produced. The reaction mixture was stirred overnight at 70° C. After completion, MeOH was added dropwise into the reaction mixture until it was clear. The reaction was added 20% KOH (150 mL) and stirred for 4 h. The reaction was diluted with H$_2$O (100 mL), extracted with DCM (3×150 mL). The organic phase was washed with brine and dried over anhydrous Na$_2$SO$_4$. The reaction mixture was concentrated to give the desired product (R)-2-aminohexan-1-ol (8.8 g, 99% yield).

Step 2: Preparation of (R)-2-aminohexan-1-ol hydrochloride

To a solution of (R)-2-aminohexan-1-ol (9 g, 76.2 mmol, 1 eq) in MeOH (160 mL) was added 4N HCl/MeOH (42 mL), stirred at room temperature for 40 min. The residue after rotary evaporation was wished with 40% EA/PE. The precipitated solid was filtered to give (R)-2-aminohexan-1-ol hydrochloride (11 g, 95% yield).

Step 3: Preparation of (R)-5-chloro-N-(1-hydroxyhexan-2-yl)pyrazine-2-carboxamide To a solution of 5-chloropyrazine-2-carboxylic acid (1.278 g, 8.1 mmol, 1 eq) in NMP (54 mL) was added CMPI (5.17 g, 20.2 mmol, 2.5 eq) with stirring under N$_2$. In 30 min, a solution of (R)-2-aminohexan-1-ol hydrochloride (1 g, 8.1 mmol, 1 eq) in NMP (4 mL) was added. The reaction was stirred at room temperature for 2 hours. After completion, the reaction was diluted with H$_2$O (800 mL), adjusted to pH 3-4 with 1N HCl, extracted with EA (2×150 mL). The organic phase was washed with brine (3×600 mL) and dried over anhydrous Na$_2$SO$_4$. The residue after rotary evaporation was purified by column chromatography to give the desired product (1.73 g, 99% yield).

Step 4: Preparation of (R)-5-(1-hydroxy-7-methyl-1,3-dihydrobenzo[c][1,2]oxaborol-6-yloxy)-N-(1-hydroxyhexan-2-yl) pyrazine-2-carboxamide To a solution of (R)-5-chloro-N-(1-hydroxyhexan-2-yl)pyrazine-2-carboxamide (500 mg, 1.8 mmol, 1 eq) in DMF (9 mL, c=0.2) were added Cs$_2$CO$_3$ (1.17 g, 3.6 mmol, 2 eq), benzo[c][1,2]oxaborole-1, 6(3H)-diol (1.17 g, 7.16 mmol, 1 eq). The reaction was stirred at 50° C. for 2 h. After completion, the reaction was diluted with H$_2$O (200 mL), adjusted to pH 3-4 with 1N HCl to give a solid precipitation, filtered. The residue after rotary evaporation was purified by column chromatography to give the desired product (600 mg, 23% yield). $^1$H NMR (300 MHz, DMSO-d$_6$): δ 9.07 (s, 1H), 8.66 (s, 1H), 8.60 (s, 1H), 8.23 (d, J=9 Hz, 1H), 7.29 (d, J=8.4 Hz, 1H), 7.25 (d, J=8.4 Hz, 1H), 4.99 (s, 2H), 4.77 (t, 1H), 3.98-3.85 (m, 1H), 3.55-3.35 (m, 2H), 2.22 (s, 3H), 1.70-1.42 (m, 2H), 1.35-1.15 (m, 4H), 0.84 (m, 3H) ppm; HPLC purity: 99.2% at 220 nm and 98.9% at 254 nm; Chiral HPLC purity: 100% at 240 nm; Mass: m/z=386.2 (M+1, ESI+).

Example 29

(S)-5-(1-hydroxy-7-methyl-1,3-dihydrobenzo[c][1,2]oxaborol-6-yloxy)-N-(1-hydroxybut-3-en-2-yl)pyrazine-2-carboxamide

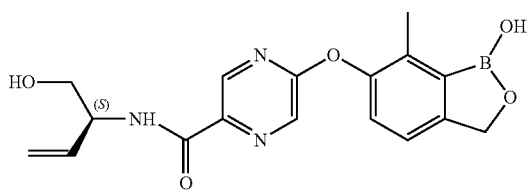

The racemic mixture 5-(1-hydroxy-7-methyl-1,3-dihydrobenzo[c][1,2]oxaborol-6-yloxy)-N-(1-hydroxybut-3-en-2-yl)pyrazine-2-carboxamide (330 mg) was separated by chiral column chromatography to give the desired product (S)-5-(1-hydroxy-7-methyl-1,3-dihydrobenzo[c][1,2]oxaborol-6-yloxy)-N-(1-hydroxybut-3-en-2-yl)pyrazine-2-carboxamide (110 mg) and the other enantiomer. $^1$H NMR (300 MHz, DMSO-d$_6$): δ 9.07 (s, 1H), 8.65 (s, 1H), 8.61 (s, 1H), 8.44 (d, J=8.7 Hz, 1H), 7.28 (d, J=8.4 Hz, 1H), 7.25 (d, J=8.4 Hz, 1H), 5.98-5.86 (m, 1H), 5.19-5.06 (m, 2H), 4.97 (s, 2H), 4.94-4.87 (t, 1H), 4.60-4.40 (m, 1H), 3.45-3.54 (m, 2H), 2.20 (s, 3H) ppm; HPLC purity: 99% at 220 nm and 98.4% at 254 nm; Chiral HPLC purity: 100% at 240 nm; Mass: m/z=356 (M+1, ESI+).

Example 30

(R)-5-(1-hydroxy-7-methyl-1,3-dihydrobenzo[c][1,2]oxaborol-6-yloxy)-N-(1-hydroxybut-3-en-2-yl)pyrazine-2-carboxamide

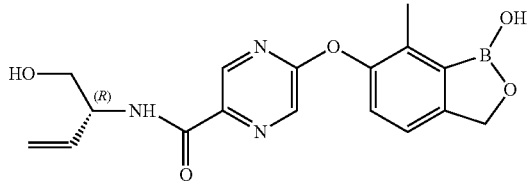

The racemic mixture 5-(1-hydroxy-7-methyl-1,3-dihydrobenzo[c][1,2]oxaborol-6-yloxy)-N-(1-hydroxybut-3-en-2-yl)pyrazine-2-carboxamide (330 mg) was separated by chiral column chromatography to give the desired product (R)-5-(1-hydroxy-7-methyl-1,3-dihydrobenzo[c][1,2]oxaborol-6-yloxy)-N-(1-hydroxybut-3-en-2-yl)pyrazine-2-carboxamide (110 mg) and the other enantiomer. $^1$H NMR (300 MHz, DMSO-$d_6$): δ 9.07 (s, 1H), 8.67 (s, 1H), 8.62 (s, 1H), 8.45 (d, J=8.7 Hz, 1H), 7.29 (d, J=8.4 Hz, 1H), 7.26 (d, J=8.4 Hz, 1H), 5.97-5.90 (m, 1H), 5.17-5.10 (m, 2H), 4.99 (s, 2H), 4.91 (t, J=5.5 Hz, 1H), 4.55-4.52 (m, 1H), 3.58-3.53 (m, 2H), 2.22 (s, 3H) ppm; HPLC purity: 99% at 220 nm and 98.4% at 254 nm; Chiral HPLC purity: 100% at 240 nm; Mass: m/z=356 (M+1, ESI+), 353.9 (M−1, ESI−).

Example 31

(S)—N-(1-cyclopropyl-2-hydroxyethyl)-5-(1-hydroxy-7-methyl-1,3-dihydrobenzo[c][1,2]oxaborol-6-yloxy)pyrazine-2-carboxamide

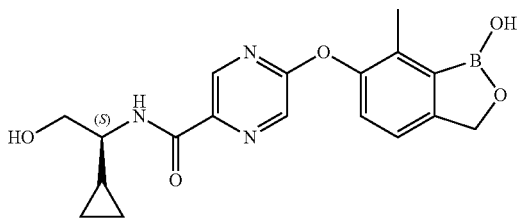

Step 1: Preparation of (R,E)-N-(cyclopropylmethylene)-2-methylpropane-2-sulfinamide To a solution of cyclopropanecarbaldehyde (7.0 g, 99.12 mmol, 1.2 eq) in DCM (138 mL) were added Ti(OEt)$_4$ (22.6 g, 99.12 mmol, 1.2 eq) and (R)-2-methylpropane-2-sulfinamide (10 g, 82.6 mmol, 1 eq) at room temperature. The reaction was stirred at 50° C. overnight. After completion, the reaction was poured into Sq NaHCO$_3$ (138 mL) and diatomite (30 g) with good stirring for 0.5 h. The reaction mixture was filtered and separated. Then, the organic phase was washed with brine, dried over MgSO$_4$, filtered and concentrated in vacuum to give the desired product (12.5 g, 87% yield) as oil.

Step 2 and 3: Preparation of (R)—N—((S)-1-cyclopropyl-2-(isopropoxydimethylsilyl) ethyl)-2-methylpropane-2-sulfinamide To a mixture of Mg (2.86 g, 119.16 mmol, 1.65 eq) in THF (75 mL) were added I$_2$ (40 mg) and (chloromethyl)(isopropoxy)dimethylsilane (6.0 g, 36.11 mmol, 0.5 eq) under N$_2$. The reaction was stirred at 100° C. for 1 h, then additional (chloromethyl)(isopropoxy)dimethylsilane (12 g, 72.22 mmol, 1.0 eq) was added. The reaction was stirred at 85° C. for 2 h. After completion, A solution of (R,E)-N-(cyclopropylmethylene)-2-methylpropane-2-sulfinamide (12.5 g, 72.22 mmol, 1.0 eq) in THF (37.5 mL) was added into the reaction at −20° C. under N$_2$. The reaction was stirred at room temperature for 1 h. After completion, the reaction was poured into water (300 mL) and extracted with EA (3×100 mL). The combined organic phase was washed with brine, dried over MgSO$_4$, filtered and concentrated in vacuum to give the desired product (22.5 g, 102% yield) as oil.

Step 4: Preparation of (R)—N—((S)-1-cyclopropyl-2-hydroxyethyl)-2-methylpropane-2-sulfinamide To a solution of (R)—N—((S)-1-cyclopropyl-2-(isopropoxydimethylsilyl)ethyl)-2-methylpropane-2-sulfinamide (22.3 g, 73.07 mmol, 1 eq) in mixed solution (MeOH: 53.5 mL; THF: 53.5 mL) were added KHCO$_3$ (7.32 g, 73.07 mmol, 1 eq), KF (8.5 g, 146.14 mmol, 2 eq) and H$_2$O$_2$(22.3 mL) under N$_2$ at 0° C. The reaction was stirred at 45° C. for 2 h. After completion, the reaction was poured into water (300 mL) and extracted with EA (3×100 mL). The combined organic phase was washed with brine, dried over MgSO$_4$, filtered and concentrated in vacuum. The residue was purified by column chromatography to give the desired product (10 g, 67% yield) as a white solid.

Step 5: Preparation of (S)-2-amino-2-cyclopropylethanol hydrochloride

To a solution of (R)—N—((S)-1-cyclopropyl-2-hydroxyethyl)-2-methylpropane-2-sulfinamide (2 g, 9.75 mmol, 1 eq) in MeOH (48.7 mL) was added HCl (24 mL) at 0° C. The reaction was stirred at room temperature for 2 h. After completion, the reaction was concentrated in vacuum to give the desired product (1.3 g, 100% yield) as a white solid.

Step 6: Preparation of (S)-5-chloro-N-(1-cyclopropyl-2-hydroxyethyl)pyrazine-2-carboxamide To a solution of 5-chloropyrazine-2-carboxylic acid (1.73 g, 10.95 mmol, 1 eq) and CMPI (7 g, 27.375 mmol, 2.5 eq) in NMP (73 mL) was added a solution of DIPEA (8.5 g, 65.7 mmol, 6 eq) and (S)-2-amino-2-cyclopropylethanol hydrochloride (1.8 g, 13.13 mmol, 1.2 eq) at room temperature. The reaction was stirred overnight. After completion, the reaction was poured into water (600 mL) and extracted with EA (3×200 mL). The combined organic phase was washed with brine, dried over MgSO$_4$, filtered and concentrated in vacuum. The residue was purified by column chromatography to give the desired product (1.3 g, 50% yield) as a white solid.

Step 7: Preparation of (S)—N-(1-cyclopropyl-2-hydroxyethyl)-5-(1-hydroxy-7-methyl-1, 3-dihydrobenzo[c][1,2]oxaborol-6-yloxy)pyrazine-2-carboxamide To a solution of (S)-5-chloro-N-(1-cyclopropyl-2-hydroxyethyl)pyrazine-2-carboxamide (1.0 g, 4.15 mmol, 1 eq) in DMF (21 mL) were added 7-methylbenzo[c][1,2]oxaborole-1,6(3H)-diol (0.75 g, 4.57 mmol, 1.1 eq) and Cs$_2$CO$_3$ (3.4 g, 10.38 mmol, 2.5 eq) at room temperature. The reaction mixture was stirred at 50° C. for 2 h. After completion, the reaction was poured into 2N HCl (200 mL) and extracted with EA (3×60 mL). The combined organic phase was washed with brine, dried over MgSO$_4$, filtered and concentrated in vacuum. The residue was purified by column chromatography and prep-HPLC to give the desired product (98 mg, 6% yield) as a white solid. $^1$H NMR (300 MHz, DMSO-$d_6$): δ 9.07 (s, 1H), 8.66 (s, 1H), 8.61 (s, 1H), 8.37 (d, J=9.0 Hz, 1H), 7.24-7.31 (m, 2H), 4.99 (s, 2H), 4.77-4.81 (m, 1H), 3.59-3.61 (m, 2H), 3.32-3.50 (m, 1H), 2.22 (s, 3H), 1.00-1.20 (m, 1H), 0.20-0.50 (m, 4H) ppm. HPLC purity: 96.6% at 220 nm and 95.9% at 254 nm; Mass: m/z=370 (M+1, ESI+).

Example 32

(S)—N-(1-hydroxy-3-methoxypropan-2-yl)-5-((1-hydroxy-7-methyl-1,3-dihydrobenzo[c][1,2]oxaborol-6-yl)oxy)pyrazine-2-carboxamide

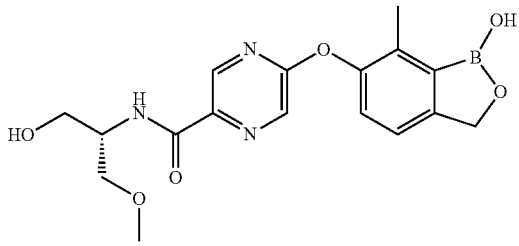 [SMILES: COC[C@H](CO)NC(=O)c1cnc(Oc2ccc3c(c2C)B(O)OC3)cn1]

Step 1: Preparation of Ethyl Benzimidate

To a solution of benzonitrile (10 g, 97 mmol) in $CH_3CH_2OH$ (54 g, 1164 mmol) was added acetyl chloride (61 g, 776 mmol) at 0° C. The reaction mixture was stirred at 25° C. overnight. After removing the solvent, aq $NaHCO_3$ solution was added until no gas generated at 0° C. The solution was extracted with ether (100 mL*3). The combined organic layers were washed with brine, dried over $Na_2SO_4$, filtered and concentrated under reduced pressure to give ethyl benzimidate (11 g, crude) as a yellow oil which was used for next step without further purification. MS: m/z=150.0 (M+1, ESI+).

Step 2: Preparation of (S)-methyl 2-phenyl-4,5-dihydrooxazole-4-carboxylate

To a solution of ethyl benzimidate (8.3 g, 55.8 mmol) in $ClCH_2CH_2Cl$ (30 mL) was added (S)-methyl 2-amino-3-hydroxypropanoate hydrochloride (9.52 g, 61.38 mmol). The reaction mixture was stirred at 84° C. overnight. The solvent was removed under the reduced pressure to give methyl (S)-2-phenyl-4,5-dihydrooxazole-4-carboxylate (10.6 g, crude) as a yellow oil which was used for next step without further purification. MS: m/z=206.0 (M+1, ESI+).

Step 3: Preparation of (R)-(2-phenyl-4,5-dihydrooxazol-4-yl)methanol

To a solution of $LiAlH_4$ (2.9 g, 77.5 mmol) in THF (70 mL) was added methyl (S)-2-phenyl-4,5-dihydrooxazole-4-carboxylate (10.6 g, 51.7 mmol) in THF (70 mL) at 0° C. The reaction mixture was stirred at 70° C. for 2 h, and then several drop of $H_2O$ was added until no gas generated, filtered off and the filtered cake was washed with EA. The combined organic phase was concentrated in vacuum and the residue was purified by Combiflash (EA) to give (R)-(2-phenyl-4,5-dihydrooxazol-4-yl)methanol (2.0 g, 16%, over 3 steps) as a white solid. MS: m/z=178.0 (M+1, ESI+).

Step 4: Preparation of (R)-4-(methoxymethyl)-2-phenyl-4,5-dihydrooxazole

To a solution of (R)-(2-phenyl-4,5-dihydrooxazol-4-yl)methanol (2.0 g, 11.2 mmol) in THF (60 mL) was added NaH (542 mg, 22.4 mmol) at 0° C. After being stirred at 0° C. for 15 min, $CH_3I$ (3.98 g, 28.0 mmol) was added. The reaction mixture was stirred at rt overnight. The solvent was removed and the residue was purified by silica gel column chromatography using PE:EA=5:1 to give (R)-4-(methoxymethyl)-2-phenyl-4,5-dihydrooxazole (1.9 g, yield 88%) as a white solid. MS: m/z=192.0 (M+1, ESI+).

Step 5: Preparation of (S)-2-amino-3-methoxypropan-1-ol hydrochloride

A solution of (R)-4-(methoxymethyl)-2-phenyl-4,5-dihydrooxazole (1.9 g, 11.8 mmol) in aq HCl (4N, 60 mL) was refluxed overnight. After cooled to room temperature, filtered off and the filtrate washed by ether (50 mL*3), then the water layer was lyophilizated to give (S)-2-amino-3-methoxypropan-1-ol hydrochloride (1.5 g, yield 83%) as a white solid. MS: m/z=106.0 (M+1, ESI+).

Step 6: Preparation of (S)-5-chloro-N-(1-hydroxy-3-methoxypropan-2-yl)pyrazine-2-carboxamide A solution of 5-chloropyrazine-2-carboxylic acid (187 mg, 1.18 mmol) and HATU (537 mg, 1.41 mmol) in DMF (5 mL) was stirred at rt for 30 min. Then (S)-2-amino-3-methoxypropan-1-ol hydrochloride (200 mg, 1.41 mmol) and DIPEA (304 mg, 2.35 mmol) were added. The resulting mixture was stirred at rt for 1 h, water (20 mL) was added and the solution was extracted with EA (30 mL*2). The combined organic layers were washed with brine, dried over $Na_2SO_4$, filtered and concentrated under the reduced pressure. The residue was purified by Combiflash (PE:EA=1:1) to give (S)-5-chloro-N-(1-hydroxy-3-methoxypropan-2-yl)pyrazine-2-carboxamide (230 mg, yield 66%) as a yellow solid. MS: m/z=246.0 (M+1, ESI+).

Step 7: Preparation of (S)—N-(1-hydroxy-3-methoxypropan-2-yl)-5-(1-hydroxy-7-methyl-1,3-dihydrobenzo[c][1,2]oxaborol-6-yloxy)pyrazine-2-carboxamide To a solution of (S)-5-chloro-N-(1-hydroxy-3-methoxypropan-2-yl)pyrazine-2-carboxamide (100 mg, 0.408 mmol) and 7-methylbenzo[c][1,2]oxaborole-1,6(3H)-diol (67 mg, 0.408 mmol) in DMF (5 mL) was added $Cs_2CO_3$ (265 mg, 0.816 mmol). The reaction mixture was stirred at 60° C. for 2 h. The mixture was filtered off and the filtrate was purified by Prep-HPLC to give (S)—N-(1-hydroxy-3-methoxypropan-2-yl)-5-(1-hydroxy-7-methyl-1,3-dihydrobenzo[c][1,2]oxaborol-6-yloxy)pyrazine-2-carboxamide (80 mg, yield 52.5%) as a white solid. $^1$H NMR (400 MHz, DMSO-$d_6$) δ 9.10 (s, 1H), 8.67 (s, 1H), 8.62 (s, 1H), 8.25 (d, J=8.8 Hz, 1H), 7.30 (d, J=9 Hz, 2H), 7.26 (d, J=9 Hz, 2H), 4.99 (s, 2H), 4.91 (t, J=5.2 Hz, 1H), 4.17-4.09 (m, 1H), 3.55-3.44 (m, 4H), 3.27 (s, 3H), 2.22 (s, 3H) ppm; HPLC purity: 100% at 220 nm and 100% at 254 nm; Chiral HPLC purity: 100% at 200 nm; MS: m/z=374.1 (M+1, ESI+).

Example 33

(R)-5-(1-hydroxy-7-methyl-1,3-dihydrobenzo[c][1,2]oxaborol-6-yloxy)-N-(4,4,4-trifluoro-1-hydroxybutan-2-yl)pyrazine-2-carboxamide

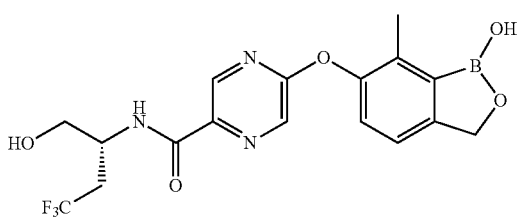 [SMILES: Cc1c(Oc2cnc(C(=O)N[C@@H](CO)CC(F)(F)F)cn2)ccc2c1B(O)OC2]

Step 1: Preparation of 5-chloro-N-(4, 4, 4-trifluoro-1-hydroxybutan-2-yl)pyrazine-2-carboxamide To a solution of 5-chloropyrazine-2-carboxylic acid (372 mg, 2.348 mmol) and HATU (1.07 g, 2.817 mmol) in DMF (10 mL) was added DIPEA (606 mg, 4.969 mmol). The mixture was stirred at rt for 30 min, then 2-amino-4,4,4-trifluorobutan-1-ol hydrochloride (506 mg, 2.817 mmol) was added. The resulting mixture was stirred at rt for 1 h. Water (30 mL) was added and the solution was extracted with EA (50 mL*3). The combined organic layers were washed with brine, dried over $Na_2SO_4$, filtered and concentrated under reduced pressure. The residue was purified by Combiflash (PE:EA=1:1) to give 5-chloro-N-(4,4,4-trifluoro-1-hydroxybutan-2-yl)pyrazine-2-carboxamide (435 mg, 65%) as a white solid. MS: m/z=284.0 (M+1, ESI+).

Step 2: Preparation of 5-(1-hydroxy-7-methyl-1,3-dihydrobenzo[c][1,2]oxaborol-6-yloxy)-N-(4, 4, 4-trifluoro-1-hydroxybutan-2-yl)pyrazine-2-carboxamide To a solution of 5-chloro-N-(4,4,4-trifluoro-1-hydroxybutan-2-yl)pyrazine-2-carboxamide (435 mg, 1.537 mmol) and 7-methylbenzo[c][1,2]oxaborole-1,6(3H)-diol (252 mg, 1.537 mmol) in DMF (10 mL) was added $Cs_2CO_3$ (999 mg, 3.074 mmol). The reaction mixture was stirred at 60° C. overnight, then filtered off and the filtrate was purified by prep-HPLC to give 5-(1-hydroxy-7-methyl-1,3-dihydrobenzo[c][1,2]oxaborol-6-yloxy)-N-(4,4,4-trifluoro-1-hydroxybutan-2-yl)pyrazine-2-carboxamide (360 mg, yield 57%) as a white solid. $^1$H NMR (400 MHz, DMSO-$d_6$): δ 9.09 (s, 1H), 8.72 (d, J=9.2 Hz, 1H), 8.67 (s, 1H), 8.63 (s, 1H), 7.30 (d, J=8.0 Hz, 1H), 7.26 (d, J=8.4 Hz, 1H), 5.11 (t, J=6.0 Hz, 1H), 4.99 (s, 2H), 4.39-4.30 (m, 1H), 3.50-3.34 (m, 2H), 2.74-2.56 (m, 2H), 2.23 (s, 3H) ppm; MS: m/z=412.1 (M+1, ESI+).

Step 3: Preparation of ((R)-5-(1-hydroxy-7-methyl-,3-dihydrobenzo[c][1,2]oxaborol-6-yloxy)-N-(4, 4, 4-trifluoro-1-hydroxybutan-2-yl)pyrazine-2-carboxamide The racemic compound 5-(1-hydroxy-7-methyl-1,3-dihydrobenzo[c][1,2]oxaborol-6-yloxy)-N-(4,4,4-trifluoro-1-hydroxybutan-2-yl)pyrazine-2-carboxamide (360 mg) was separated by chiral HPLC method to give (R)-5-(1-hydroxy-7-methyl-1,3-dihydrobenzo[c][1,2]oxaborol-6-yloxy)-N-(4, 4,4-trifluoro-1-hydroxybutan-2-yl)pyrazine-2-carboxamide (170 mg) and (S)-5-(1-hydroxy-7-methyl-1,3-dihydrobenzo[c][1,2]oxaborol-6-yloxy)-N-(4,4,4-trifluoro-1-hydroxybutan-2-yl)pyrazine-2-carboxamide (33.2 mg) as white solid respectively. Analytical data for the (R)-isomer is shown as following. $^1$H NMR (400 MHz, DMSO-$d_6$): δ 9.10 (s, 1H), 8.74 (d, J=8.8 Hz, 1H), 8.67 (d, J=1.2 Hz, 1H), 8.63 (d, J=1.6 Hz, 1H), 7.30 (d, J=8.4 Hz, 1H), 7.26 (d, J=8.0 Hz, 1H), 5.12 (t, J=6.0 Hz, 1H), 4.99 (s, 2H), 4.36-4.32 (m, 1H), 3.50-3.46 (m, 1H), 3.45-3.39 (m, 1H), 2.74-2.60 (m, 2H), 2.22 (s, 3H) ppm; HPLC purity: 100% at 220 nm and 100% at 254 nm; Chiral purity: 100% at 230 nm; MS: m/z=412.1 (M+1, ESI+).

Example 34

(S)-5-(1-hydroxy-7-methyl-1,3-dihydrobenzo[c][1,2]oxaborol-6-yloxy)-N-(4,4,4-trifluoro-1-hydroxybutan-2-yl)pyrazine-2-carboxamide

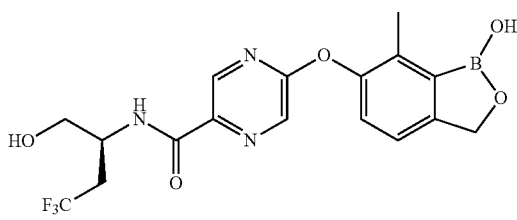 [SMILES: Cc1c(Oc2cnc(C(=O)N[C@H](CO)CC(F)(F)F)cn2)ccc2c1B(O)OC2]

The title (S)-isomer compound was obtained by a chiral HPLC separation from its racemic mixture as described above in the section for another enantiomer. $^1$H NMR (400 MHz, DMSO-$d_6$): δ 9.10 (s, 1H), 8.73 (d, J=9.6 Hz, 1H), 8.67 (d, J=1.6 Hz, 1H), 8.63 (d, J=1.2 Hz, 1H), 7.30 (d, J=8.4 Hz, 1H), 7.26 (d, J=8.0 Hz, 1H), 5.11 (t, J=6.0 Hz, 1H), 4.99 (s, 2H), 4.39-4.30 (m, 1H), 3.49-3.45 (m, 1H), 3.43-3.38 (m, 1H), 2.72-2.59 (m, 2H), 2.22 (s, 3H) ppm; HPLC purity: 100% at 220 nm and 100% at 254 nm; Chiral purity: 98.8% at 230 nm; MS: m/z=412.1 (M+1, ESI+).

Example 35

(S)—N-(1-hydroxy-3-(methylthio)propan-2-yl)-5-((1-hydroxy-7-methyl-1,3-dihydrobenzo[c][1,2]oxaborol-6-yl)oxy)pyrazine-2-carboxamide

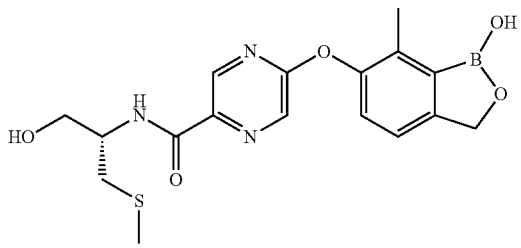 [SMILES: CSC[C@H](CO)NC(=O)c1cnc(Oc2ccc3c(c2C)B(O)OC3)cn1]

Step 1: Preparation of (S)-methyl 2-amino-3-mercaptopropanoate hydrochloride To a solution of (S)-2-amino-3-mercaptopropanoic acid hydrochloride hydrate (3.0 g, 17.0 mmol) in $CH_3OH$ (50 mL) was added $SOCl_2$ (4.1 g, 34.0 mmol) at 0° C. The reaction mixture was stirred at 60° C. overnight. Then concentrated under the reduced pressure to give (S)-methyl 2-amino-3-mercaptopropanoate hydrochloride (2.3 g, crude) as a white solid which was used for next step without further purification. MS: m/z=136.0 (M+1, ESI+).

Step 2: Preparation of (S)-methyl 2-(tert-butoxycarbonylamino)-3-mercaptopropanoate To a solution of (S)-methyl 2-amino-3-mercaptopropanoate hydrochloride (2.0 g, 11.4 mmol) in DCM (50 mL) was added (Boc)$_2$O (3.7 g, 17.1 mmol). The reaction mixture was stirred at rt for 2 h. After cooled to room temperature, EA (150 mL) and ammonia water (50 mL) were added. The organic layer was dried over Na$_2$SO$_4$, filtered and concentrated under the reduced pressure to give (S)-methyl 2-(tert-butoxycarbonylamino)-3-mercaptopropanoate (4 g, crude) as a white solid which was used for next step without further purification. MS: m/z=136.0 (M−99, ESI+).

Step 3: Preparation of (S)-methyl 2-(tert-butoxycarbonylamino)-3-(methylthio)propanoate To a solution of (S)-methyl 2-(tert-butoxycarbonylamino)-3-mercaptopropanoate (4.0 g, 17.0 mmol) in DCM (50 mL) was added MeI (4.8 g, 34.0 mmol) and DIPEA (4.4 g, 34.0 mmol). The reaction mixture was stirred at 25° C. overnight. The solvent was removed and the residue was purified by silica gel column chromatography using PE:EA=2:1 to give (S)-methyl 2-(tert-butoxycarbonylamino)-3-(methylthio)propanoate (2.34 g, yield 54%) as a colorless oil. MS: m/z=150.0 (M−99, ESI+)

Step 4: Preparation of (S)-methyl 2-amino-3-(methylthio)propanoate hydrochloride To a solution of (S)-methyl 2-(tert-butoxycarbonylamino)-3-(methylthio)propanoate (1.2 g, 3.4 mmol) in 1,4-dioxane (30 mL) was added HCl/1,4-dioxane (4N, 30 mL). The reaction mixture was stirred at 25° C. overnight. The mixture was concentrated under the reduced pressure to give crude (S)-methyl 2-amino-3-(methylthio)propanoate hydrochloride (1.4 g) as a white solid which was used for next step without further purification. MS: m/z=150.0 (M+1, ESI+).

Step 5: Preparation of (S)-2-amino-3-(methylthio)propan-1-ol hydrochloride

To a solution of LiAlH$_4$ (0.53 g, 14.0 mmol) in THF (25 mL) was added (S)-methyl 2-amino-3-(methylthio)propanoate hydrochloride (1.4 g, 9.3 mmol) in THF (5 mL) at 0° C. The reaction mixture was stirred at 70° C. for 2 h, and then several drop of H$_2$O was added until no gas generated. It was filtered off and the filtered cake was washed with EA. The combined organic phase was concentrated in vacuum. Then HCl/1,4-dioxane (4N, 20 mL) was added and the resulting mixture was stirred at rt for 30 min. After removed the solvent, H$_2$O (30 mL) was added, washed with EA (3*30 mL) and the water layer was lyophilized to give (S)-2-amino-3-(methylthio)propan-1-ol hydrochloride (880 mg, yield 58%) as a colorless oil. MS: m/z=122.0 (M+1, ESI+).

Step 6: Preparation of (S)-5-chloro-N-(1-hydroxy-3-(methylthio)propan-2-yl)pyrazine-2-carboxamide To a solution of 5-chloropyrazine-2-carboxylic acid (200 mg, 1.26 mmol) and HATU (575 mg, 1.51 mmol) in DMF (5 mL) was added DIPEA (326 mg, 2.52 mmol). The mixture was stirred at rt for 30 min, and then (S)-2-amino-3-(methylthio)propan-1-ol hydrochloride (239 mg, 1.51 mmol) was added. The resulting mixture was stirred at rt for 1 h, water (20 mL) was added and the solution was extracted with EA (30 mL*2). The combined organic layers were washed with brine, dried over Na$_2$SO$_4$, filtered and concentrated under the reduced pressure. The residue was purified by Combiflash (PE:EA=1:1) to give (S)-5-chloro-N-(1-hydroxy-3-(methylthio)propan-2-yl)pyrazine-2-carboxamide (207 mg, 62.6%) as a yellow solid. MS: m/z=262.0 (M+1, ESI+).

Step 7: Preparation of (S)—N-(1-hydroxy-3-(methylthio)propan-2-yl)-5-(1-hydroxy-7-methyl-1,3-dihydrobenzo[c][1,2]oxaborol-6-yloxy)pyrazine-2-carboxamide To a solution of (S)-5-chloro-N-(1-hydroxy-3-(methylthio)propan-2-yl)pyrazine-2-carboxamide (100 mg, 0.383 mmol) and 7-methylbenzo[c][1,2]oxaborole-1,6(3H)-diol (63 mg, 0.383 mmol) in DMF (10 mL) was added Cs$_2$CO$_3$ (249 mg, 0.766 mmol). The reaction mixture was stirred at 60° C. for 2 h, and then filtered off. The filtrate was purified by prep-HPLC to give (S)—N-(1-hydroxy-3-(methylthio)propan-2-yl)-5-(1-hydroxy-7-methyl-1,3-dihydrobenzo[c][1,2]oxaborol-6-yloxy)pyrazine-2-carboxamide (70 mg, yield 47%) as a white solid. $^1$H NMR (400 MHz, DMSO-d$_6$): δ 9.09 (s, 1H), 8.68 (s, 1H), 8.63 (s, 1H), 8.41 (d, J=9.2 Hz, 1H), 7.28 (q, J=8.4 Hz, 2H), 4.99 (s, 2H), 4.95 (t, J=5.2 Hz, 1H), 4.16-4.08 (m, 1H), 3.62-3.47 (m, 2H), 2.79-2.65 (m, 2H), 2.50 (s, 3H), 2.22 (s, 3H) ppm; HPLC purity: 100% at 220 nm and 100% at 254 nm; Chiral HPLC purity: 100% at 230 nm; MS: m/z=390.0 (M+1, ESI+).

Example 36

(S)—N-(1-hydroxy-3-(methylsulfonyl)propan-2-yl)-5-(1-hydroxy-7-methyl-1,3-dihydrobenzo[c][1,2]oxaborol-6-yloxy)pyrazine-2-carboxamide

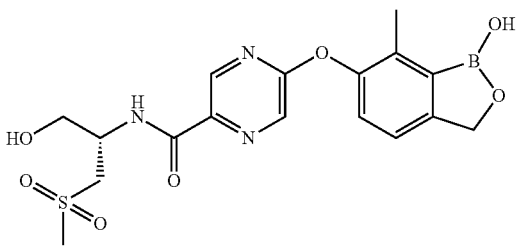 [SMILES: Cc1c(Oc2cnc(C(=O)N[C@@H](CO)CS(C)(=O)=O)cn2)ccc2c1B(O)OC2]

Step 1: Preparation of (S)-5-chloro-N-(1-hydroxy-3-(methylsulfonyl)propan-2-yl)pyrazine-2-carboxamide To a solution of (S)-5-chloro-N-(1-hydroxy-3-(methylthio)propan-2-yl)pyrazine-2-carboxamide (100 mg, 0.383 mmol) in DCM (10 mL) was added mCPBA (132 mg, 0.766 mmol) at 0° C. The mixture was stirred at rt for 90 min, water (20 mL) was added and the solution was extracted with DCM (30 mL*2). The combined organic layers were washed with brine, dried over Na$_2$SO$_4$, filtered and concentrated under reduced pressure. The residue was purified by Combiflash (PE:EA=1:8) to give ((S)-5-chloro-N-(1-hydroxy-3-(methylsulfonyl)propan-2-yl)pyrazine-2-carboxamide (89 mg, yield 79%) as a yellow solid. MS: m/z=294.0 (M+1, ESI+).

Step 2: Preparation of (S)—N-(1-hydroxy-3-(methylsulfonyl)propan-2-yl)-5-(1-hydroxy-7-methyl-1,3-dihydrobenzo[c][1,2]oxaborol-6-yloxy)pyrazine-2-carboxamide To a solution of (S)-5-chloro-N-(1-hydroxy-3-(methylsulfonyl)propan-2-yl)pyrazine-2-carboxamide (84 mg, 0.287 mmol) and 7-methylbenzo[c][1,2]oxaborole-1,6(3H)-diol (47 mg, 0.287 mmol) in DMF (3 mL) was added $Cs_2CO_3$ (186 mg, 0.574 mmol). The reaction mixture was stirred at 60° C. for 2 h and filtered off. The filtrate was purified by prep-HPLC to give (S)—N-(1-hydroxy-3-(methylsulfonyl)propan-2-yl)-5-(1-hydroxy-7-methyl-1,3-dihydrobenzo[c][1,2]oxaborol-6-yloxy)pyrazine-2-carboxamide (54 mg, yield 45%) as a white solid. $^1$H NMR (400 MHz, DMSO-$d_6$): δ 9.10 (s, 1H), 8.78 (d, J=9.2 Hz, 1H), 8.68 (d, J=1.2 Hz, 1H), 8.64 (d, J=1.6 Hz, 1H), 7.30 (d, J=8.0 Hz, 1H), 7.26 (d, J=8.4 Hz, 1H), 5.15 (t, J=5.6 Hz, 1H), 4.99 (s, 2H), 4.53-4.51 (m, 1H), 3.61-3.31 (m, 4H), 2.97 (s, 3H), 2.22 (s, 3H) ppm; Chiral purity: 100% at 230 nm; HPLC purity: 100% at 220 nm and 100% at 254 nm; MS: m/z=422.1 (M+1, ESI+).

Example 37

(R)-5-(1-hydroxy-7-methyl-1,3-dihydrobenzo[c][1,2]oxaborol-6-yloxy)-N-(5,5,5-trifluoro-1-hydroxypentan-2-yl)pyrazine-2-carboxamide

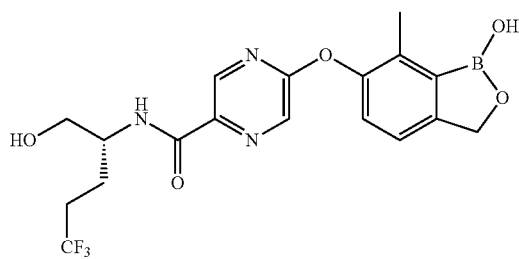 [SMILES: Cc1c(Oc2cnc(C(=O)N[C@@H](CO)CCC(F)(F)F)cn2)ccc2c1B(O)OC2]

Step 1: Preparation of 3, 3, 3-trifluoropropyl trifluoromethanesulfonate

At −25° C., 2,6-lutidine (1.41 g, 13.2 mmol) in DCM (50 mL) was mixed with $Tf_2O$ (3.47 g, 12.3 mmol), and the mixture was stirred for 5 min. To the mixture was added 3,3,3-trifluoropropan-1-ol (1.0 g, 8.8 mmol). After 2 h, it was warmed to rt and stirred for 1 h. The solvent was removed and the residue was purified by silica gel column chromatography using PE:EA=2:1 to give 3,3,3-trifluoropropyl trifluoromethanesulfonate (460 mg, yield 21%) as a yellow oil. $^1$H NMR (400 MHz, CDCl$_3$): δ 4.73-4.70 (m, 2H), 2.72-2.65 (m, 2H) ppm.

Step 2: Preparation of tert-butyl 2-(diphenylmethyleneamino)-5,5,5-trifluoropentanoate A solution of tert-butyl 2-(diphenylmethyleneamino)acetate (424 mg, 1.44 mmol) in THF (20 mL) was cooled to −78° C. and treated dropwise with LDA (2M in THF, 1.08 mL, 2.16 mmol), and then added 3,3,3-trifluoropropyl trifluoromethanesulfonate (460 mg, 1.87 mmol) in THF (2 mL) dropwise. The reaction mixture was gradually warmed to rt and stirred for 4 h. The reaction was quenched with 50 mL saturated NH$_4$Cl at 0° C. and then extracted with ethyl acetate (100 mL×2). The organic layers were dried over Na$_2$SO$_4$ and concentrated under reduced pressure. The residue was purified by silica gel column chromatography using PE:EA=40:1 to give tert-butyl 2-(diphenylmethyleneamino)-5,5,5-trifluoropentanoate (400 mg, yield 71%) as a colorless oil. $^1$H NMR (400 MHz, CDCl$_3$): δ 7.66-7.16 (m, 10H), 3.98 (t, 1H), 2.18-2.07 (m, 4H), 1.43 (s, 9H) ppm.

Step 3: Preparation of 2-amino-5,5,5-trifluoropentanoic acid hydrochloride

A solution of tert-butyl 2-(diphenylmethyleneamino)-5,5,5-trifluoropentanoate (400 mg, 1.02 mmol) in 50% HCl (5 mL) was refluxed overnight. Water was removed to give 2-amino-5,5,5-trifluoropentanoic acid hydrochloride (210 mg, yield 99%) as a white solid. MS: m/z=172.3 (M+1, ESI+).

Step 4: Preparation of 2-amino-5, 5, 5-trifluoropentan-1-ol hydrochloride

To a solution of 2-amino-5,5,5-trifluoropentanoic acid hydrochloride (210 mg, 1.0 mmol) in THF (10 mL) was added LAH (76 mg, 2.0 mmol). The mixture was stirred at 70° C. overnight. Several drop of water was added and filtered. The filtrate was concentrated under reduced pressure. 2 mL of 4M HCl/1,4-dioxane was added at rt and stirred for 30 min. Water (10 mL) was added and then the mixture was extracted with EtOAc (10 mL×2). The aqueous layer was freeze-dried to give 2-amino-5,5,5-trifluoropentan-1-ol hydrochloride (150 mg, yield 77%) as a white solid. MS: m/z=158.3 (M+1, ESI+).

Step 5: Preparation of 5-chloro-N-(5, 5, 5-trifluoro-1-hydroxypentan-2-yl)pyrazine-2-carboxamide A solution of 5-chloropyrazine-2-carboxylic acid (123 mg, 0.78 mmol), HATU (593 mg, 1.56 mmol) and DIPEA (302 mg, 2.34 mmol) in DMF (5 mL) was stirred at rt for 30 min. Then 2-amino-5,5,5-trifluoropentan-1-ol hydrochloride (150 mg, 0.78 mmol) was added and the reaction mixture was continued to be stirred at rt overnight. The crude obtained from a normal work-up was purified by prep-HPLC to give 5-chloro-N-(5,5,5-trifluoro-1-hydroxypentan-2-yl)pyrazine-2-carboxamide (60 mg, yield 26%) as a white solid. MS: m/z=298.1 (M+1, ESI+).

Step 6: Preparation of 5-(1-hydroxy-7-methyl-1,3-dihydrobenzo[c][1,2]oxaborol-6-yloxy)-N-(5, 5, 5-trifluoro-1-hydroxypentan-2-yl)pyrazine-2-carboxamide A solution of 5-chloro-N-(5,5,5-trifluoro-1-hydroxypentan-2-yl)pyrazine-2-carboxamide (60 mg, 0.2 mmol), 7-methylbenzo[c][1,2]oxaborole-1,6(3H)-diol (33 mg, 0.2 mmol) and Cs$_2$CO$_3$ (131 mg, 0.4 mmol) in DMF (4 mL) was stirred at 50° C. for 4 h. After cooled to room temperature, the crude was purified by Prep-HPLC to give 5-(1-hydroxy-7-methyl-1,3-dihydrobenzo[c][1,2]oxaborol-6-yloxy)-N-(5,5,5-trifluoro-1-hydroxypentan-2-yl)pyrazine-2-carboxamide (32 mg, yield 27%) as a white solid. MS: m/z=426.1 (M+1, ESI+).

Step 7: Preparation of (R)-5-(1-hydroxy-7-methyl-1,3-dihydrobenzo[c][1,2]oxaborol-6-yloxy)-N-(5, 5, 5-trifluoro-1-hydroxypentan-2-yl)pyrazine-2-carboxamide and (S)-5-(1-hydroxy-7-methyl-1,3-dihydrobenzo[c][1,2]oxaborol-6-yloxy)-N-(5, 5, 5-trifluoro-1-hydroxypentan-2-yl)pyrazine-2-carboxamide The racemic mixture 5-(1-hydroxy-7-methyl-1,3-dihydrobenzo[c][1,2]oxaborol-6-yloxy)-N-(5, 5,5-trifluoro-1-hydroxypentan-2-yl)pyrazine-2-carboxamide (40 mg) was separated by chiral HPLC method using the following condition: instrument SFC-80 (Thar, Waters), column CHIRALPAK AD 20*250 mm, 5 um, column temperature 35° C., mobile phase $CO_2$/Methanol=70/30, flow rate 80 g/min, back pressure 100 bar, detection wavelength 214 nm or 230 nm, cycle time 6.0 min, sample solution 300 mg in 60 mL MeOH, and injection volume 4.5 mL (loading 23 mg/injection). (R)-5-(1-hydroxy-7-methyl-1,3-dihydrobenzo[c][1,2]oxaborol-6-yloxy)-N-(5, 5,5-trifluoro-1-hydroxypentan-2-yl)pyrazine-2-carboxamide (11.9 mg, yield 30%) was obtained as a white solid. $^1$H NMR (400 MHz, DMSO-$d_6$): δ 9.09 (s, 1H), 8.67 (s, 1H), 8.62 (s, 1H), 8.49 (d, J=9.2 Hz, 2H), 7.30 (d, J=8.2 Hz, 1H), 7.26 (d, J=8.2 Hz, 1H), 4.99 (s, 2H), 4.93 (t, J=6.0 Hz, 1H), 4.05-4.01 (m, 1H), 3.51-3.45 (m, 2H), 2.30-2.22 (m, 5H), 1.88-1.74 (m, 2H) ppm; HPLC purity: 100% at 214 nm and 100% at 254 nm; MS: m/z=426.2 (M+1, ESI+); Chiral purity: 100% at 230 nm.

Example 38

(S)-5-(1-hydroxy-7-methyl-1,3-dihydrobenzo[c][1,2]oxaborol-6-yloxy)-N-(5,5,5-trifluoro-1-hydroxypentan-2-yl)pyrazine-2-carboxamide

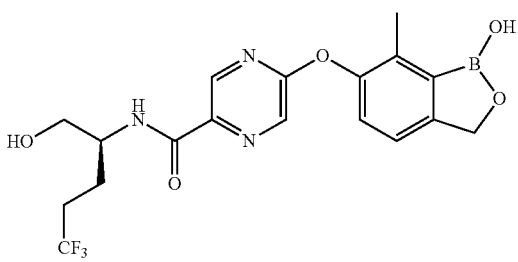 [SMILES: Cc1c(Oc2cnc(C(=O)N[C@H](CO)CCC(F)(F)F)cn2)ccc2c1B(O)OC2]

The title (S)-isomer compound was obtained by a chiral HPLC separation from its racemic mixture as described above in the section for another enantiomer. (S)-5-(1-hydroxy-7-methyl-1,3-dihydrobenzo[c][1,2]oxaborol-6-yloxy)-N-(5,5,5-trifluoro-1-hydroxypentan-2-yl)pyrazine-2-carboxamide (11.2 mg, yield 28%) was obtained as a white solid. $^1$H NMR (400 MHz, DMSO-$d_6$): δ 9.10 (s, 1H), 8.67 (s, 1H), 8.62 (s, 1H), 8.49 (d, J=9.2 Hz, 2H), 7.30 (d, J=8.2 Hz, 1H), 7.26 (d, J=8.4 Hz, 1H), 4.99 (s, 2H), 4.94 (t, J=6.0 Hz, 1H), 4.05-4.01 (m, 1H), 3.51-3.45 (m, 2H), 2.30-2.22 (m, 5H), 1.88-1.74 (m, 2H) ppm; HPLC purity: 100% at 214 nm and 100% at 254 nm; MS: m/z=426.2 (M+1, ESI+); Chiral purity: 98.1% at 239 nm.

Example 39

5-(1-hydroxy-7-methyl-1,3-dihydrobenzo[c][1,2]oxaborol-6-yloxy)-N-(3-hydroxybutan-2-yl)pyrazine-2-carboxamide

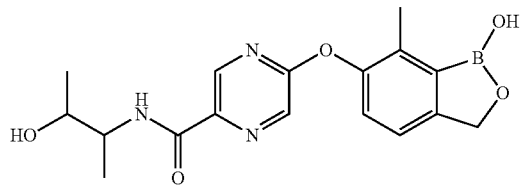

Step 1: Preparation of 3-aminobutan-2-ol

The solution of 3-nitrobutan-2-ol (1.0 g, 8.4 mmol) in MeOH (30 mL) was hydrogenated using 10% Pd/C (100 mg) as catalyst under $H_2$ overnight. The catalyst was removed by filtration on Celite and the solvent was evaporated under reduced pressure to give 3-aminobutan-2-ol (740 mg, yield 99%) as colorless oil. It was used in next step without further purification.

Step 2: Preparation of 5-(1-hydroxy-7-methyl-1,3-dihydrobenzo[c][1,2]oxaborol-6-yloxy)-N-(3-hydroxybutan-2-yl)pyrazine-2-carboxamide To a solution of 5-(1-hydroxy-7-methyl-1,3-dihydrobenzo[c][1,2]oxaborol-6-yloxy)pyrazine-2-carboxylic acid (100 mg, 0.35 mmol) and DIPEA (135 mg, 1.05 mmol) in DMF (3 mL) was added HATU (200 mg, 0.53 mmol). The reaction mixture was stirred at rt for 30 min, and then 3-aminobutan-2-ol (250 mg, 0.35 mmol) was added. The reaction mixture was stirred at rt overnight. The crude product obtained from a normal work-up was purified by prep-HPLC to give 5-(1-hydroxy-7-methyl-1,3-dihydrobenzo[c][1,2]oxaborol-6-yloxy)pyrazine-2-carboxylic acid (50 mg, yield 41%) as a white solid. $^1$H NMR (400 MHz, DMSO-$d_6$): δ9.11 (s, 1H), 8.67 (s, 1H), 8.61 (s, 1H), 8.33-8.09 (m, 1H), 7.30 (d, J=8.0 Hz, 1H), 7.26 (d, J=8.0 Hz, 1H), 4.99 (s, 2H), 3.89-3.64 (m, 2H), 2.22 (s, 3H), 1.16-1.11 (m, 3H), 1.07-1.03 (m, 3H) ppm; HPLC purity: 99.0% at 220 nm and 100% at 254 nm; MS: m/z=358 (M+1, ESI+).

Example 40

(3-hydroxy-3-methylpyrrolidin-1-yl) (5-((1-hydroxy-7-methyl-1,3-dihydrobenzo[c][1,2]oxaborol-6-yl)oxy)pyrazin-2-yl)methanone

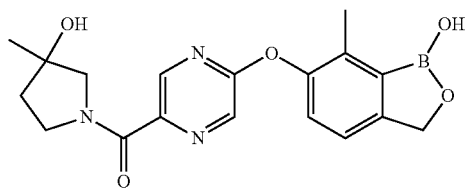 [SMILES: Cc1c(Oc2cnc(C(=O)N3CCC(C)(O)C3)cn2)ccc2c1B(O)OC2]

Preparation of (3-hydroxy-3-methylpyrrolidin-1-yl) (5-(1-hydroxy-7-methyl-1,3-dihydrobenzo[c][1,2] oxaborol-6-yloxy)pyrazin-2-yl)methanone A solution of 5-(1-hydroxy-7-methyl-1,3-dihydrobenzo[c][1,2]oxaborol-6-yloxy)pyrazine-2-carboxylic acid (80 mg, 0.28 mmol), HATU (213 mg, 0.56 mmol) and DIPEA (144 mg, 1.12 mmol) in DMF (3 mL) was stirred at rt for 30 min, and then 3-methylpyrrolidin-3-ol hydrochloride (58 mg, 0.42 mmol) was added. The reaction mixture was continued to be stirred at rt overnight. The crude product obtained from a normal work-up was purified by prep-HPLC to give (3-hydroxy-3-methylpyrrolidin-1-yl)(5-(1-hydroxy-7-methyl-1,3-dihydrobenzo[c][1,2]oxaborol-6-yloxy) pyrazin-2-yl)methanone (12 mg, yield 12%) as a white solid. The ratio of the two stereo-isomers in this racemic product is about 60:40 according by $^1$HNMR. $^1$H NMR (400 MHz, DMSO-$d_6$): δ 9.08 (s, 1H), 8.57-8.56 (m, 1H), 8.50-8.48 (m, 1H), 7.30 (d, J=8.4 Hz, 1H), 7.26 (d, J=8.4 Hz, 1H), 4.99 (s, 2H), 4.85-4.79 (m, 1H), 3.62-3.49 (m, 4H), 2.23 (s, 3H), 1.85-1.81 (m, 2H), 1.33-1.27 (m, 3H) ppm; HPLC purity: 100% at 220 nm and 100% at 254 nm; MS: m/z=370.1 (M+1, ESI+).

Example 41

(3-hydroxy-3-methylazetidin-1-yl) (5-((1-hydroxy-7-methyl-1,3-dihydrobenzo[c][1,2]oxaborol-6-yl) oxy)pyrazin-2-yl)methanone

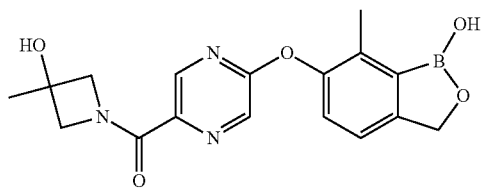 [SMILES: Cc1c(Oc2cnc(C(=O)N3CC(C)(O)C3)cn2)ccc2c1B(O)OC2]

Step 1: Preparation of 1-benzhydryl-3-methylazetidin-3-ol

To a solution of 1-benzhydrylazetidin-3-one (7.11 g, 30 mmol) in dry THF (150 mL) was added methylmagnesium bromide (3M, 30 mL, 90 mmol) dropwise at −78° C. After stirred at −78° C. for 2 h, the reaction mixture was gradually warmed to rt and stirred overnight. Saturated NH$_4$Cl (100 mL) was added and extracted with EA (100 mL×3). The combined organic layers were washed with brine, dried over Na$_2$SO$_4$, filtered and concentrated under the reduced pressure. The residue was purified by silica gel column chromatography using PE:EA (4:1) as elution to give 1-benzhydryl-3-methylazetidin-3-ol (7.0 g, yield 92%) as a yellow solid. MS: m/z=254.1 (M+1, ESI+).

Step 2: Preparation of 3-methylazetidin-3-ol hydrochloride

To a solution of 1-benzhydryl-3-ethylazetidin-3-ol (7.0 g, 27.7 mmol) and HCl (1N, 28 mL) in MeOH (100 mL) was hydrogenated using 10% Pd/C (800 mg) as catalyst under atmospheric pressure of H$_2$ overnight. The catalyst was removed and the solvent was evaporated to give 3-methylazetidin-3-ol hydrochloride (3.0 g, yield 88%) as a light yellow solid. It was used in next step without further purification.

Step 3: Preparation of (3-hydroxy-3-methylazetidin-1-yl) (5-(1-hydroxy-7-methyl-1,3-dihydrobenzo[c][1,2]oxaborol-6-yloxy)pyrazin-2-yl)methanone A solution of 5-(1-hydroxy-7-methyl-1,3-dihydrobenzo[c][1,2]oxaborol-6-yloxy)pyrazine-2-carboxylic acid (1.08 g, 3.78 mmol), HATU (2.87 g, 7.56 mmol) and DIPEA (1.95 g, 15.12 mmol) in DMF (15 mL) was stirred at rt for 30 min. 3-Methylazetidin-3-ol hydrochloride (558 mg, 4.54 mmol) was added and the reaction mixture was stirred at rt overnight. The crude sample obtained from a normal work-up was purified by prep-HPLC to give (3-hydroxy-3-methylazetidin-1-yl)(5-(1-hydroxy-7-methyl-1,3-dihydrobenzo[c][1,2]oxaborol-6-yloxy)pyrazin-2-yl)methanone (630 mg, yield 47%) as a white solid. $^1$H NMR (400 MHz, DMSO-$d_6$): δ 9.10 (s, 1H), 8.62 (d, J=1.2 Hz, 1H), 8.57 (d, J=1.2 Hz, 1H), 7.29 (d, J=8.4 Hz, 1H), 7.25 (d, J=8.4 Hz, 1H), 5.71 (s, 1H), 4.99 (s, 2H), 4.41 (d, J=9.6 Hz, 1H), 4.35 (d, J=9.6 Hz, 1H), 3.95 (d, J=9.6 Hz, 1H), 3.90 (d, J=9.6 Hz, 1H), 2.21 (s, 3H), 1.40 (s, 3H) ppm; HPLC purity: 100% at 214 nm and 100% at 254 nm; MS: m/z=356.1 (M+1, ESI+).

Example 42

5-((1-hydroxy-7-methyl-1,3-dihydrobenzo[c][1,2]oxaborol-6-yl) oxy)-N-((1R,2R)-2-hydroxycyclopentyl)pyrazine-2-carboxamide

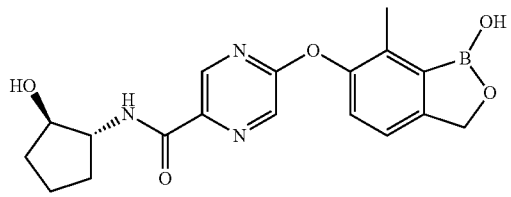 [SMILES: Cc1c(Oc2cnc(C(=O)N[C@@H]3CCC[C@H]3O)cn2)ccc2c1B(O)OC2]

Preparation of 5-(1-hydroxy-7-methyl-1,3-dihydrobenzo[c][1,2]oxaborol-6-yloxy)-N-((1R,2R)-2-hydroxycyclopentyl)pyrazine-2-carboxamide A solution of 5-(1-hydroxy-7-methyl-1,3-dihydrobenzo[c][1,2]oxaborol-6-yloxy)pyrazine-2-carboxylic acid (50 mg, 0.17 mmol), HATU (100 mg, 0.26 mmol) and DIPEA (88 mg, 0.68 mmol) in DMF (3 mL) was stirred at rt for 30 min. (1R,2R)-2-aminocyclopentanol (26 mg, 0.26 mmol) was added and the reaction mixture was stirred at rt overnight. The crude product obtained from a normal work-up was purified by prep-HPLC to give 5-((1-hydroxy-7-methyl-1,3-dihydrobenzo[c][1,2]oxaborol-6-yl)oxy)-N-((1R,2R)-2-hydroxycyclopentyl)pyrazine-2-carboxamide (20.1 mg, yield 31%) as a white solid. $^1$H NMR (400 MHz, DMSO-$d_6$): δ 9.09 (s, 1H), 8.65 (d, J=1.2 Hz, 1H), 8.61 (d, J=1.2 Hz, 1H), 8.48 (d, J=7.2 Hz, 1H), 7.30 (d, J=8 Hz, 1H), 7.26 (d, J=8 Hz, 1H), 4.99 (s, 2H), 4.03-4.00 (m, 2H), 2.21 (s, 3H), 1.99-1.95 (m, 1H), 1.86-1.83 (m, 1H), 1.67-1.61 (m, 2H), 1.54-1.45 (m, 2H) ppm; HPLC purity: 100% at 214 nm and 100% at 254 nm; MS: m/z=370.0 (M+1, ESI+).

Example 43

(R)—N-(2-hydroxy-2-methylhexan-3-yl)-5-((1-hydroxy-7-methyl-1,3-dihydrobenzo[c][1,2]oxaborol-6-yl)oxy)pyrazine-2-carboxamide

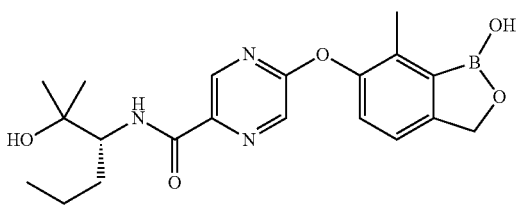 [SMILES: CCC[C@@H](NC(=O)c1cnc(Oc2ccc3c(c2C)B(O)OC3)cn1)C(C)(C)O]

Step 1: Preparation of (R)-methyl 2-aminopentanoate hydrochloride

To a solution of (R)-2-aminopentanoic acid (2.0 g, 17.1 mmol) in MeOH (50 mL) was added $SOCl_2$ (4.0 g, 34.2 mmol) dropwise at 0° C. The reaction mixture was stirred at 70° C. for 2 h, and then concentrated under the reduced pressure to give (R)-methyl 2-aminopentanoate hydrochloride (2.0 g, yield 70%) as a white solid. MS: m/z=132.1 (M+1, ESI+).

Step 2: Preparation of (R)-3-amino-2-methylhexan-2-ol

To a solution of (R)-methyl 2-aminopentanoate hydrochloride (2.0 g, 12.0 mmol) in dry THF (100 mL) was added methylmagnesium bromide (16 mL, 48 mmol, 3M in ether) at 0° C. The reaction mixture was stirred at room temperature overnight. The mixture was quenched with saturated $NH_4Cl$ and extracted with EtOAc (20 mL×3). The combined organic layer was washed with brine, dried over $Na_2SO_4$, filtered and concentrated under reduced pressure. The residue was purified by column chromatography on silical gel eluted with DCM: MeOH: TEA (10:1:0.01) to give (R)-3-amino-2-methylhexan-2-ol (800 mg, yield 51%). MS: m/z=132.1 (M+1, ESI+).

Step 3: Preparation of (R)—N-(2-hydroxy-2-methylhexan-3-yl)-5-(1-hydroxy-7-methyl-1, 3-dihydrobenzo[c][1,2]oxaborol-6-yloxy)pyrazine-2-carboxamide A solution of 5-(1-hydroxy-7-methyl-1,3-dihydrobenzo[c][1,2]oxaborol-6-yloxy)pyrazine-2-carboxylic acid (200 mg, 0.7 mmol), HATU (400 mg, 1.05 mmol) and DIPEA (361 mg, 2.8 mmol) in DMF (5 mL) was stirred at rt for 30 min. And then (R)-3-amino-2-methylhexan-2-ol (100 mg, 0.84 mmol) was added and the reaction mixture was stirred at rt overnight. The crude residue obtained from a normal work-up was purified by prep-HPLC to give (R)—N-(2-hydroxy-2-methylhexan-3-yl)-5-(1-hydroxy-7-methyl-3-dihydrobenzo[c][1,2]oxaborol-6-yloxy)pyrazine-2-carboxamide (29 mg, yield 10%) as a white solid. $^1$HNMR (400 MHz, DMSO-d6): δ 9.07 (s, 1H), 8.66 (d, J=0.8 Hz, 1H), 8.61 (d, J=0.8 Hz, 1H), 7.97 (d, J=10.0 Hz, 1H), 7.28 (d, J=8.2 Hz, 1H), 7.25 (d, J=8.2 Hz, 1H), 4.98 (s, 2H), 4.58 (s, 1H), 3.87-3.81 (m, 1H), 2.22 (s, 3H), 1.70-1.62 (m, 1H), 1.52-1.42 (m, 1H), 1.34-1.16 (m, 2H), 1.14 (s, 3H), 1.05 (s, 3H), 0.85 (t, J=7.6 Hz, 3H) ppm; HPLC purity: 100% at 214 nm and 100% at 254 nm; MS: m/z=400.0 (M+1, ESI+); Chiral purity: 100% at 230 nm.

Example 44

(S)—N-(2-hydroxy-2-methylhexan-3-yl)-5-(1-hydroxy-7-methyl-1,3-dihydrobenzo[c][1,2]oxaborol-6-yloxy)pyrazine-2-carboxamide

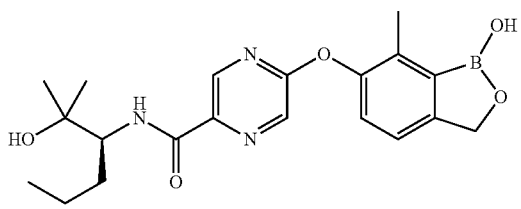 [SMILES: CCC[C@H](NC(=O)c1cnc(Oc2ccc3c(c2C)B(O)OC3)cn1)C(C)(C)O]

Step 1: Preparation of (S)-methyl 2-aminopentanoate

To a solution of (S)-2-aminopentanoic acid (2.0 g, 17.1 mmol) in MeOH (50 mL) was added $SOCl_2$ (4.0 g, 34.2 mmol) dropwise at 0° C. The reaction mixture was stirred at 70° C. for 2 h, and then concentrated under the reduced pressure to give (S)-methyl 2-aminopentanoate hydrochloride (2.0 g, yield 70%) as a white solid. MS: m/z=132.1 (M+1, ESI+).

Step 2: Preparation of (S)-3-amino-2-methylhexan-2-ol

To a solution of (S)-methyl 2-aminopentanoate hydrochloride (2.0 g, 12.0 mmol) in dry THF (100 mL) was added methylmagnesium bromide (16 mL, 48 mmol, 3M in ether) at 0° C. The reaction mixture was stirred at room temperature overnight. The mixture was quenched with saturated $NH_4Cl$ and extracted with EtOAc (20 mL×3). The combined organic layer was washed with brine, dried over $Na_2SO_4$, filtered and concentrated under reduced pressure. The residue was purified by column chromatography on silical gel eluted with DCM: MeOH: TEA (10:1:0.01) to give (S)-3-amino-2-methylhexan-2-ol (800 mg, yield 51%). MS: m/z=132.1 (M+1, ESI+).

Step 3: Preparation of (S)—N-(2-hydroxy-2-methylhexan-3-yl)-5-(1-hydroxy-7-methyl-1, 3-dihydrobenzo[c][1,2]oxaborol-6-yloxy)pyrazine-2-carboxamide To a solution of 5-(1-hydroxy-7-methyl-1,3-dihydrobenzo[c][1,2]oxaborol-6-yloxy)pyrazine-2-carboxylic acid (200 mg, 0.70 mmol) in DMF (5.0 mL) was added HATU (400 mg, 1.04 mmol) and DIPEA (360 mg, 2.78 mmol). After the reaction mixture was stirred at room temperature for 15 min, (S)-3-amino-2-methylhexan-2-ol (100 mg, 0.84 mmol) was added. Then, the mixture was stirred at room temperature overnight. The mixture was quenched with water and extracted with EtOAc (20 mL×3). The combined organic layer was washed with brine, dried over $Na_2SO_4$, filtered and concentrated under reduced pressure. The crude residue was purified by prep-HPLC to give (S)—N-(2-hydroxy-2-methylhexan-3-yl)-5-(1-hydroxy-7- methyl-1,3-dihydrobenzo[c][1,2]oxaborol-6-yloxy)pyrazine-2-carboxamide (29.0 mg, Yield 10%). ¹HNMR (400 MHz, DMSO-d6): δ 9.06 (s, 1H), 8.66 (s, 1H), 8.60 (s, 1H), 7.98 (d, J=10.0 Hz, 1H), 7.28 (d, J=8.4 Hz, 1H), 7.24 (d, J=8.4 Hz, 1H), 4.97 (s, 2H), 4.59 (s, 1H), 3.85-3.81 (m, 1H), 2.21 (s, 3H), 1.69-1.61 (m, 1H), 1.50-1.45 (m, 1H), 1.34-1.16 (m, 2H), 1.14 (s, 3H), 1.04 (s, 3H), 0.84 (t, J=8.0 Hz, 3H) ppm. HPLC purity: 100% at 214 nm and 100% at 254 nm; MS: m/z=400.1 (M+1, ESI+). Chiral HPLC purity: 100% at 230 nm.

Example 45

(R)—N-(2-hydroxy-2-methylpentan-3-yl)-5-(1-hydroxy-7-methyl-1,3-dihydrobenzo[c][1,2]oxaborol-6-yloxy)pyrazine-2-carboxamide

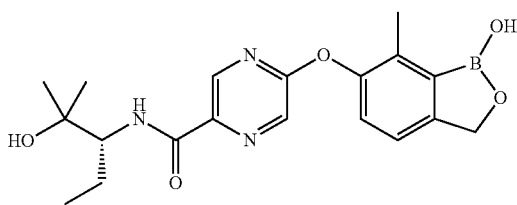 [SMILES: CC[C@@H](NC(=O)c1cnc(Oc2ccc3c(c2C)B(O)OC3)cn1)C(C)(C)O]

Step 1: Preparation of (R)-methyl 2-aminobutanoate hydrochloride

To a solution of (R)-2-aminobutanoic acid (2.0 g, 19.4 mmol) in MeOH (50 mL) was added SOCl₂ (4.6 g, 38.8 mmol) dropwise at 0° C. The reaction mixture was stirred at 70° C. for 2 h, and then concentrated under the reduced pressure to give (R)-methyl 2-aminobutanoate hydrochloride (2.0 g, yield 67%) as a white solid. ¹H NMR (400 Hz, DMSO-d6): δ 8.82 (s, 3H), 4.12 (s, 1H), 3.83 (s, 3H), 2.15-2.08 (m, 2H), 1.12 (t, J=8.0 Hz, 3H) ppm; MS: m/z=118.1 (M+1, ESI+).

Step 2: Preparation of (R)-3-amino-2-methylpentan-2-ol

To a solution of (R)-methyl 2-aminobutanoate hydrochloride (2.0 g, 13.1 mmol) in dry THF (100 mL) was added methylmagnesium bromide (17.5 mL, 52.4 mmol, 3M in ether) at 0° C. The reaction mixture was stirred at room temperature overnight. The mixture was quenched with saturated NH₄Cl and extracted with EtOAc (20 mL×3). The combined organic layers were washed with brine, dried over Na₂SO₄, filtered and concentrated under reduced pressure. The residue was purified by column chromatography on silical gel eluted with DCM: MeOH: TEA (10:1:0.01) to give (R)-3-amino-2-methylpentan-2-ol (800 mg, yield 52%). MS: m/z=118.1 (M+1, ESI+).

Step 3: Preparation of (R)—N-(2-hydroxy-2-methylpentan-3-yl)-5-(1-hydroxy-7-methyl-1,3-dihydrobenzo[c][1,2]oxaborol-6-yloxy)pyrazine-2-carboxamide A solution of 5-(1-hydroxy-7-methyl-1,3-dihydrobenzo[c][1,2]oxaborol-6-yloxy)pyrazine-2-carboxylic acid (1.0 g, 3.5 mmol), HATU (2.0 g, 5.25 mmol) and DIPEA (1.8 g, 13.95 mmol) in DMF (10 mL) was stirred at rt for 30 min. Then (R)-3-amino-2-methylpentan-2-ol (500 mg, 4.2 mmol) was added and the reaction mixture was stirred at rt overnight. The crude product obtained from a normal work-up was purified by prep-HPLC to give (R)—N-(2-hydroxy-2-methylpentan-3-yl)-5-(1-hydroxy-7-methyl-1,3-dihydrobenzo[c][1,2]oxaborol-6-yloxy)pyrazine-2-carboxamide (248 mg, yield 18%) as a white solid. ¹HNMR (400 MHz, DMSO-d₆): δ 9.08 (s, 1H), 8.68 (s, 1H), 8.62 (s, 1H), 7.97 (d, J=8.0 Hz, 1H), 7.30 (d, J=8.4 Hz, 1H), 7.26 (d, J=8.4 Hz, 1H), 4.99 (s, 2H), 4.59 (s, 1H), 3.78-3.73 (m, 1H), 2.23 (s, 3H), 1.79-1.77 (m, 1H), 1.47-1.45 (m, 1H), 1.15 (s, 3H), 1.06 (s, 3H), 0.81 (t, J=6.0 Hz, 3H) ppm; HPLC purity: 100% at 214 nm and 100% at 254 nm; MS: m/z=386.3 (M+1, ESI+); Chiral HPLC purity: 100% at 230 nm.

Example 46

5-(1-hydroxy-7-methyl-1,3-dihydrobenzo[c][1,2]oxaborol-6-yloxy)-N-((1S,2S)-2-hydroxycyclopentyl)pyrazine-2-carboxamide

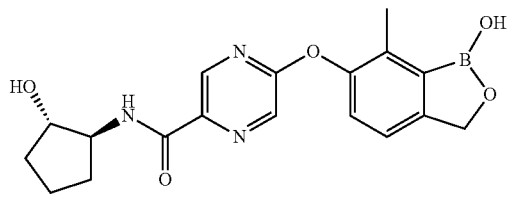 [SMILES: Cc1c(Oc2cnc(C(=O)N[C@H]3CCC[C@@H]3O)cn2)ccc2c1B(O)OC2]

Preparation of 5-(1-hydroxy-7-methyl-1,3-dihydrobenzo[c][1,2]oxaborol-6-yloxy)-N-((1S,2S)-2-hydroxycyclopentyl)pyrazine-2-carboxamide A solution of 5-(1-hydroxy-7-methyl-1,3-dihydrobenzo[c][1,2]oxaborol-6-yloxy)pyrazine-2-carboxylic acid (50 mg, 0.17 mmol), HATU (100 mg, 0.26 mmol) and DIPEA (88 mg, 0.68 mmol) in DMF (3 mL) was stirred at rt for 30 min. Then (1R,2R)-2-aminocyclopentanol (26 mg, 0.26 mmol) was added and the reaction mixture was stirred at rt overnight. The crude product obtained from a normal work-up was purified by prep-HPLC to give 5-((1-hydroxy-7-methyl-1,3-dihydrobenzo[c][1,2]oxaborol-6-yl)oxy)-N-((1 S,2S)-2-hydroxycyclopentyl)pyrazine-2-carboxamide (9.7 mg, yield 15%) as a white solid. ¹H NMR (400 MHz, DMSO-d₆): δ 9.09 (s, 1H), 8.65 (d, J=0.8 Hz, 1H), 8.60 (d, J=0.8 Hz, 1H), 8.48 (d, J=7.6 Hz, 1H), 7.30 (d, J=8.0 Hz, 1H), 7.26 (d, J=8.0 Hz, 1H), 4.99 (s, 2H), 4.79 (d, J=4.4 Hz, 1H), 4.04-4.00 (m, 2H), 2.21 (s, 3H), 1.99-1.95 (m, 1H), 1.86-1.83 (m, 1H), 1.67-1.62 (m, 2H), 1.54-1.46 (m, 2H) ppm; HPLC purity: 100% at 220 nm and 100% at 254 nm; MS: m/z=370.0 (M+1, ESI+); Chiral HPLC purity: 100% at 230 nm.

Example 47

(S)—N-(3-hydroxy-3-methylbutan-2-yl)-5-(1-hydroxy-7-methyl-1,3-dihydrobenzo[c][1,2]oxaborol-6-yloxy)pyrazine-2-carboxamide

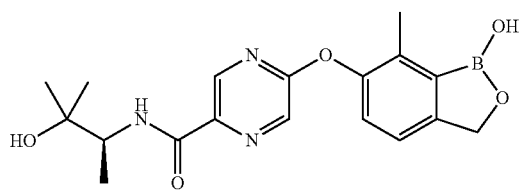 [SMILES: Cc1c(Oc2cnc(C(=O)N[C@@H](C)C(C)(C)O)cn2)ccc2c1B(O)OC2]

Step 1: Preparation of (S)-methyl 2-aminopropanoate hydrochloride

To a solution of (S)-2-aminopropanoic acid (1.0 g, 11.23 mmol) in MeOH (30 mL) at 0° C. was added dropwise $SOCl_2$ (2.67 g, 22.47 mmol). The reaction mixture was refluxed for 2 h, and then solvent was removed to give crude (S)-methyl 2-aminopropanoate hydrochloride (1.6 g) as a white solid. It was used in next step without further purification.

Step 2: Preparation of (S)-3-amino-2-methylbutan-2-ol

To a solution of crude (S)-methyl 2-aminopropanoate hydrochloride (1.6 g, 11.51 mmol) in THF (30 mL) at 0° C. was added MeMgBr (3M, 15 mL, 46.04 mmol) dropwise. The reaction mixture was stirred at rt overnight. The mixture was quenched with saturated $NH_4Cl$ and extracted with EtOAc (20 mL×3). The combined organic layers were washed with brine, dried over $Na_2SO_4$, filtered and concentrated under reduced pressure. The residue was purified by column chromatography on silical gel eluted with MeOH: DCM: $Et_3N$ (10:80:3) to give crude (S)-3-amino-2-methylbutan-2-ol (100 mg) as a colorless oil. It was used in next step without further purification. MS: m/z=104.1 (M+1, ESI+).

Step 3: Preparation of (S)—N-(3-hydroxy-3-methylbutan-2-yl)-5-(1-hydroxy-7-methyl-1, 3-dihydrobenzo[c][1,2]oxaborol-6-yloxy)pyrazine-2-carboxamide A solution of 5-(1-hydroxy-7-methyl-1,3-dihydrobenzo[c][1,2]oxaborol-6-yloxy)pyrazine-2-carboxylic acid (60 mg, 0.21 mmol), HATU (120 mg, 0.31 mmol) and DIPEA (81 mg, 0.63 mmol) in DMF (3 mL) was stirred at rt for 30 min. Then (S)-3-amino-2-methylbutan-2-ol (26 mg, 0.25 mmol) was added and the reaction mixture was stirred at rt overnight. The crude product was purified by prep-HPLC to give (S)—N-(3-hydroxy-3-methylbutan-2-yl)-5-((1-hydroxy-7-methyl-1,3-dihydrobenzo[c][1,2]oxaborol-6-yl)oxy)pyrazine-2-carboxamide (8.6 mg, yield 11%) as a white solid. $^1H$ NMR (400 MHz, DMSO-$d_6$): δ 9.08 (s, 1H), 8.67 (s, 1H), 8.62 (s, 1H), 8.11 (d, J=9.2 Hz, 1H), 7.30 (d, J=8.0 Hz, 1H), 7.26 (d, J=8.0 Hz, 1H), 4.99 (s, 2H), 4.72 (s, 1H), 3.92-3.87 (m, 1H), 2.22 (s, 3H), 1.15 (s, 3H), 1.12 (d, J=6.4 Hz, 3H), 1.09 (s, 3H) ppm; HPLC purity: 100% at 214 nm and 100% at 254 nm; MS: m/z=372.1 (M+1, ESI+); Chiral purity: 100% at 230 nm.

Example 48

(R)—N-(3-hydroxy-3-methylbutan-2-yl)-5-(1-hydroxy-7-methyl-1,3-dihydrobenzo[c][1,2]oxaborol-6-yloxy)pyrazine-2-carboxamide

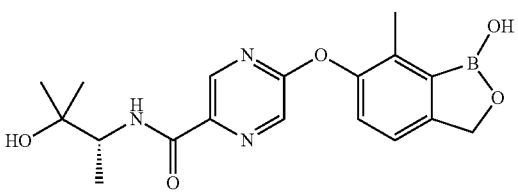 [SMILES: Cc1c(Oc2cnc(C(=O)N[C@H](C)C(C)(C)O)cn2)ccc2c1B(O)OC2]

Step 1: Preparation of (R)-methyl 2-aminopropanoate hydrochloride

To a solution of (R)-2-aminopropanoic acid (1.0 g, 11.23 mmol) in MeOH (30 mL) at 0° C. was added dropwise $SOCl_2$ (2.67 g, 22.47 mmol). The reaction mixture was refluxed for 2 h, and then solvent was removed to give crude (R)-methyl 2-aminopropanoate hydrochloride (1.7 g) as a white solid. It was used in next step without further purification.

Step 2: Preparation of (R)-3-amino-2-methylbutan-2-ol

To a solution of crude (R)-methyl 2-aminopropanoate hydrochloride (1.7 g, 12.23 mmol) in THF (30 mL) at 0° C. was added dropwise MeMgBr (3M, 16 mL, 48.92 mmol). The reaction mixture was stirred at rt overnight. The mixture was quenched with saturated $NH_4Cl$ and extracted with EtOAc (20 mL×3). The combined organic layers were washed with brine, dried over $Na_2SO_4$, filtered and concentrated under reduced pressure. The residue was purified by column chromatography over silical gel by eluted with MeOH: DCM: $Et_3N$ (10:80:3) to give (R)-3-amino-2-methylbutan-2-ol (80 mg) as a colorless oil. It was used in next step without further purification. MS: m/z=104.1 (M+1, ESI+).

Step 3: Preparation of (R)—N-(3-hydroxy-3-methylbutan-2-yl)-5-(1-hydroxy-7-methyl-1, 3-dihydrobenzo[c][1,2]oxaborol-6-yloxy)pyrazine-2-carboxamide A solution of 5-(1-hydroxy-7-methyl-1,3-dihydrobenzo[c][1,2]oxaborol-6-yloxy)pyrazine-2-carboxylic acid (60 mg, 0.21 mmol), HATU (120 mg, 0.31 mmol) and DIPEA (81 mg, 0.63 mmol) in DMF (3 mL) was stirred at rt for 30 min. Then (R)-3-amino-2-methylbutan-2-ol (26 mg, 0.25 mmol) was added and the reaction mixture was stirred at rt overnight. The crude product obtained from a normal work-up was purified by prep-HPLC to give (R)—N-(3-hydroxy-3-methylbutan-2-yl)-5-(1-hydroxy-7-methyl-1,3-dihydrobenzo[c][1,2]oxaborol-6-yloxy)pyrazine-2-carboxamide (7.6 mg, yield 10%) as a white solid. $^1H$ NMR (400 MHz, DMSO-$d_6$): δ 9.09 (s, 1H), 8.67 (s, 1H), 8.62 (s, 1H), 8.12 (d, J=9.2 Hz, 1H), 7.30 (d, J=8.0 Hz, 1H), 7.26 (d, J=8.0 Hz, 1H), 4.99 (s, 2H), 4.72 (s, 1H), 3.92-3.87 (m, 1H), 2.22 (s, 3H), 1.15 (s, 3H), 1.12 (d, J=6.4 Hz, 3H), 1.09 (s, 3H) ppm; HPLC purity: 100% at 214 nm and 100% at 254 nm; MS: m/z=372.1 (M+1, ESI+); Chiral purity: 100% at 220 nm.

Example 49

5-((1-hydroxy-7-methyl-1,3-dihydrobenzo[c][1,2]oxaborol-6-yl)oxy)-N-(cis-2-hydroxycyclopentyl)pyrazine-2-carboxamide

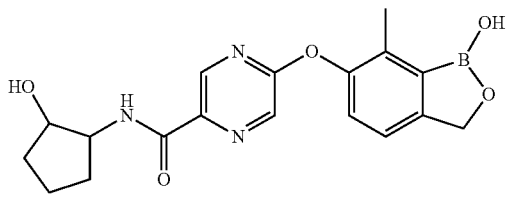 [SMILES: Cc1c(Oc2cnc(C(=O)NC3CCCC3O)cn2)ccc2c1B(O)OC2]

Preparation of 5-((1-hydroxy-7-methyl-1,3-dihydrobenzo[c][1,2]oxaborol-6-yl)oxy)-N-(cis-2-hydroxycyclopentyl)pyrazine-2-carboxamide A solution of 5-(1-hydroxy-7-methyl-1,3-dihydrobenzo[c][1,2]oxaborol-6-yloxy)pyrazine-2-carboxylic acid (80 mg, 0.28 mmol), HATU (213 mg, 0.56 mmol) and DIPEA (144 mg, 1.12 mmol) in DMF (3 mL) was stirred at rt for 30 min. Then cis-2-aminocyclopentan-1-ol hydrochloride (42 mg, 0.42 mmol) was added and the reaction mixture was stirred at rt overnight. The crude compound obtained from a normal work-up was purified by prep-HPLC to give the final product. Since the starting material 2-aminocyclopentan-1-ol was a mixture of the two cis-isomers [(1R,2S)-2-aminocyclopentan-1-ol and (1S,2R)-2-aminocyclopentan-1-ol], the final product contains 5-((1-hydroxy-7-methyl-1,3-dihydrobenzo[c][1,2]oxaborol-6-yl)oxy)-N-((1S,2R)-2-hydroxycyclo pentyl)pyrazine-2-carboxamide and 5-((1-hydroxy-7-methyl-1,3-dihydrobenzo[c][1,2]oxaborol-6-yl)oxy)-N-((1R,2S)-2-hydroxycyclo pentyl)pyrazine-2-carboxamide with a 50:50 ratio (19 mg, yield 18%) as a white solid. $^1$H NMR (400 MHz, DMSO-$d_6$): δ 9.08 (s, 1H), 8.67 (d, J=0.8 Hz, 1H), 8.62 (d, J=0.8 Hz, 1H), 8.18 (d, J=7.6 Hz, 1H), 7.30 (d, J=8.0 Hz, 1H), 7.26 (d, J=8.0 Hz, 1H), 5.12 (d, J=4.4 Hz, 1H), 4.99 (s, 2H), 4.03 (d, J=6.0 Hz, 2H), 2.21 (s, 3H), 2.00-1.85 (m, 1H), 1.85-1.70 (m, 2H), 1.70-1.50 (m, 3H) ppm; HPLC purity: 100% at 220 nm and 100% at 254 nm; MS: m/z=370.0 (M+1, ESI+).

Example 50

(S)-(5-(1-hydroxy-7-methyl-1,3-dihydrobenzo[c][1,2]oxaborol-6-yloxy)pyrazin-2-yl) (2-(hydroxymethyl)piperazin-1-yl)methanone Hydrochloric Acid Salt

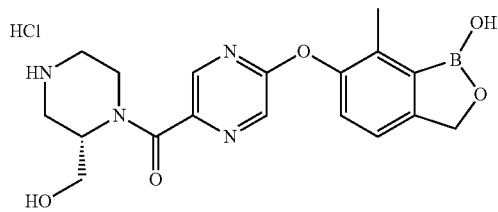 [SMILES: Cl ; Cc1c(Oc2cnc(C(=O)N3CCNC[C@H]3CO)cn2)ccc2c1B(O)OC2]

Step 1: Preparation of (S)-tert-butyl 4-(5-(1-hydroxy-7-methyl-1,3-dihydrobenzo[c][1,2]oxaborol-6-yloxy)pyrazine-2-carbonyl)-3-(hydroxymethyl)piperazine-1-carboxylate A solution of 5-(1-hydroxy-7-methyl-1,3-dihydrobenzo[c][1,2]oxaborol-6-yloxy)pyrazine-2-carboxylic acid (100 mg, 0.35 mmol), HATU (200 mg, 0.52 mmol) and DIPEA (135 mg, 1.05 mmol) in DMF (5 mL) was stirred at rt for 30 min. Then (S)-tert-butyl 3-(hydroxymethyl)piperazine-1-carboxylate (90 mg, 0.42 mmol) was added and the reaction mixture was stirred at rt overnight. The crude compound obtained from a normal work-up was purified by prep-HPLC to give (S)-tert-butyl 4-(5-(1-hydroxy-7-methyl-1,3-dihydrobenzo[c][1,2]oxaborol-6-yloxy)pyrazine-2-carbonyl)-3-(hydroxymethyl)piperazine-1-carboxylate (65 mg, yield 38%) as a white solid. $^1$HNMR (400 MHz, DMSO-$d_6$): δ 9.07 (s, 1H), 8.53 (s, 1H), 8.34-8.31 (m, 1H), 7.30 (d, J=8.0 Hz, 1H), 7.26 (d, J=8.0 Hz, 1H), 4.97 (s, 2H), 4.90-4.80 (m, 1H), 4.22-4.19 (m, 1H), 4.04-3.71 (m, 3H), 3.49 (s, 1H), 3.21-2.92 (m, 4H), 2.23 (s, 3H), 1.39 (s, 9H) ppm; MS: m/z=429.1 (M−55, ESI+).

Step 2: Preparation of (S)-(5-(1-hydroxy-7-methyl-1,3-dihydrobenzo[c][1,2]oxaborol-6-yloxy)pyrazin-2-yl) (2-(hydroxymethyl)piperazin-1-yl)methanone To a solution of (S)-tert-butyl 4-(5-(1-hydroxy-7-methyl-1,3-dihydrobenzo[c][1,2]oxaborol-6-yloxy)pyrazine-2-carbonyl)-3-(hydroxymethyl)piperazine-1-carboxylate (65 mg, 0.134 mmol) in DCM (5 mL) was added HCl (0.34 mL, 1.34 mmol, 4 mol/L in 1,4-dioxane). The reaction mixture was stirred at room temperature for 2 h. The solvent was removed by vacuum and the residue was purified by prep-HPLC to give (S)-(5-(1-hydroxy-7-methyl-1,3-dihydrobenzo[c][1,2]oxaborol-6-yloxy)pyrazin-2-yl)(2-(hydroxymethyl)piperazin-1-yl)methanone (6.8 mg, yield 13%) as a white solid. HPLC purity: 98.4% at 214 nm and 100% at 254 nm; MS: m/z=385.1 (M+1, ESI+); Chiral purity: 98.7%.

Example 51

(R)-(5-(1-hydroxy-7-methyl-1,3-dihydrobenzo[c][1,2]oxaborol-6-yloxy)pyrazin-2-yl) (2-(hydroxymethyl)piperazin-1-yl)methanone Hydrochloric Acid Salt

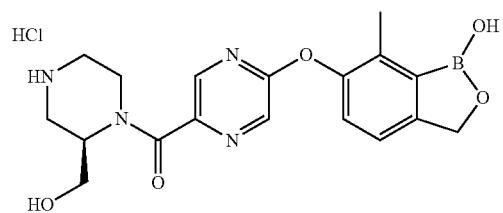 [SMILES: Cl ; Cc1c(Oc2cnc(C(=O)N3CCNC[C@@H]3CO)cn2)ccc2c1B(O)OC2]

Step 1: Preparation of (R)-tert-butyl 4-(5-(1-hydroxy-7-methyl-1,3-dihydrobenzo[c][1,2]oxaborol-6-yloxy)pyrazine-2-carbonyl)-3-(hydroxymethyl)piperazine-1-carboxylate A solution of 5-(1-hydroxy-7-methyl-1,3-dihydrobenzo[c][1,2]oxaborol-6-yloxy)pyrazine-2-carboxylic acid (100 mg, 0.35 mmol), HATU (200 mg, 0.52 mmol) and DIPEA (135 mg, 1.05 mmol) in DMF (5 mL) was stirred at rt for 30 min. (R)-tert-butyl 3-(hydroxymethyl)piperazine-1-carboxylate (90 mg, 0.42 mmol) was added and the reaction mixture was stirred at rt overnight. The crude product after a normal work-up was purified by prep-HPLC to give (R)-tert-butyl 4-(5-(1-hydroxy-7-methyl-1,3-dihydrobenzo[c][1,2]oxaborol-6-yloxy)pyrazine-2-carbonyl)-3-(hydroxymethyl)piperazine-1-carboxylate (65 mg, yield 38%) as a white solid. $^1$HNMR (400 MHz, DMSO-$d_6$) δ 9.07 (s, 1H), 8.53 (s, 1H), 8.35-8.29 (m, 1H), 7.29 (d, J=8.0 Hz, 1H), 7.25 (d, J=8.0 Hz, 1H), 4.97 (s, 2H), 4.90-4.79 (m, 1H), 4.23-4.20 (m, 1H), 4.02-3.68 (m, 3H), 3.48 (s, 2H), 3.05-2.91 (m, 3H), 2.23 (s, 3H), 1.39 (s, 9H) ppm; MS: m/z=429.1 (M−55, ESI+).

Step 2: Preparation of (R)-(5-(1-hydroxy-7-methyl-, 3-dihydrobenzo[c][1,2]oxaborol-6-yloxy)pyrazin-2-yl) (2-(hydroxymethyl)piperazin-1-yl)methanone To a solution of (R)-tert-butyl 4-(5-(1-hydroxy-7-methyl-1,3-dihydrobenzo[c][1,2]oxaborol-6-yloxy)pyrazine-2-carbonyl)-3-(hydroxymethyl)piperazine-1-carboxylate (65 mg, 0.134 mmol) in DCM (5 mL) was added HCl (0.34 mL, 1.34 mmol, 4 mol/L in 1,4-dioxane). The reaction mixture was stirred at room temperature for 2 h. The solvent was removed by vacuum and the residue was purified by prep-HPLC to give (R)-(5-(1-hydroxy-7-methyl-1,3-dihydrobenzo[c][1,2]oxaborol-6-yloxy)pyrazin-2-yl)(2-(hydroxymethyl)piperazin-1-yl)methanone (6.2 mg, 12%) as a white solid. HPLC purity: 100% at 214 nm and 100% at 254 nm; MS: m/z=385.0 (M+1, ESI+); Chiral HPLC purity: 100% at 230 nm.

Example 52

(R)-5-(1-hydroxy-7-methyl-1,3-dihydrobenzo[c][1,2]oxaborol-6-yloxy)-N-(1-hydroxypentan-2-yl)-N-methylpyrazine-2-carboxamide

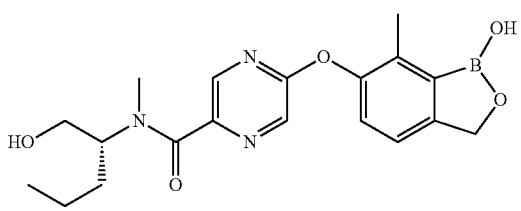 [SMILES: CCC[C@H](CO)N(C)C(=O)c1cnc(Oc2ccc3c(c2C)B(O)OC3)cn1]

Step 1: Preparation of (R)-methyl 2-(tert-butoxycarbonylamino)pentanoate

To a solution of (R)-methyl 2-aminopentanoate hydrochloride (1.6 g) and Et$_3$N (3.7 mL, 25.65 mmol) in DCM (20 mL) was added (Boc)$_2$O (3.7 g, 17.09 mmol). The reaction mixture was stirred at rt overnight. Solvent was removed and the residue was purified by silica gel column chromatography using PE:EA (8:1) as eluent to give (R)-methyl 2-(tert-butoxycarbonylamino)pentanoate (1.8 g, yield 91%) as a colorless oil. MS: m/z=254.2 (M+23, ESI+).

Step 2: Preparation of (R)-2-(methylamino)pentan-1-ol

To a solution of (R)-methyl 2-(tert-butoxycarbonylamino)pentanoate (500 mg, 2.16 mmol) in THF (30 mL) was added LiAlH$_4$ (247 mg, 6.49 mmol). The reaction mixture was refluxed overnight. Water (0.3 mL) was added. The solid was removed by filtration. The filtrate was concentrated and the residue was purified by silica gel column chromatography using DCM: MeOH: Et$_3$N (80:10:3) as eluent to give (R)-2-(methylamino)pentan-1-ol (100 mg) as a colorless oil. MS: m/z=118.2 (M+1, ESI+).

Step 3: Preparation of (R)-5-(1-hydroxy-7-methyl-1,3-dihydrobenzo[c][1,2]oxaborol-6-yloxy)-N-(1-hydroxypentan-2-yl)-N-methylpyrazine-2-carboxamide A solution of 5-(1-hydroxy-7-methyl-1,3-dihydrobenzo[c][1,2]oxaborol-6-yloxy)pyrazine-2-carboxylic acid (600 mg, 2.1 mmol), HATU (1.6 g, 4.2 mmol) and DIPEA (1.1 g, 8.4 mmol) in DMF (10 mL) was stirred at rt for 30 min. (R)-2-(methylamino)pentan-1-ol (269 mg, 2.3 mmol) was added and the reaction mixture was stirred at rt overnight. The crude product after a normal work-up was purified by prep-HPLC to give (R)-5-(1-hydroxy-7-methyl-1,3-dihydrobenzo[c][1,2]oxaborol-6-yloxy)-N-(1-hydroxypentan-2-yl)-N-methylpyrazine-2-carboxamide (284 mg, yield 35%) as a white solid. $^1$H NMR (400 MHz, DMSO-$d_6$): δ 9.08 (s, 1H), 8.56-8.54 (m, 1H), 8.30-8.23 (m, 1H), 7.29 (d, J=8.4 Hz, 1H), 7.25 (d, J=8.4 Hz, 1H), 4.98 (s, 2H), 4.77-4.74 (m, 1H), 4.60-4.50 (m, 0.35H), 3.75-3.65 (m, 0.65H), 3.55-3.31 (m, 2H), 2.83 (s, 3H), 2.23 (s, 3H), 1.48-1.23 (m, 4H), 0.92-0.80 (m, 3H) ppm; HPLC purity: 100% at 214 nm and 100% at 254 nm; MS: m/z=386.2 (M+1, ESI+); Chiral purity 100% at 230 nm.

Example 53

(S)—N-(2-hydroxy-2-methylpentan-3-yl)-5-(1-hydroxy-7-methyl-1,3-dihydrobenzo[c][1,2]oxaborol-6-yloxy)pyrazine-2-carboxamide

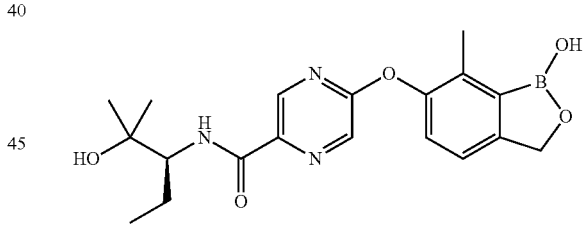

Step 1: Preparation of (S)-methyl 2-aminobutanoate

To a solution of (S)-2-aminobutanoic acid (2.0 g, 19.42 mmol) in MeOH (50 mL) was added SOCl$_2$ (4.6 g, 38.8 mmol) dropwise at 0° C. The reaction mixture was stirred at 70° C. for 2 h, and then concentrated under reduced pressure to give (S)-methyl 2-aminobutanoate hydrochloride (2.0 g, yield 67%) as a white solid. $^1$H NMR (400 Hz, DMSO-$d_6$): δ 8.82 (s, 3H), 4.12 (s, 1H), 3.83 (s, 3H), 2.15-2.08 (m, 2H), 1.12 (t, J=8.0 Hz, 3H) ppm; MS: m/z=118.1 (M+1, ESI+).

Step 2: Preparation of (S)-3-amino-2-methylpentan-2-ol

To a solution of (S)-methyl 2-aminobutanoate hydrochloride (2.0 g, 13.1 mmol) in dry THF (100 mL) was added methylmagnesium bromide (17.5 mL, 52.4 mmol, 3M in ether) at 0° C. The reaction mixture was stirred at room temperature overnight. The mixture was quenched with saturated NH$_4$Cl and extracted with EtOAc (20 mL×3). The combined organic layer was washed with brine, dried over Na$_2$SO$_4$, filtered and concentrated under reduced pressure. The residue was purified by column chromatography over silical gel eluted with DCM: MeOH: TEA (10:1:0.01) to give (S)-3-amino-2-methylpentan-2-ol (800 mg, yield 52%). MS: m/z=118.1 (M+1, ESI+).

Step 3: Preparation of (S)—N-(2-hydroxy-2-methylpentan-3-yl)-5-(1-hydroxy-7-methyl-1, 3-dihydrobenzo[c][1,2]oxaborol-6-yloxy)pyrazine-2-carboxamide A solution of 5-(1-hydroxy-7-methyl-1,3-dihydrobenzo[c][1,2]oxaborol-6-yloxy)pyrazine-2-carboxylic acid (200 mg, 0.7 mmol), HATU (400 mg, 1.05 mmol) and DIPEA (360 mg, 2.78 mmol) in DMF (5 mL) was stirred at rt for 30 min. Then (S)-3-amino-2-methylpentan-2-ol (100 mg, 0.84 mmol) was added and the reaction mixture was stirred at rt overnight. The crude compound obtained after a normal work-up was purified by prep-HPLC to give (S)—N-(2-hydroxy-2-methylpentan-3-yl)-5-(1-hydroxy-7-methyl-1,3-dihydrobenzo[c][1,2]oxaborol-6-yloxy)pyrazine-2-carboxamide (27.3 mg, yield 10%) as a white solid. $^1$HNMR (400 MHz, DMSO-d$_6$): δ 9.08 (s, 1H), 8.68 (d, J=1.2 Hz, 1H), 8.62 (d, J=1.2 Hz, 1H), 7.98 (d, J=10.4 Hz, 1H), 7.30 (d, J=8 Hz, 1H), 7.26 (d, J=8 Hz, 1H), 4.99 (s, 2H), 4.59 (s, 1H), 3.77-3.72 (m, 1H), 2.23 (s, 3H), 1.79-1.76 (m, 1H), 1.47-1.45 (m, 1H), 1.15 (s, 3H), 1.06 (s, 3H), 0.81 (t, J=6.4 Hz, 3H) ppm; HPLC purity: 100% at 214 nm and 100% at 254 nm; MS: m/z=386.1 (M+1, ESI+); Chiral purity: 100% at 230 nm.

Example 54

(3-ethyl-3-hydroxyazetidin-1-yl)(5-((1-hydroxy-7-methyl-1,3-dihydrobenzo[c][1,2]oxaborol-6-yl)oxy)pyrazin-2-yl)methanone

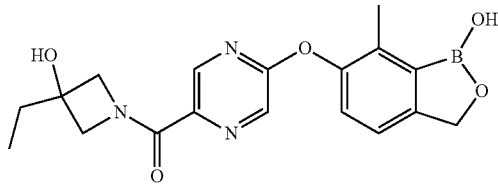 [SMILES: CCC1(O)CN(C(=O)c2cnc(Oc3ccc4c(c3C)B(O)OC4)cn2)C1]

Step 1: Preparation of 1-benzhydryl-3-ethylazetidin-3-ol

To a solution of 1-benzhydrylazetidin-3-one (2.37 g, 10 mmol) in dry THF (50 mL) was added ethylmagnesium bromide (3M, 10 mL, 30 mmol) dropwise at −78° C. After being stirred at −78° C. for 2 h, the reaction mixture was gradually warmed to rt and stirred overnight. Saturated NH$_4$Cl (50 mL) was added and the mixture was extracted with EA (100 mL×3). The combined organic layers were washed with brine, dried over Na$_2$SO$_4$, filtered and concentrated under the reduced pressure. The residue was purified by silica gel column chromatography using PE:EA (4:1) as eluent to give 1-benzhydryl-3-ethylazetidin-3-ol (2.5 g, yield 94%) as a yellow solid. MS: m/z=268.1 (M+1, ESI+).

Step 2: Preparation of 3-ethylazetidin-3-ol hydrochloride

A solution of 1-benzhydryl-3-ethylazetidin-3-ol (1.3 g, 4.9 mmol) and HCl (1N, 4.9 mL) in MeOH (20 mL) was hydrogenated using 10% Pd/C (150 mg) as catalyst under atmospheric pressure of H$_2$ overnight. The catalyst was removed and the solvent was evaporated to give 3-ethylazetidin-3-ol hydrochloride (0.52 g, yield 78%) as a light yellow solid. It was used in next step without further purification.

Step 3: Preparation of (3-ethyl-3-hydroxyazetidin-1-yl) (5-(1-hydroxy-7-methyl-1,3-dihydrobenzo[c][1, 2]oxaborol-6-yloxy)pyrazin-2-yl)methanone A solution of 5-(1-hydroxy-7-methyl-1,3-dihydrobenzo[c][1,2]oxaborol-6-yloxy)pyrazine-2-carboxylic acid (800 mg, 2.8 mmol), HATU (2.13 g, 5.6 mmol) and DIPEA (1.44 g, 11.2 mmol) in DMF (10 mL) was stirred at rt for 30 min. Then 3-ethylazetidin-3-ol hydrochloride (466 mg, 3.4 mmol) was added and the reaction mixture was stirred at rt overnight. The crude compound obtained after a normal work-up was purified by prep-HPLC to give (3-ethyl-3-hydroxyazetidin-1-yl)(5-(1-hydroxy-7-methyl-1,3-dihydrobenzo[c][1,2]oxaborol-6-yloxy)pyrazin-2-yl)methanone (386 mg, yield 37%) as a white solid. $^1$H NMR (400 MHz, DMSO-d$_6$): δ 9.09 (s, 1H), 8.61 (d, J=1.2 Hz, 1H), 8.57 (d, J=1.2 Hz, 1H), 7.29 (d, J=8 Hz, 1H), 7.25 (d, J=8 Hz, 1H), 5.61 (s, 1H), 4.99 (s, 2H), 4.41 (d, J=9.6 Hz, 1H), 4.30 (d, J=10.4 Hz, 1H), 3.96 (d, J=10.0 Hz, 1H), 3.84 (d, J=10.4 Hz, 1H), 2.22 (s, 3H), 1.67 (q, J=7.2 Hz, 2H), 0.88 (t, J=7.2 Hz, 3H) ppm; HPLC purity: 100% at 214 nm and 100% at 254 nm; MS: m/z=370.2 (M+1, ESI+).

Example 55

(3-cyclopropyl-3-hydroxyazetidin-1-yl) (5-((1-hydroxy-7-methyl-1,3-dihydrobenzo[c][1,2]oxaborol-6-yl)oxy)pyrazin-2-yl)methanone

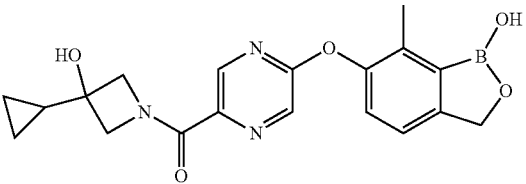 [SMILES: Cc1c(Oc2cnc(C(=O)N3CC(O)(C4CC4)C3)cn2)ccc2c1B(O)OC2]

Step 1: Preparation of 1-benzhydryl-3-cyclopropylazetidin-3-ol

To a solution of 1-benzhydrylazetidin-3-one (1.5 g, 6.3 mmol) in dry THF (50 mL) was added cyclopropylmagnesium bromide (0.5M, 25.2 mL, 12.6 mmol) dropwise at −78° C. After being stirred at −78° C. for 2 h, the reaction mixture was gradually warmed to rt and stirred overnight. Saturated NH$_4$Cl (50 mL) was added and extracted with EA (3×100 mL). The combined organic layers were washed with brine, dried over Na$_2$SO$_4$, filtered and concentrated under the reduced pressure. The residue was purified by silica gel column chromatography eluted with PE:EA (4:1, v/v) to give 1-benzhydryl-3-cyclopropylazetidin-3-ol (1.0 g, yield 57%) as a yellow solid. MS: m/z=280.1 (M+1, ESI+).

Step 2: Preparation of 3-cyclopropylazetidin-3-ol hydrochloride

A solution of 1-benzhydryl-3-cyclopropylazetidin-3-ol (1.0 g, 3.6 mmol) and HCl (1N, 3.6 mL) in MeOH (20 mL) was hydrogenated using 10% Pd/C (150 mg) as catalyst under atmospheric pressure of $H_2$ overnight. The catalyst was removed by filtration and the solvent was evaporated to give 3-cyclopropylazetidin-3-ol hydrochloride (0.4 g, yield 75%) as a light yellow solid. It was used in next step without further purification.

Step 3: Preparation of (3-cyclopropyl-3-hydroxyazetidin-1-yl) (5-(1-hydroxy-7-methyl-1, 3-dihydrobenzo[c][1,2]oxaborol-6-yloxy)pyrazin-2-yl) methanone A solution of 5-(1-hydroxy-7-methyl-1,3-dihydrobenzo[c][1,2]oxaborol-6-yloxy)pyrazine-2-carboxylic acid (700 mg, 2.45 mmol), HATU (1.86 g, 4.9 mmol) and DIPEA (1.26 g, 9.8 mmol) in DMF (10 mL) was stirred at rt for 30 min. Then 3-cyclopropylazetidin-3-ol hydrochloride (438 mg, 2.94 mmol) was added and the reaction mixture was stirred at rt overnight. The crude product was purified by prep-HPLC to give (3-cyclopropyl-3-hydroxyazetidin-1-yl)(5-(1-hydroxy-7-methyl-1,3-dihydrobenzo[c][1,2]oxaborol-6-yloxy)pyrazin-2-yl)methanone (300.9 mg, yield 32%) as a white solid. $^1$H NMR (400 MHz, DMSO-$d_6$): δ 9.09 (s, 1H), 8.61 (d, J=1.2 Hz, 1H), 8.56 (d, J=1.2 Hz, 1H), 7.29 (d, J=8.0 Hz, 1H), 7.25 (d, J=8.0 Hz, 1H), 5.66 (s, 1H), 4.99 (s, 2H), 4.35 (d, J=10.4 Hz, 1H), 4.29 (d, J=10.4 Hz, 1H), 3.89 (d, J=10.4 Hz, 1H), 3.82 (d, J=10.4 Hz, 1H), 2.21 (s, 3H), 1.22-1.18 (m, 1H), 0.43-0.40 (m, 2H), 0.34-0.31 (m, 2H) ppm; HPLC purity: 100% at 214 nm and 100% at 254 nm; MS: m/z=382.3 (M+1, ESI+).

Example 56

(3-hydroxy-3-propylazetidin-1-yl) (5-((1-hydroxy-7-methyl-1,3-dihydrobenzo[c][1,2]oxaborol-6-yl)oxy)pyrazin-2-yl)methanone

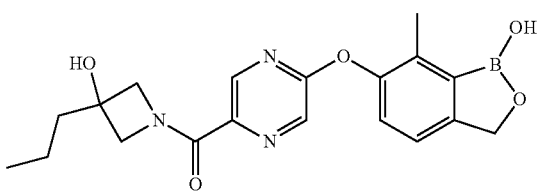 [SMILES: CCCC1(O)CN(C(=O)c2cnc(Oc3ccc4c(c3C)B(O)OC4)cn2)C1]

Step 1: Preparation of 1-benzhydryl-3-propylazetidin-3-ol

To a solution of 1-benzhydrylazetidin-3-one (2.37 g, 10 mmol) in dry THF (50 mL) was added propylmagnesium chloride (2M, 15 mL, 30 mmol) dropwise at −78° C. After being stirred at −78° C. for 2 h, the reaction mixture was gradually warmed to rt and stirred overnight. Saturated $NH_4Cl$ (50 mL) was added and extracted with EA (3×100 mL). The combined organic layers were washed with brine, dried over $Na_2SO_4$, filtered and concentrated under the reduced pressure. The residue was purified by silica gel column chromatography eluted with PE:EA (4:1) to give 1-benzhydryl-3-propylazetidin-3-ol (2.2 g, yield 78%) as a yellow solid. MS: m/z=282 (M+1, ESI+).

Step 2: Preparation of 3-propylazetidin-3-ol hydrochloride

A solution of 1-benzhydryl-3-propylazetidin-3-ol (2.2 g, 7.8 mmol) and HCl (1N, 7.8 mL) in MeOH (30 mL) was hydrogenated using 10% Pd/C (250 mg) as catalyst under atmospheric pressure of $H_2$ overnight. The catalyst was removed by filtration and the solvent was evaporated to give 3-propylazetidin-3-ol hydrochloride (0.8 g, yield 68%) as a light yellow solid. It was used in next step without further purification.

Step 3: Preparation of (3-hydroxy-3-propylazetidin-1-yl) (5-(1-hydroxy-7-methyl-1,3-dihydrobenzo[c][1,2]oxaborol-6-yloxy)pyrazin-2-yl)methanone A solution of 5-(1-hydroxy-7-methyl-1,3-dihydrobenzo[c][1,2]oxaborol-6-yloxy)pyrazine-2-carboxylic acid (800 mg, 2.8 mmol), HATU (2.13 g, 5.6 mmol) and DIPEA (1.44 g, 11.2 mmol) in DMF (10 mL) was stirred at rt for 30 min. Then 3-propylazetidin-3-ol hydrochloride (507 mg, 3.4 mmol) was added and the reaction mixture was stirred at rt overnight. The crude product obtained from a normal workup was purified by prep-HPLC to give (3-hydroxy-3-propylazetidin-1-yl)(5-(1-hydroxy-7-methyl-1,3-dihydrobenzo[c][1,2]oxaborol-6-yloxy)pyrazin-2-yl)methanone (384 mg, yield 36%) as a white solid. $^1$H NMR (400 MHz, DMSO-$d_6$): δ 9.08 (s, 1H), 8.61 (d, J=0.8 Hz, 1H), 8.56 (d, J=0.8 Hz, 1H), 7.29 (d, J=6.4 Hz, 1H), 7.25 (d, J=6.4 Hz, 1H), 5.60 (s, 1H), 4.99 (s, 2H), 4.41 (d, J=8.0 Hz, 1H), 4.31 (d, J=8.0 Hz, 1H), 3.96 (d, J=8.4 Hz, 1H), 3.85 (d, J=8.4 Hz, 1H), 2.22 (s, 3H), 1.63 (t, J=6.4 Hz, 2H), 1.39-1.35 (m, 2H), 0.90 (t, J=6.0 Hz, 3H) ppm; HPLC purity: 100% at 214 nm and 100% at 254 nm; MS: m/z=384.2 (M+1, ESI+).

Example 57

(3-hydroxy-3-isopropylazetidin-1-yl) (5-((1-hydroxy-7-methyl-1,3-dihydrobenzo[c][1,2]oxaborol-6-yl)oxy)pyrazin-2-yl)methanone

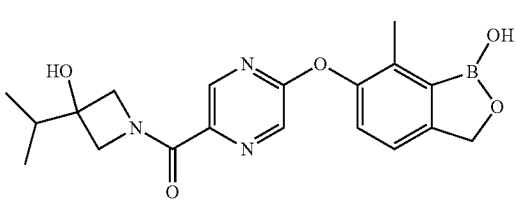 [SMILES: Cc1c(Oc2cnc(C(=O)N3CC(O)(C(C)C)C3)cn2)ccc2c1B(O)OC2]

Step 1: Preparation of 1-benzhydryl-3-isopropylazetidin-3-ol

To a solution of 1-benzhydrylazetidin-3-one (2.37 g, 10 mmol) in dry THF (50 mL) was added isopropylmagnesium chloride (2M, 15 mL, 30 mmol) dropwise at −78° C. After being stirred at −78° C. for 2 h, the reaction mixture was gradually warmed to rt and stirred overnight. Saturated $NH_4Cl$ (50 mL) was added and extracted with EA (3×100 mL). The combined organic layers were washed with brine, dried over $Na_2SO_4$, filtered and concentrated under the reduced pressure. The residue was purified by silica gel column chromatography using PE:EA (4:1) as eluent to give 1-benzhydryl-3-isopropylazetidin-3-ol (1.55 g, yield 55%) as a yellow solid. $^1$H NMR (400 MHz, DMSO-d$_6$): δ 7.40 (d, J=7.2 Hz, 4H), 7.26 (t, J=7.2 Hz, 4H), 7.18 (t, J=7.2 Hz, 2H), 4.93 (s, 1H), 4.41 (s, 1H), 3.12 (d, J=8.0 Hz, 2H), 2.79 (d, J=8.0 Hz, 2H), 1.99 (m, 1H), 0.86 (d, J=6.8 Hz, 6H) ppm; MS: m/z=282.3 (M+1, ESI+).

Step 2: Preparation of 3-isopropylazetidin-3-ol hydrochloride

A solution of 1-benzhydryl-3-isopropylazetidin-3-ol (1.55 g, 5.5 mmol) and HCl (1N, 5.5 mL) in MeOH (25 mL) was hydrogenated using 10% Pd/C (200 mg) as catalyst under atmospheric pressure of H$_2$ overnight. The catalyst was removed and the solvent was evaporated to give 3-isopropylazetidin-3-ol hydrochloride (860 mg, yield 98%) as a light yellow solid. It was used in next step without further purification. MS: m/z=116.2 (M+1, ESI+).

Step 3: Preparation of (3-hydroxy-3-isopropylazetidin-1-yl) (5-(1-hydroxy-7-methyl-1,3-dihydrobenzo[c][1,2]oxaborol-6-yloxy)pyrazin-2-yl)methanone A solution of 5-(1-hydroxy-7-methyl-1,3-dihydrobenzo[c][1,2]oxaborol-6-yloxy)pyrazine-2-carboxylic acid (700 mg, 2.45 mmol), HATU (1.86 g, 4.9 mmol) and DIPEA (1.26 g, 9.8 mmol) in DMF (10 mL) was stirred at rt for 30 min. Then 3-isopropylazetidin-3-ol hydrochloride (444 mg, 2.94 mmol) was added and the reaction mixture was stirred at rt overnight. The crude material was purified by prep-HPLC to give (3-hydroxy-3-isopropylazetidin-1-yl)(5-(1-hydroxy-7-methyl-1,3-dihydrobenzo[c][1,2]oxaborol-6-yloxy)pyrazin-2-yl)methanone (342 mg, yield 36%) as a white solid. $^1$H NMR (400 MHz, DMSO-d$_6$): δ 9.10 (s, 1H), 8.62 (d, J=1.2 Hz, 1H), 8.57 (d, J=1.2 Hz, 1H), 7.29 (d, J=8.4 Hz, 1H), 7.25 (d, J=8.4 Hz, 1H), 5.55 (s, 1H), 4.99 (s, 2H), 4.45 (d, J=10.4 Hz, 1H), 4.27 (d, J=10.4 Hz, 1H), 4.01 (d, J=10.4 Hz, 1H), 3.80 (d, J=10.4 Hz, 1H), 2.21 (s, 3H), 1.85-1.82 (m, 1H), 0.87-0.85 (m, 6H) ppm; HPLC purity: 100% at 214 nm and 100% at 254 nm; MS: m/z=384.2 (M+1, ESI+).

Example 58

(3-hydroxy-3-(trifluoromethyl)azetidin-1-yl) (5-((1-hydroxy-7-methyl-1,3-dihydrobenzo[c][1,2]oxaborol-6-yl)oxy)pyrazin-2-yl)methanone

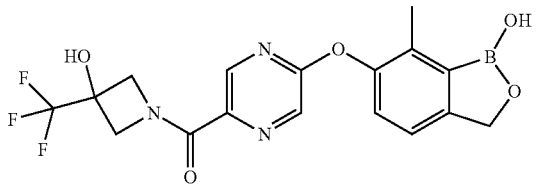 [SMILES: Cc1c(Oc2cnc(C(=O)N3CC(O)(C(F)(F)F)C3)cn2)ccc2c1B(O)OC2]

Step 1: Preparation of 1-benzhydryl-3-(trifluoromethyl)azetidin-3-ol

To a solution of 1-benzhydrylazetidin-3-one (2.0 g, 8.45 mmol) in THF (25 mL) was added trimethyl(trifluoromethyl)silane (1.80 g, 12.65 mmol) and cesium fluoride (1.95 g, 12.85 mmol). The reaction mixture was stirred at room temperature for 1 h and quenched with saturated NH$_4$Cl solution. The mixture was extracted with EtOAc (3×20 mL). The combined organic layers were washed with brine, dried over Na$_2$SO$_4$, filtered and concentrated in vacuum. The crude product was purified by column chromatography on silica gel using PE:EA (4:1) as eluent to give 1-benzhydryl-3-(trifluoromethyl)azetidin-3-ol (1.55 g, yield 60%) as a yellow solid. MS: m/z=308.1 (M+1, ESI+).

Step 2: Preparation of 3-(trifluoromethyl)azetidin-3-ol hydrochloride

A solution of 1-benzhydryl-3-(trifluoromethyl)azetidin-3-ol (1.55 g, 5.04 mmol) and HCl (1N, 5 mL) in MeOH (30 mL) was hydrogenated using 10% Pd/C (200 mg) as catalyst under atmospheric pressure of H$_2$ overnight. The catalyst was removed by filtration and the solvent was evaporated to give 3-(trifluoromethyl)azetidin-3-ol hydrochloride (800 mg, yield 89%) as a light yellow solid. It was used in next step without further purification. MS: m/z=142.1 (M+1, ESI+).

Step 3: Preparation of (3-hydroxy-3-(trifluoromethyl)azetidin-1-yl) (5-(1-hydroxy-7-methyl-1,3-dihydrobenzo[c][1,2]oxaborol-6-yloxy)pyrazin-2-yl)methanone A solution of 5-(1-hydroxy-7-methyl-1,3-dihydrobenzo[c][1,2]oxaborol-6-yloxy)pyrazine-2-carboxylic acid (568 mg, 1.99 mmol), HATU (1.51 g, 3.98 mmol) and DIPEA (1.03 g, 7.96 mmol) in DMF (7 mL) was stirred at rt for 30 min. Then 3-(trifluoromethyl)azetidin-3-ol hydrochloride (423 mg, 2.39 mmol) was added and the reaction mixture was stirred at rt overnight. The crude product was purified by prep-HPLC to give (3-hydroxy-3-(trifluoromethyl)azetidin-1-yl)(5-(1-hydroxy-7-methyl-1,3-dihydrobenzo[c][1,2]oxaborol-6-yloxy)pyrazin-2-yl)methanone (200.8 mg, yield 25%) as a white solid. $^1$H NMR (400 MHz, DMSO-d$_6$): δ 9.08 (s, 1H), 8.65 (d, J=1.2 Hz, 1H), 8.57 (d, J=1.6 Hz, 1H), 7.48 (s, 1H), 7.28 (d, J=8.0 Hz, 1H), 7.24 (d, J=8.0 Hz, 1H), 4.98 (s, 2H), 4.80 (d, J=10.8 Hz, 1H), 4.55 (d, J=11.6 Hz, 1H), 4.31 (d, J=10.8 Hz, 1H), 4.07 (d, J=11.2 Hz, 1H), 2.21 (s, 3H) ppm; HPLC purity: 100% at 214 nm and 100% at 254 nm; MS: m/z=410.1 (M+1, ESI+).

Example 2

In Vitro Activity Against *Plasmodium falciparum*
a) Against 3D7 Strain of *Plasmodium falciparum*

Inhibition of 3D7 strain parasites was assessed using the [$^3$H]-hypoxanthine incorporation assay (Desjardins, et al. *Antimicrob. Agents Chemother.* 1979, 16, 710-718). Briefly, parasites were cultured in human erythrocytes (from the Spanish Red Cross blood bank) using RPMI-1640 culture media (Gibco) supplemented with 0.5% Albumax II (Invitrogen), 2% D-sucrose (Sigma-Aldrich), 0.3% glutamine (Sigma-Aldrich), and 5 mM hypoxanthine (Sigma-Aldrich). Cultures were maintained at 37° C. at an atmosphere of 5% O$_2$, 5% CO$_2$, and 95% N$_2$. To assess inhibition, asynchronous parasite cultures with 0.5% parasitemia and 2% hematocrit were exposed to 3-fold serial dilutions of test compounds for 24 hours in 96 well plate cultures (Costar #3894). After 24 hours, [$^3$H]-hypoxanthine was added, plates were incubated for an additional 24 hours, and parasites were harvested on glass fiber filters (Wallac #1450-421) using a cell harvester 96 (TOMTEC, Perkin Elmer). Filters were dried on scintillator sheets (MeltiLex A, PerkinElmer

1450-441) to determine incorporation of [³H]-hypoxanthine. Radioactivity was measured using a microbeta counter (Perkin Elmer). Data are normalized using the incorporation of the positive control (infected erythrocytes without drug). IC$_{50}$ values were determined using Excel and Grafit 5 software. Values were determined from at least three independent experiments, and standard deviations were calculated.

b) Against W2 Strain of *Plasmodium falciparum*

W2 strain *P. falciparum* parasites were cultured in human erythrocytes and RPMI-1640 culture media with either 10% human serum or 0.5% Albumax serum substitute under 3% O$_2$, 5% CO$_2$, and 92% N$_2$. Parasites synchronized to ring stage by treatments with 5% D-sorbitol were cultured with serial dilutions of benzoxaboroles from 5 to 10 mM stocks in 96 well microplate cultures including 200 μL of media/well, 2% hematocrit, and 1% parasitemia. At the completion of 48 h incubations, when untreated cultures contained new rings, parasites were fixed with 2% formaldehyde for 48 h, and 5 μL aliquots were transferred to another 96 well plate containing 150 μL/well of staining solution (100 mM NH$_4$Cl, 0.1% Triton X-100, and 1 nM YOYO-1 in PBS). Parasites per erythrocyte were then determined by flow cytometry from plots of forward scatter against fluorescence (excitation 488 nm, emission 520 nm) using a FacSort flow cytometer (Beckton Dickinson) equipped with an AMS Loader (Cytek Development). All values were normalized to percent control activity, and IC$_{50}$s were calculated using the Prism 3.0 program (GRAPHPAD Software). Goodness of fit was assessed by R$^2$ values, and meaningful dose-response curves yielded R$^2$ values >0.95.

Clog D c) Clog D

Clog D (pH=7.4) was calculated using ChemAxon software under the condition of pH=7.4.

Data for exemplary compounds of the invention are provided below.

| Ex# | IC50: 1 Org. Growth P. falciparum 3D7, 2 d (LPS__00570) [uM] | IC50: 1 Org. Growth P. falciparum W2, 2 d (LPS__00451) [uM] | Clog D |
|---|---|---|---|
| 1 | 1.08 | 0.372 | 0.25 |
| 2 | 0.644 | 0.788 | 0.83 |
| 3 | 0.425 | 0.29 | 0.74 |
| 4 | 0.554 | 0.334 | 0.74 |
| 5 | 0.317 | 0.0923 | 0.66 |
| 6 | 0.184 | 0.328 | −0.25 |
| 7 | 0.0965 | 0.115 | 1.54 |
| 8 | 0.937 | 0.93 | 1.86 |
| 9 | 1.1 | 1.28 | 0.66 |
| 10 | 0.437 | 0.262 | 0.5 |
| 11 | 0.848 | 0.944 | 0.66 |
| 12 | 0.808 | 0.844 | 0.66 |
| 13 | 0.715 | 0.297 | 1.53 |
| 14 | 0.201 | 0.161 | 1.53 |
| 15 | 0.407 | 0.297 | 2.35 |
| 16 | 0.38 | 0.223 | 2.1 |
| 17 | 1.5 | 2.01 | 0.38 |
| 18 | 0.725 | 0.622 | 1.13 |
| 19 | 0.403 | 0.136 | 1.13 |
| 20 | 0.786 | 0.535 | 1.06 |
| 21 | 0.801 | 0.704 | 1.13 |
| 22 | 1.15 | 0.458 | 1.03 |
| 23 | 1.99 | 0.774 | 1.54 |
| 24 | 0.587 | 0.492 | 1.03 |
| 25 | 0.466 | 0.149 | 1.54 |
| 26 | 0.161 | 0.103 | 2.1 |
| 27 | 0.505 | 0.115 | 2.35 |
| 28 | 0.215 | 0.0849 | 1.93 |
| 29 | 0.764 | 0.828 | 1.06 |
| 30 | 0.536 | 0.317 | 1.06 |
| 31 | 1.09 | 0.643 | 1.03 |
| 32 | 0.796 | 0.512 | 0.16 |
| 33 | 0.149 | 0.0822 | 1.54 |
| 34 | 0.452 | 0.35 | 1.54 |
| 35 | 0.0737 | 0.37 | 0.99 |
| 36 | 0.472 | 0.201 | −.097 |
| 37 | 0.48 | 0.23 | 1.79 |
| 38 | 0.959 | 0.352 | 1.79 |
| 39 | 1.46 | 0.513 | 1.08 |
| 40 | 0.314 | 0.139 | 0.52 |
| 41 | 0.0706 | 0.0326 | 0.47 |
| 42 | 0.245 | 0.133 | 1.11 |
| 43 | 0.553 | 0.26 | 2.02 |
| 44 | 0.217 | 0.129 | 2.02 |
| 45 | 0.222 | 0.0918 | 1.62 |
| 46 | 0.537 | 0.149 | 1.11 |
| 47 | 0.327 | 0.202 | 1.16 |
| 48 | 0.374 | 0.265 | 1.16 |
| 49 | 0.181 | 0.292 | 1.11 |
| 50 | 0.171 | 0.0982 | −0.29 |
| 51 | 0.151 | 0.103 | −0.29 |
| 52 | 0.252 | 0.0481 | 1.78 |
| 53 | 0.829 | 0.279 | 1.62 |
| 54 | 0.087 | 0.0289 | 0.94 |
| 55 | 0.234 | 0.0517 | 0.84 |
| 56 | 0.137 | 0.0159 | 1.33 |
| 57 | 0.369 | 0.0407 | 1.34 |
| 58 | 0.0139 | 0.0066 | 1.10 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure according to formula (I) and/or (II):

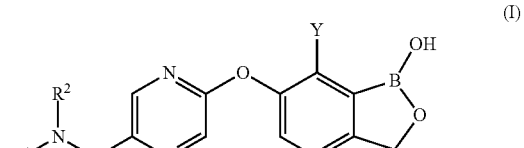

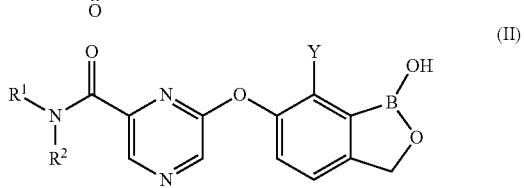

wherein Y is substituted or unsubstituted C$_1$-C$_3$ alkyl or substituted or unsubstituted C$_1$-C$_3$ alkyloxy, and R$^1$ and R$^2$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein R$^1$ and R$^2$, along with the nitrogen to which they are attached, can be optionally joined to form a substituted or unsubstituted 3 to 8 membered ring, or a salt, or a hydrate, or a solvate thereof.

2. The compound of claim 1, wherein $R^1$ is according to formula (III):

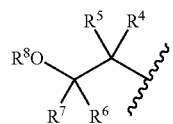

(III)

wherein $R^8$ is H or substituted or unsubstituted alkyl, and $R^4$ or $R^5$ or $R^6$ or $R^7$ are each independently selected from H, substituted or unsubstituted $C_1$-$C_6$ alkyl, substituted or unsubstituted heteroalkyl, substituted or unsubstituted $C_3$-$C_8$ cycloalkyl, substituted or unsubstituted aryl, or substituted or unsubstituted heteroaryl, and wherein $R^4$ and $R^5$, along with the atoms to which they are attached, can be optionally joined to form a substituted or unsubstituted 3 to 8 membered ring, and wherein $R^7$ and $R^8$, along with the atoms to which they are attached, can be optionally joined to form a substituted or unsubstituted 3 to 8 membered ring, and wherein $R^5$ and $R^6$, along with the atoms to which they are attached, can be optionally joined to form a substituted or unsubstituted 3 to 8 membered ring.

3. The compound of claim 1, having a structure according to formula (Ia) and/or (IIa):

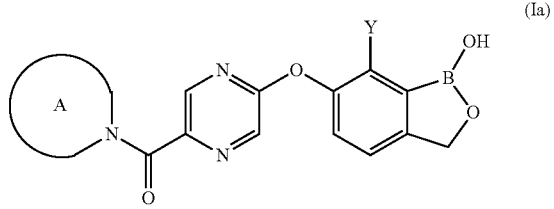

(Ia)

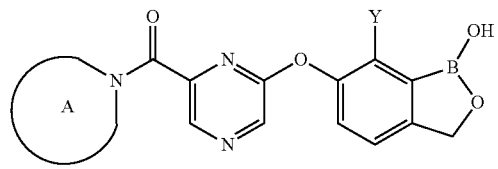

(IIa)

wherein A is a substituted or unsubstituted 3 to 8 membered ring.

4. A combination comprising the compound of claim 1, together with at least one additional therapeutic agent.

5. A pharmaceutical formulation comprising:
   a) the compound of claim 1; and
   b) a pharmaceutically acceptable excipient.

6. The pharmaceutical formulation of claim 5, wherein the pharmaceutical formulation is a unit dosage form.

7. The pharmaceutical formulation of claim 5, wherein the salt of the compound of claim 1 is a pharmaceutically acceptable salt.

8. A method of killing the growth of a protozoa, comprising: contacting the protozoa with an effective amount of the compound of claim 1, thereby killing the growth of the protozoa.

9. The method of claim 8, wherein the protozoa is a member of the *Plasmodium* genus.

10. The method of claim 8, wherein the protozoa is *Plasmodium falciparum*.

11. A method of treating a disease an animal, comprising: administering to the animal a therapeutically effective amount of the compound of claim 1, thereby treating the disease.

12. The method of claim 11, wherein the disease is malaria.

13. The method of claim 11, wherein the animal is a human.

* * * * *